(12) United States Patent
Takahashi et al.

(10) Patent No.: US 9,615,580 B2
(45) Date of Patent: *Apr. 11, 2017

(54) FUSED HETEROCYCLIC COMPOUND AND USE THEREOF FOR PEST CONTROL

(71) Applicant: Sumitomo Chemical Company, Limited, Tokyo (JP)

(72) Inventors: Masaki Takahashi, Takarazuka (JP); Takamasa Tanabe, Takarazuka (JP); Mai Ito, Takarazuka (JP); Atsushi Iwata, Walnut Creek, CA (US); Yoshihiko Nokura, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/651,348

(22) PCT Filed: Dec. 26, 2013

(86) PCT No.: PCT/JP2013/085339
§ 371 (c)(1),
(2) Date: Jun. 11, 2015

(87) PCT Pub. No.: WO2014/104407
PCT Pub. Date: Jul. 3, 2014

(65) Prior Publication Data
US 2015/0313234 A1 Nov. 5, 2015

(30) Foreign Application Priority Data

Dec. 27, 2012 (JP) ................................. 2012-284302
Jan. 30, 2013 (JP) ................................. 2013/015197

(51) Int. Cl.
| | | |
|---|---|---|
| A01N 43/90 | (2006.01) | |
| C07D 413/04 | (2006.01) | |
| A01N 43/76 | (2006.01) | |
| C07D 213/81 | (2006.01) | |
| A01N 25/18 | (2006.01) | |
| C07D 263/57 | (2006.01) | |
| C07D 498/04 | (2006.01) | |

(52) U.S. Cl.
CPC ............ *A01N 43/90* (2013.01); *A01N 25/18* (2013.01); *A01N 43/76* (2013.01); *C07D 213/81* (2013.01); *C07D 263/57* (2013.01); *C07D 413/04* (2013.01); *C07D 498/04* (2013.01)

(58) Field of Classification Search
None
See application file for complete search history.

(56) References Cited

U.S. PATENT DOCUMENTS 4,581,297 A    4/1986  Delseth et al.
8,071,701 B2  12/2011  Klosin et al.
9,018,134 B2 *  4/2015  Takahashi .............. A01N 43/76
                                                            504/246
9,156,838 B2 * 10/2015  Takahashi ............ C07D 263/56
2011/0039843 A1  2/2011  Iwakoshi et al.
2012/0015975 A1  1/2012  Takahashi et al.
2012/0196891 A1  8/2012  Iwakoshi
2013/0090353 A1  4/2013  Iwakoshi et al.
2013/0252981 A1  9/2013  Takahashi et al.
2014/0194290 A1 *  7/2014  Takahashi .............. A01N 43/76
                                                            504/246
2015/0166573 A1 *  6/2015  Takahashi .............. A01N 43/76
                                                            514/252.04
2015/0197532 A1 *  7/2015  Takahashi .............. A01N 43/76
                                                            546/114

(Continued)

FOREIGN PATENT DOCUMENTS

CN       1067653 A    1/1993
CN     102006776 A    4/2011

(Continued)

OTHER PUBLICATIONS

George A. Patani "Bioisosterism: A Rational Approach in Drug Design" Chemical Reviews 1996, 96, 3147-3176.*
Wermuth, Camille G. "Molecular Variation Based on Isosteric Replacements" in Chapter 13, The Practice of Medicinal Chemistry, Academic: 1996.*
Office Action issued Jan. 27, 2016 in CN Application No. 201380068070.4.
International Search Report and Written Opinion issued Nov. 26, 2012 in International Application No. PCT/JP2012/070409.

(Continued)

*Primary Examiner* — David K O'Dell
(74) *Attorney, Agent, or Firm* — Panitch Schwarze Belisario & Nadel LLP

(57) ABSTRACT

Disclosed is a compound represented by formula (1):

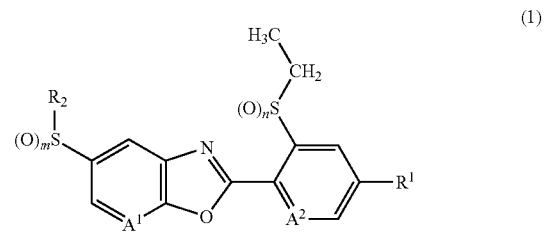

wherein $A^1$ represents $N(O)_p$ or CH; $A^2$ represents $N(O)_q$; $R^1$ represents a trifluoromethyl group, a halogen atom or a hydrogen atom; $R^2$ represents a C1-C3 perfluoroalkyl group, p represents 0 or 1; q represents 0 or 1; n represents 0, 1 or 2; and m represents 0, 1 or 2, having an excellent controlling effect on pests.

16 Claims, No Drawings

(56) References Cited

U.S. PATENT DOCUMENTS

2015/0246911 A1* 9/2015 Takahashi ............ C07D 263/56
514/302

FOREIGN PATENT DOCUMENTS

| EP | 0508800 A1 | 10/1992 | | |
|---|---|---|---|---|
| EP | 1302466 A1 | 4/2003 | | |
| EP | 2274983 A1 | 1/2011 | | |
| JP | 2004-034438 A | 2/2004 | | |
| JP | WO 2013180194 A1 * | 12/2013 | ............ | A01N 43/76 |
| JP | WO 2013187425 A1 * | 12/2013 | ............ | A01N 43/52 |
| WO | 2011040629 A1 | 4/2011 | | |
| WO | 2011049221 A1 | 4/2011 | | |
| WO | 2012086848 A1 | 6/2012 | | |
| WO | 2013018928 A1 | 2/2013 | | |

OTHER PUBLICATIONS

International Preliminary Report on Patentability issued Feb. 13, 2014 in International Application No. PCT/JP2012/070409.
Office Action issued Feb. 4, 2015 in CN Application No. 201280037185.2.
International Search Report issued Mar. 18, 2014 in International Application No. PCT/JP2013/085339.
International Preliminary Report on Patentability issued Jun. 30, 2015 in International Application No. PCT/JP2013/085339.
Office Action issued Jun. 1, 2016 in CN Application No. 201380068070.4.
Office Action issued Sep. 1, 2016 in EP Application No. 13821998.5.

* cited by examiner

FUSED HETEROCYCLIC COMPOUND AND USE THEREOF FOR PEST CONTROL

CROSS-REFERENCE TO RELATED APPLICATION

This application is a Section 371 of International Application No. PCT/JP2013/085339, filed Dec. 26, 2012, which was published in the English language on Jul. 3, 2014, under International Publication No. WO 2014/104407 A1, and the disclosure of which is incorporated herein by reference.

TECHNICAL FIELD

The present application is filed claiming the priority of the Japanese Patent Applications No. 2012-284302 and 2013-015197, the entire contents of which are herein incorporated by reference.

The present invention relates to a fused heterocyclic compound and the use thereof for pest control.

BACKGROUND ART

For controlling pests, various compounds have been developed and used practically.

Further, some fused heterocyclic compounds are known (see, Patent Literature 1).

CITATION LIST

Patent Literature

Patent Literature 1: JP 2004-34438 A

SUMMARY OF INVENTION

Technical Problem

An object of the present invention is to provide a compound having an excellent controlling effect on pests and a method for controlling pests by using said compound.

Solution to Problem

The inventors of the present invention have intensively studied, and as a result, they have found that a fused heterocyclic compound represented by the following formula (1) has an excellent controlling effect on pests. Thus, the present invention has been completed.

The present invention includes the followings:

[1] A fused heterocyclic compound represented by formula (1):

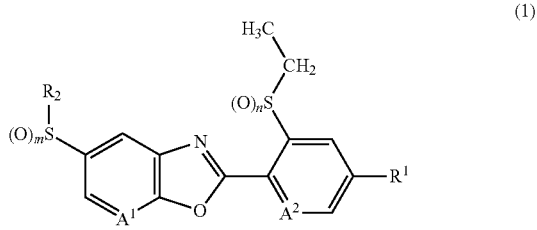

(1)

wherein
$A^1$ represents $N(O)_p$ or CH,
$A^2$ represents $N(O)_q$,
$R^1$ represents a trifluoromethyl group, a halogen atom or a hydrogen atom,
$R^2$ represents a C1-C3 perfluoroalkyl group,
p represents 0 or 1,
q represents 0 or 1,
n represents 0, 1 or 2,
m represents 0, 1 or 2,
with the proviso that when $A^1$ is NO and/or $A^2$ is NO, n represents 2 and m represents 2.
(hereinafter referred to as "the present compound").

[2] The compound according to the above [1], wherein $A^1$ is CH.

[3] The compound according to the above [1], wherein $A^1$ is N.

[4] The compound according to any one of the above [1]-[3], wherein $R^1$ is a hydrogen atom.

[5] The compound according to any one of the above [1]-[3], wherein $R^1$ is a trifluoromethyl group.

[6] The compound according to any one of the above [1]-[5], wherein $R^2$ is a trifluoromethyl group.

[7] The compound according to any one of the above [1]-[6], wherein p is 0 and q is 0.

[8] A pest control agent comprising a compound according to any one of the above [1] to [7] and an inert carrier.

[9] The pest control agent according to the above [8], wherein the inert carrier is water, and the compound according to any one of the above [1]-[7] is dispersed in the water containing a surfactant.

[10] A method for controlling a pest, which comprises applying an effective amount of the compound according to any one of the above [1] to [7].

[11] The method according to the above [10], which comprises applying an effective amount of the compound according to any one of the above [1] to [7] to stem and leaf of a plant or a soil where a plant is grown.

[12] The pest control agent according to the above [8], wherein the inert carrier is an eating carrier.

[13] The pest control agent according to the above [8], wherein the inert carrier is a solvent and a propellant gas.

[14] The method according to the above [10], which comprises spraying the pest control agent according to the above [13] to a pest and/or a habitat of a pest.

[15] The pest control agent according to the above [8], wherein the inert carrier is a gas-forming agent.

[16] The method according to the above [10], which comprises applying the compound according to any one of the above [1] to [7] to the body surface of an animal parasitized by a pest.

[17] The method according to the above [10], which comprises orally administering the compound according to any one of the above [1] to [7] to an animal parasitized by a pest.

[18] A compound represented by formula (M4):

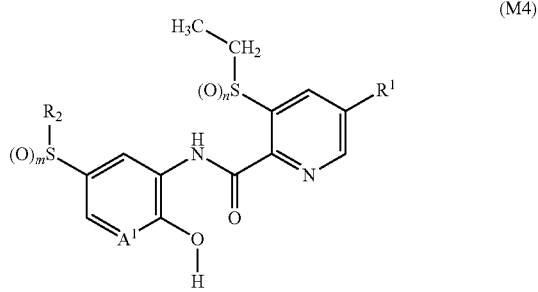

(M4)

wherein
$A^1$ represents N or CH,
$R^1$ represents a trifluoromethyl group, a halogen atom or a hydrogen atom,
$R^2$ represents a C1-C3 perfluoroalkyl group, n represents 0, 1 or 2,
m represents 0, 1 or 2.
(hereinafter referred to as "the intermediate compound (M4)").

[19] A compound represented by formula (M6):

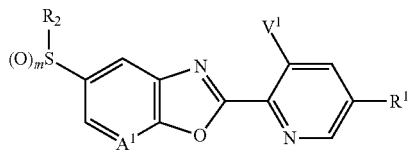

(M6)

wherein
$A^1$ represents N or CH,
$V^1$ represents a fluorine atom or a chlorine atom,
$R^2$ represents a C1-C3 perfluoroalkyl group,
m represents 0, 1 or 2.
(hereinafter referred to as "the intermediate compound (M6)").

[20] A compound represented by formula (M10):

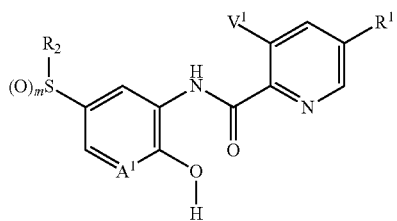

(M10)

wherein
$A^1$ represents N or CH,
$V^1$ represents a fluorine atom or a chlorine atom,
$R^2$ represents a C1-C3 perfluoroalkyl group,
m represents 0, 1 or 2.
(hereinafter referred to as "the intermediate compound (M10)").

Effect of Invention

The present compound has an excellent controlling effect on pests and is thus useful as an active ingredient of a pest control agent.

The compound represented by formula (1) wherein n is 1 and/or m is 1 includes stereoisomers. Each stereoisomer has an excellent controlling effect on pests.

Examples of these stereoisomers include the following compounds:
A compound represented by formula (1E):

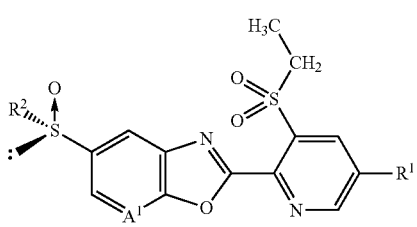

(1E)

wherein $A^1$ represents N or CH, and the other symbols are as defined in the formula (1).
A compound represented by formula (1F):

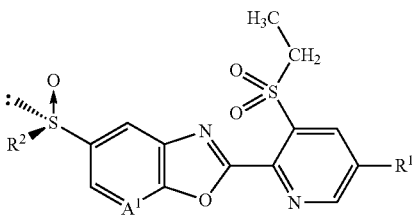

(1F)

wherein $A^1$ represents N or CH, and the other symbols are as defined in the formula (1).

MODE FOR CARRYING OUT THE INVENTION

The groups used herein will be illustrated in detail by way of examples.

The "halogen atom" in the present compound includes a fluorine atom, a chlorine atom, a bromine atom and an iodine atom.

The "Ca-Cb perfluoroalkyl" used herein refers to a linear or branched alkyl group having a-b carbon atoms, to which all the hydrogen atoms attached are substituted by fluorine atoms.

Examples of the "C1-C3 perfluoroalkyl group" include a trifluoromethyl group, a pentafluoroethyl group, a heptafluoropropyl group, and a heptafluoroisopropyl group.

Examples of the present compound include the following compounds:
A compound represented by formula (1) wherein $A^1$ is N;
A compound represented by formula (1) wherein $A^1$ is CH;
A compound represented by formula (1) wherein $A^2$ is N;
A compound represented by formula (1) wherein $R^1$ is a trifluoromethyl group;
A compound represented by formula (1) wherein $R^1$ is a fluorine atom;
A compound represented by formula (1) wherein $R^1$ is a chlorine atom;
A compound represented by formula (1) wherein $R^1$ is a bromine atom;
A compound represented by formula (1) wherein $R^1$ is an iodine atom;
A compound represented by formula (1) wherein $R^1$ is a hydrogen atom;
A compound represented by formula (1) wherein $R^2$ is a trifluoromethyl group;
A compound represented by formula (1) wherein $R^2$ is a pentafluoroethyl group;
A compound represented by formula (1) wherein $R^2$ is a heptafluoropropyl group;
A compound represented by formula (1) wherein $R^2$ is a heptafluoroisopropyl group;
A compound represented by formula (1) wherein n is 0;
A compound represented by formula (1) wherein n is 1;
A compound represented by formula (1) wherein n is 2;
A compound represented by formula (1) wherein m is 0;
A compound represented by formula (1) wherein m is 1;
A compound represented by formula (1) wherein m is 2;
A compound represented by formula (1) wherein $A^1$ is N, $A^2$ is N, $R^1$ is a trifluoromethyl group, and $R^2$ is a trifluoromethyl group;

A compound represented by formula (1) wherein $A^1$ is N, $A^2$ is N, $R^1$ is a chlorine atom, and $R^2$ is a trifluoromethyl group;

A compound represented by formula (1) wherein $A^1$ is N, $A^2$ is N, $R^1$ is a bromine atom, and $R^2$ is a trifluoromethyl group;

A compound represented by formula (1) wherein $A^1$ is N, $A^2$ is N, $R^1$ is a hydrogen atom, and $R^2$ is a trifluoromethyl group;

A compound represented by formula (1) wherein $A^1$ is CH, $A^2$ is N, $R^1$ is a trifluoromethyl group, and $R^2$ is a trifluoromethyl group;

A compound represented by formula (1) wherein $A^1$ is CH, $A^2$ is N, $R^1$ is a chlorine atom, and $R^2$ is a trifluoromethyl group;

A compound represented by formula (1) wherein $A^1$ is CH, $A^2$ is N, $R^1$ is a bromine atom, and $R^2$ is a trifluoromethyl group;

A compound represented by formula (1) wherein $A^1$ is CH, $A^2$ is N, $R^1$ is a hydrogen atom, and $R^2$ is a trifluoromethyl group;

A compound represented by formula (1) wherein $A^1$ is N, $A^2$ is N, $R^1$ is a trifluoromethyl group, $R^2$ is a trifluoromethyl group, and n is 2;

A compound represented by formula (1) wherein $A^1$ is N, $A^2$ is N, $R^1$ is a chlorine atom, $R^2$ is a trifluoromethyl group, and n is 2;

A compound represented by formula (1) wherein $A^1$ is N, $A^2$ is N, $R^1$ is a bromine atom, $R^2$ is a trifluoromethyl group, and n is 2;

A compound represented by formula (1) wherein $A^1$ is N, $A^2$ is N, $R^1$ is a hydrogen atom, $R^2$ is a trifluoromethyl group, and n is 2;

A compound represented by formula (1) wherein $A^1$ is CH, $A^2$ is N, $R^1$ is a trifluoromethyl group, $R^2$ is a trifluoromethyl group, and n is 2;

A compound represented by formula (1) wherein $A^1$ is CH, $A^2$ is N, $R^1$ is a chlorine atom, $R^2$ is a trifluoromethyl group, n is 2;

A compound represented by formula (1) wherein $A^1$ is CH, $A^2$ is N, $R^1$ is a bromine atom, $R^2$ is a trifluoromethyl group, n is 2;

A compound represented by formula (1) wherein $A^1$ is CH, $A^2$ is N, $R^1$ is a hydrogen atom, $R^2$ is a trifluoromethyl group, n is 2;

A compound represented by formula (1) wherein $A^1$ is N, $A^2$ is N, $R^1$ is a trifluoromethyl group, $R^2$ is a trifluoromethyl group, n is 2, and m is 1 or 2;

A compound represented by formula (1) wherein $A^1$ is N, $A^2$ is N, $R^1$ is a chlorine atom, $R^2$ is a trifluoromethyl group, n is 2, and m is 1 or 2;

A compound represented by formula (1) wherein $A^1$ is N, $A^2$ is N, $R^1$ is a bromine atom, $R^2$ is a trifluoromethyl group, n is 2, and m is 1 or 2;

A compound represented by formula (1) wherein $A^1$ is N, $A^2$ is N, $R^1$ is a hydrogen atom, $R^2$ is a trifluoromethyl group, n is 2, and m is 1 or 2;

A compound represented by formula (1) wherein $A^1$ is CH, $A^2$ is N, $R^1$ is a trifluoromethyl group, $R^2$ is a trifluoromethyl group, n is 2, and m is 1 or 2;

A compound represented by formula (1) wherein $A^1$ is CH, $A^2$ is N, $R^1$ is a chlorine atom, $R^2$ is a trifluoromethyl group, n is 2, and m is 1 or 2;

A compound represented by formula (1) wherein $A^1$ is CH, $A^2$ is N, $R^1$ is a bromine atom, $R^2$ is a trifluoromethyl group, n is 2, and m is 1 or 2;

A compound represented by formula (1) wherein $A^1$ is CH, $A^2$ is N, $R^1$ is a hydrogen atom, $R^2$ is a trifluoromethyl group, n is 2, and m is 1 or 2;

Specific examples of the present compound wherein p is 0 and q is 0 include the compound represented by formula (1D) (hereinafter referred to as "the present compound (1D)"):

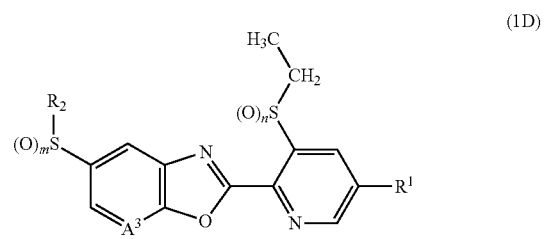

wherein $A^3$ represents N or CH, and $R^1$, $R^2$, n and m are as defined in the formula (1).

A compound represented by formula (1D) wherein $A^3$ is N;
A compound represented by formula (1D) wherein $A^3$ is CH;
A compound represented by formula (1D) wherein $R^1$ is a trifluoromethyl group;
A compound represented by formula (1D) wherein $R^1$ is a fluorine atom;
A compound represented by formula (1D) wherein $R^1$ is a chlorine atom;
A compound represented by formula (1D) wherein $R^1$ is a bromine atom;
A compound represented by formula (1D) wherein $R^1$ is an iodine atom;
A compound represented by formula (1D) wherein $R^1$ is a hydrogen atom;
A compound represented by formula (1D) wherein $R^2$ is a trifluoromethyl group;
A compound represented by formula (1D) wherein $R^2$ is a pentafluoroethyl group;
A compound represented by formula (1D) wherein $R^2$ is a heptafluoropropyl group;
A compound represented by formula (1D) wherein $R^2$ is a heptafluoroisopropyl group;
A compound represented by formula (1D) wherein $A^3$ is N, $R^1$ is a trifluoromethyl group, and $R^2$ is a trifluoromethyl group;
A compound represented by formula (1D) wherein $A^3$ is N, $R^1$ is a hydrogen atom, and $R^2$ is a trifluoromethyl group;
A compound represented by formula (1D) wherein $A^3$ is CH, $R^1$ is a trifluoromethyl group, and $R^2$ is a trifluoromethyl group;
A compound represented by formula (1D) wherein $A^3$ is CH, $R^1$ is a hydrogen atom, and $R^2$ is a trifluoromethyl group;
A compound represented by formula (1D) wherein $A^3$ is N or CH, $R^1$ is a hydrogen atom or a trifluoromethyl group, and $R^2$ is a C1-C3 perfluoroalkyl group;
A compound represented by formula (1D) wherein $A^3$ is N or CH, $R^1$ is a hydrogen atom or a trifluoromethyl group, and $R^2$ is a trifluoromethyl group;
A compound represented by formula (1D) wherein $A^3$ is N, $R^1$ is a hydrogen atom or a trifluoromethyl group, $R^2$ is a C1-C3 perfluoroalkyl group, m is 0 or 1, and n is 0 or 2;
A compound represented by formula (1D) wherein $A^3$ is N, $R^1$ is a hydrogen atom or a trifluoromethyl group, $R^2$ is a trifluoromethyl group, m is 0 or 1, and n is 0 or 2;

A compound represented by formula (1D) wherein A³ is CH, R¹ is a hydrogen atom or a trifluoromethyl group, and R² is a C1-C3 perfluoroalkyl group;

A compound represented by formula (1D) wherein A³ is CH, R¹ is a hydrogen atom or a trifluoromethyl group, and R² is a trifluoromethyl group;

Specific examples of the present compound wherein p is 1 and q is 0 include the compound represented by formula (1A) (hereinafter referred to as "the present compound (1A)"):

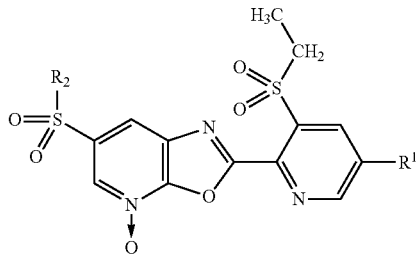

(1A)

wherein R¹ and R² are as defined in the formula (1).

A compound represented by formula (1A) wherein R¹ is a trifluoromethyl group, and R² is a trifluoromethyl group;

A compound represented by formula (1A) wherein R¹ is a chlorine atom, and R² is a trifluoromethyl group;

A compound represented by formula (1A) wherein R¹ is a bromine atom, and R² is a trifluoromethyl group;

A compound represented by formula (1A) wherein R¹ is a hydrogen atom, and R² is a trifluoromethyl group;

Specific examples of the present compound wherein p is 0 and q is 1 include the compound represented by formula (1B) (hereinafter referred to as "the present compound (1B)"):

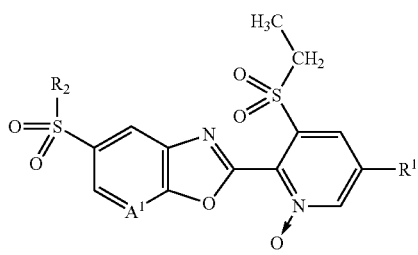

(1B)

wherein A¹ represents N or CH, and R¹ and R² are as defined in the formula (1).

A compound represented by formula (1B) wherein A¹ is N, R¹ is a trifluoromethyl group, and R² is a trifluoromethyl group;

A compound represented by formula (1B) wherein A¹ is N, R¹ is a chlorine atom, and R² is a trifluoromethyl group;

A compound represented by formula (1B) wherein A¹ is N, R¹ is a bromine atom, and R² is a trifluoromethyl group;

A compound represented by formula (1B) wherein A¹ is N, R¹ is a hydrogen atom, and R² is a trifluoromethyl group;

A compound represented by formula (1B) wherein A¹ is CH, R¹ is a trifluoromethyl group, and R² is a trifluoromethyl group;

A compound represented by formula (1B) wherein A¹ is CH, R¹ is a chlorine atom, and R² is a trifluoromethyl group;

A compound represented by formula (1B) wherein A¹ is CH, R¹ is a bromine atom, and R² is a trifluoromethyl group;

A compound represented by formula (1B) wherein A¹ is CH, R¹ is a hydrogen atom, and R² is a trifluoromethyl group;

Specific examples of the present compound wherein p is 1 and q is 1 include the compound represented by formula (1C) (hereinafter referred to as "the present compound (1C)"):

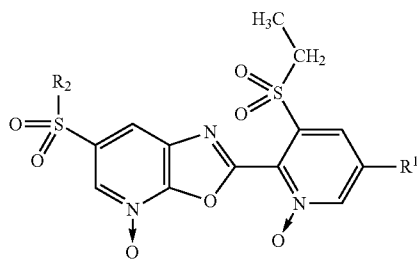

(1C)

wherein R¹ and R² are as defined in the formula (1).

A compound represented by formula (1C) wherein A¹ is N, R¹ is a trifluoromethyl group, and R² is a trifluoromethyl group;

A compound represented by formula (1C) wherein A¹ is N, R¹ is a chlorine atom, and R² is a trifluoromethyl group;

A compound represented by formula (1C) wherein A¹ is N, R¹ is a bromine atom, and R² is a trifluoromethyl group;

A compound represented by formula (1C) wherein A¹ is N, R¹ is a hydrogen atom, and R² is a trifluoromethyl group;

A compound represented by formula (1C) wherein A¹ is CH, R¹ is a trifluoromethyl group, and R² is a trifluoromethyl group;

A compound represented by formula (1C) wherein A¹ is CH, R¹ is a chlorine atom, and R² is a trifluoromethyl group;

A compound represented by formula (1C) wherein A¹ is CH, R¹ is a bromine atom, and R² is a trifluoromethyl group;

A compound represented by formula (1C) wherein A¹ is CH, R¹ is a hydrogen atom, and R² is a trifluoromethyl group;

A compound represented by formula (1) wherein A¹ is CH, R¹ is a hydrogen atom or a trifluoromethyl group, and R² is a trifluoromethyl group;

A compound represented by formula (1) wherein A² is NO, n is 2 and m is 2;

The processes for producing the present compound are described below.

The present compound and the intermediate compound thereof can be produced by, for example, the following (Production process 1) to (Production process 17).

(Production Process 1)

The present compound represented by formula (1) wherein A¹ is N or CH, A² is N, m is 0, and n is 1 or 2 can be produced by oxidizing the present compound wherein A¹ is N or CH, A² is N, m is 0, and n is 0.

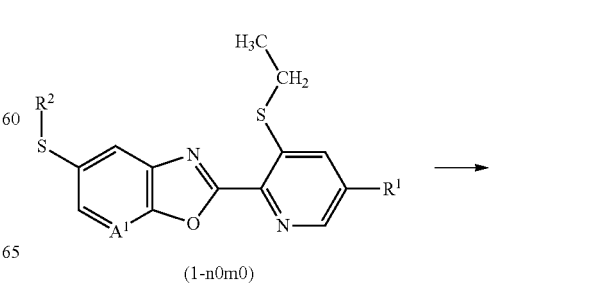

(1-n0m0)

-continued

[Chemical structure (1-n1m0): benzoxazole fused ring system with R²S- substituent, A¹ in ring, connected to a pyridine bearing R¹ and a sulfoxide group S(=O)CH₂CH₃]

(1-n1m0)

[Chemical structure (1-n2m0): benzoxazole fused ring system with R²S- substituent, A¹ in ring, connected to a pyridine bearing R¹ and a sulfone group S(=O)(=O)CH₂CH₃]

(1-n2m0)

wherein $A^1$ represents N or CH, and the other symbols are as defined in the formula (1).

The present compound (1-n1m0) represented by formula (1) wherein $A^1$ is N or CH, $A^2$ is N, m is 0, and n is 1 can be produced by oxidizing the present compound (1-n0m0) wherein $A^1$ is N or CH, $A^2$ is N, m is 0, and n is 0.

The reaction is generally conducted in the presence of a solvent.

Examples of the solvent to be used in the reaction include aliphatic halogenated hydrocarbons such as dichloromethane and chloroform; alcohols such as methanol and ethanol; acetic acid; water; and mixtures thereof.

Examples of the oxidant to be used in the reaction include sodium periodate and m-chloroperbenzoic acid.

The amount of the oxidant to be used in the reaction is generally 1 to 3 moles relative to 1 mole of the present compound (1-n0m0). The amount of the oxidant is preferably 1 to 1.2 moles relative to 1 mole of the present compound (1-n0m0).

The reaction temperature of the reaction is generally within a range of −50° C. to 50° C. The reaction time of the reaction is generally within a range of 0.1 to 12 hours.

After the completion of the reaction, the present compound (1-n1m0) can be isolated by post-treatments, for example, extracting the reaction mixture with an organic solvent, washing the organic layer with, optionally an aqueous solution of a reduction agent (e.g., sodium sulfite and sodium thiosulfate), followed by an aqueous solution of a base (e.g., sodium hydrogen carbonate), and then drying and concentrating the organic layer. The isolated present compound (1-n1m0) can be further purified by chromatography, recrystallization, and the like.

The present compound (1-n2m0) represented by formula (1) wherein $A^1$ is N or CH, $A^2$ is N, m is 0, and n is 2 can be produced by reacting the present compound (1-n1m0) wherein $A^1$ is N or CH, $A^2$ is N, m is 0, and n is 1 in the presence of an oxidant.

The reaction is generally conducted in the presence of a solvent.

Examples of the solvent to be used in the reaction include aliphatic halogenated hydrocarbons such as dichloromethane and chloroform; alcohols such as methanol and ethanol; acetic acid; water; and mixtures thereof.

Examples of the oxidant to be used in the reaction include m-chloroperbenzoic acid, a hydrogen peroxide solution and Oxone®.

The reaction may be conducted in the presence of a catalyst.

Examples of the catalyst to be used in the reaction include tungstate acid, sodium tungstate and potassium tungstate.

The amount of the oxidant to be used in the reaction is generally 1 to 4 moles relative to 1 mole of the present compound (1-n1m0). The amount of the catalyst to be used in the reaction is generally 0.01 to 0.5 moles relative to 1 mole of the present compound (1-n1m0). The amount of the oxidant is preferably 1 to 2 moles relative to 1 mole of the present compound (1-n1m0). The amount of the catalyst is preferably 0.05 to 0.2 moles relative to 1 mole of the present compound (1-n1m0).

The reaction temperature of the reaction is generally within a range of −50° C. to 100° C. The reaction time of the reaction is generally within a range of 0.1 to 12 hours.

After the completion of the reaction, the present compound (1-n2m0) can be isolated by post-treatments, for example, extracting the reaction mixture with an organic solvent, washing the organic layer with, optionally an aqueous solution of a reduction agent (e.g., sodium sulfite and sodium thiosulfate), followed by an aqueous solution of a base (e.g., sodium hydrogen carbonate), and then drying and concentrating the organic layer. The present compound (1-n2m0) can be further purified by chromatography, recrystallization, and the like.

The present compound (1-n2m0) represented by formula (1) wherein $A^1$ is N or CH, $A^2$ is N, m is 0, and n is 2 can be produced in one step (one pot) by reacting the present compound (1-n0m0) wherein $A^1$ is N or CH, $A^2$ is N, m is 0, and n is 0 in the presence of an oxidant.

The reaction is generally conducted in the presence of a solvent.

Examples of the solvent to be used in the reaction include aliphatic halogenated hydrocarbons such as dichloromethane and chloroform; alcohols such as methanol and ethanol; acetic acid; water; and mixtures thereof.

Examples of the oxidant to be used in the reaction include m-chloroperbenzoic acid, a hydrogen peroxide solution and Oxone®.

The reaction may be conducted in the presence of a catalyst.

Examples of the catalyst to be used in the reaction include tungstic acid, sodium tungstate and potassium tungstate.

The amount of the oxidant to be used in the reaction is generally 2 to 5 moles relative to 1 mole of the present compound (1-n0m0). The amount of the catalyst to be used in the reaction is generally 0.01 to 0.5 moles relative to 1 mole of the present compound (1-n0m0). The amount of the oxidant is preferably 2 to 3 moles relative to 1 mole of the present compound (1-n0m0). The amount of the catalyst is preferably 0.05 to 0.2 moles relative to 1 mole of the present compound (1-n0m0).

The reaction temperature of the reaction is generally within a range of 0° C. to 120° C. The reaction time of the reaction is generally within a range of 0.1 to 12 hours.

After the completion of the reaction, the present compound (1-n2m0) can be isolated by post-treatments, for example, extracting the reaction mixture with an organic solvent, washing the organic layer with, optionally an aqueous solution of a reduction agent (e.g., sodium sulfite and sodium thiosulfate), followed by an aqueous solution of a base (e.g., sodium hydrogen carbonate), and then drying and concentrating the organic layer. The isolated present compound (1-n2m0) can be further purified by chromatography, recrystallization, and the like.

(Production Process 2)

The present compounds (1-n2m1) and/or (1-n2m2) represented by formula (1) wherein $A^1$ is N or CH, $A^2$ is N, n is 2, and m is 1 or 2 can be produced by oxidizing the present compound (1-n2m0) wherein $A^1$ is N or CH, $A^2$ is N, n is 2, and m is 0.

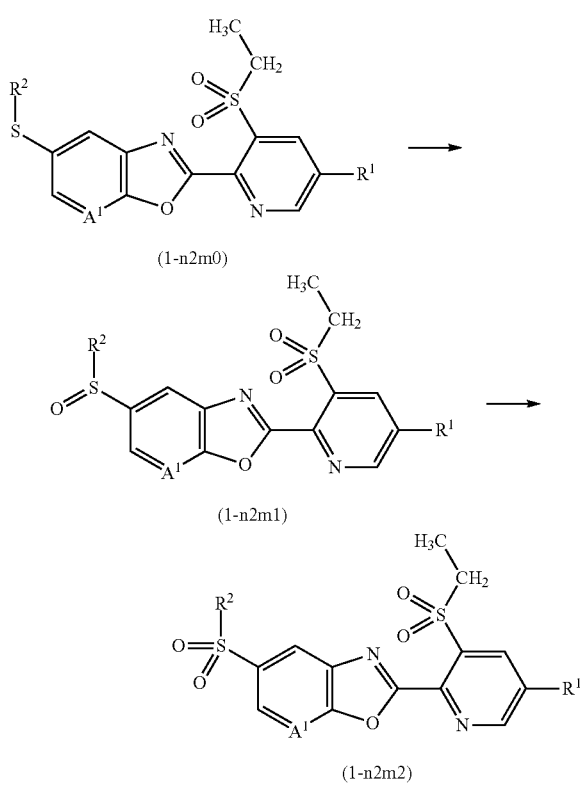

wherein $A^1$ represents N or CH, and the other symbols are as defined in the formula (1).

The present compound (1-n2m1) represented by formula (1) wherein $A^1$ is N or CH, $A^2$ is N, n is 2, and m is 1 can be produced by oxidizing the present compound (1-n2m0) wherein $A^1$ is N or CH, $A^2$ is N, n is 2, and m is 0.

The reaction is generally conducted in the presence of a solvent.

Examples of the solvent to be used in the reaction include aliphatic halogenated hydrocarbons such as dichloromethane and chloroform; alcohols such as methanol and ethanol; acetic acid; water; and mixtures thereof.

Examples of the oxidant to be used in the reaction include sodium periodate, m-chloroperbenzoic acid, a hydrogen peroxide solution and Oxone®.

The reaction may be conducted in the presence of a catalyst.

Examples of the catalyst to be used in the reaction include tungstic acid, sodium tungstate and potassium tungstate.

The amount of the oxidant to be used in the reaction is generally 1 to 3 moles relative to 1 mole of the present compound (1-n2m0). The amount of the catalyst to be used in the reaction is generally 0.01 to 0.5 moles relative to 1 mole of the present compound (1-n2m0). The amount of the oxidant is preferably 1 to 1.2 moles relative to 1 mole of the present compound (1-n2m0). The amount of the catalyst is preferably 0.05 to 0.2 moles relative to 1 mole of the present compound (1-n2m0).

The reaction temperature of the reaction is generally within a range of −50° C. to 100° C. The reaction time of the reaction is generally within a range of 0.1 to 12 hours.

After the completion of the reaction, the present compound (1-n2m1) can be isolated by post-treatments, for example, extracting the reaction mixture with an organic solvent, washing the organic layer with, optionally an aqueous solution of a reduction agent (e.g., sodium sulfite and sodium thiosulfate), followed by an aqueous solution of a base (e.g., sodium hydrogen carbonate), and then drying and concentrating the organic layer. The isolated present compound (1-n2m1) can be further purified by chromatography, recrystallization, and the like.

The present compound (1-n2m2) represented by formula (1) wherein $A^1$ is N or CH, $A^2$ is N, n is 2, and m is 2 can be produced by reacting the present compound (1-n2m1) wherein $A^1$ is N or CH, $A^2$ is N, n is 2, and m is 1 in the presence of an oxidant.

The reaction is generally conducted in the presence of a solvent.

Examples of the solvent to be used in the reaction include aliphatic halogenated hydrocarbons such as dichloromethane and chloroform; alcohols such as methanol and ethanol; acetic acid; water; and mixtures thereof.

Examples of the oxidant to be used in the reaction include m-chloroperbenzoic acid, a hydrogen peroxide solution and Oxone®.

The reaction may be conducted in the presence of a catalyst.

Examples of the catalyst to be used in the reaction include tungstic acid, sodium tungstate and potassium tungstate.

The amount of the oxidant to be used in the reaction is generally 1 to 4 moles relative to 1 mole of the present compound (1-n2m1). The amount of the catalyst to be used in the reaction is generally 0.01 to 0.5 moles relative to 1 mole of the present compound (1-n2m1). The amount of the oxidant is preferably 1 to 2 moles relative to 1 mole of the present compound (1-n2m1). The amount of the catalyst is preferably 0.05 to 0.2 moles relative to 1 mole of the present compound (1-n2m1).

The reaction temperature of the reaction is generally within a range of −50° C. to 100° C. The reaction time of the reaction is generally within a range of 0.1 to 12 hours.

After the completion of the reaction, the present compound (1-n2m2) can be isolated by post-treatments, for example, extracting the reaction mixture with an organic solvent, washing the organic layer with, optionally an aqueous solution of a reduction agent (e.g., sodium sulfite and sodium thiosulfate), followed by an aqueous solution of a base (e.g., sodium hydrogen carbonate), and then drying and concentrating the organic layer. The present compound (1-n2m2) can be further purified by chromatography, recrystallization, and the like.

The present compound (1-n2m2) represented by formula (1) wherein $A^1$ is N or CH, $A^2$ is N, n is 2, and m is 2 can be produced in one step (one pot) by reacting the present compound (1-n2m0) wherein $A^1$ is N or CH, $A^2$ is N, n is 2, and m is 0 in the presence of an oxidant.

The reaction is generally conducted in the presence of a solvent.

Examples of the solvent to be used in the reaction include aliphatic halogenated hydrocarbons such as dichloromethane and chloroform; alcohols such as methanol and ethanol; acetic acid; water; and mixtures thereof.

Examples of the oxidant to be used in the reaction include m-chloroperbenzoic acid, a hydrogen peroxide solution and Oxone®.

The reaction may be conducted in the presence of a catalyst.

Examples of the catalyst to be used in the reaction include tungstic acid, sodium tungstate and potassium tungstate.

The amount of the oxidant to be used in the reaction is generally 2 to 5 moles relative to 1 mole of the present compound (1-n2m0). The amount of the catalyst to be used in the reaction is generally 0.01 to 0.5 moles relative to 1 mole of the present compound (1-n2m0). The amount of the oxidant is preferably 2 to 3 moles relative to 1 mole of the present compound (1-n2m0). The amount of the catalyst is preferably 0.05 to 0.2 moles relative to 1 mole of the present compound (1-n2m0).

The reaction temperature of the reaction is generally within a range of 0° C. to 120° C. The reaction time of the reaction is generally within a range of 0.1 to 12 hours.

After the completion of the reaction, the present compound (1-n2m2) can be isolated by post-treatments, for example, extracting the reaction mixture with an organic solvent, washing the organic layer with, optionally an aqueous solution of a reduction agent (e.g., sodium sulfite and sodium thiosulfate), followed by an aqueous solution of a base (e.g., sodium hydrogen carbonate), and then drying and concentrating the organic layer. The isolated present compound (1-n2m2) can be further purified by chromatography, recrystallization, and the like.

In the production process of the present compound (1-n2m2) wherein $A^1$ is N or CH, $A^2$ is N, n is 2, and m is 2, the present compounds (1A) and/or (1B) and/or (1C) may be also produced.

(Production Process 3)

The present compounds (1-n2m1) and/or (1-n2m2) represented by formula (1) wherein $A^1$ is N or CH, $A^2$ is N, n is 2, and m is 1 or 2 can be produced by oxidizing the present compound (1-n0m0) wherein $A^1$ is N or CH, $A^2$ is N, n is 0, and m is 0.

The reaction is generally conducted in the presence of a solvent.

Examples of the solvent to be used in the reaction include aliphatic halogenated hydrocarbons such as dichloromethane and chloroform; alcohols such as methanol and ethanol; acetic acid; water; and mixtures thereof.

Examples of the oxidant to be used in the reaction include m-chloroperbenzoic acid, a hydrogen peroxide solution and Oxone®.

The reaction may be conducted in the presence of a catalyst.

Examples of the catalyst to be used in the reaction include tungstic acid, sodium tungstate and potassium tungstate.

The amount of the oxidant to be used in the reaction is generally 3 to 10 moles relative to 1 mole of the present compound (1-n0m0). The amount of the catalyst to be used in the reaction is generally 0.01 to 0.5 moles relative to 1 mole of the present compound (1-n0m0). The amount of the oxidant is preferably 3 to 5 moles relative to 1 mole of the present compound (1-n0m0). The amount of the catalyst is preferably 0.05 to 0.2 moles relative to 1 mole of the present compound (1-n0m0).

The reaction temperature of the reaction is generally within a range of 0° C. to 120° C. The reaction time of the reaction is generally within a range of 0.1 to 12 hours.

After the completion of the reaction, the present compound (1-n2m1) can be isolated by post-treatments, for example, extracting the reaction mixture with an organic

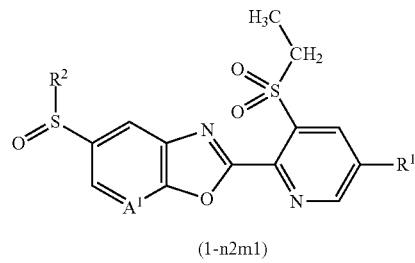

(1-n2m1)

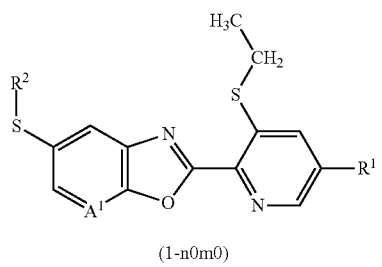

(1-n0m0)

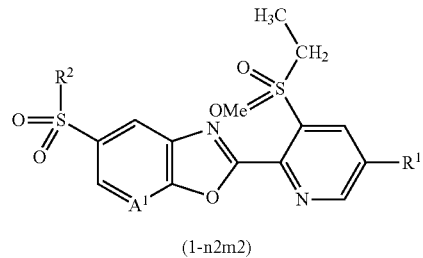

(1-n2m2)

wherein $A^1$ represents N or CH, and the other symbols are as defined in the formula (1).

The present compound (1-n2m1) represented by formula (1) wherein $A^1$ is N or CH, $A^2$ is N, n is 2, and m is 1 can be produced in one step (one pot) by reacting the present compound (1-n0m0) wherein $A^1$ is N or CH, $A^2$ is N, n is 0, and m is 0 in the presence of an oxidant.

solvent, washing the organic layer with, optionally an aqueous solution of a reduction agent (e.g., sodium sulfite and sodium thiosulfate), followed by an aqueous solution of a base (e.g., sodium hydrogen carbonate), and then drying and concentrating the organic layer. The isolated present compound (1-n2m1) can be further purified by chromatography, recrystallization, and the like.

The present compound (1-n2m2) represented by formula (1) wherein $A^1$ is N or CH, $A^2$ is N, n is 2, and m is 2 can be produced in one step (one pot) by reacting the present compound (1-n0m0) wherein $A^1$ is N or CH, $A^2$ is N, n is 0, and m is 0 in the presence of an oxidant.

The reaction is generally conducted in the presence of a solvent.

Examples of the solvent to be used in the reaction include aliphatic halogenated hydrocarbons such as dichloromethane and chloroform; alcohols such as methanol and ethanol; acetic acid; water; and mixtures thereof.

Examples of the oxidant to be used in the reaction include m-chloroperbenzoic acid, a hydrogen peroxide solution and Oxone®.

The reaction may be conducted in the presence of a catalyst.

Examples of the catalyst to be used in the reaction include tungstic acid, sodium tungstate and potassium tungstate.

The amount of the oxidant to be used in the reaction is generally 4 to 15 moles relative to 1 mole of the present compound (1-n0m0). The amount of the catalyst to be used in the reaction is generally 0.01 to 0.5 moles relative to 1 mole of the present compound (1-n0m0). The amount of the oxidant is preferably 4 to 5 moles relative to 1 mole of the present compound (1-n0m0). The amount of the catalyst is preferably 0.05 to 0.2 moles relative to 1 mole of the present compound (1-n0m0).

The reaction temperature of the reaction is generally within a range of 0° C. to 120° C. The reaction time of the reaction is generally within a range of 0.1 to 12 hours.

After the completion of the reaction, the present compound (1-n2m2) can be isolated by post-treatments, for example, extracting the reaction mixture with an organic solvent, washing the organic layer with, optionally an aqueous solution of a reduction agent (e.g., sodium sulfite and sodium thiosulfate), followed by an aqueous solution of a base (e.g., sodium hydrogen carbonate), and then drying and concentrating the organic layer. The isolated present compound (1-n2m2) can be further purified by chromatography, recrystallization, and the like.

In the production process of the present compound (1-n2m2) wherein $A^1$ is N or CH, $A^2$ is N, n is 2, and m is 2, the present compounds (1A) and/or (1B) and/or (1C) may be also produced.

(Production Process 4-1)

The present compound (1A) is can be produced by oxidizing the present compound (1-n2m2) wherein $A^1$ is N, $A^2$ is N, n is 2, and m is 2.

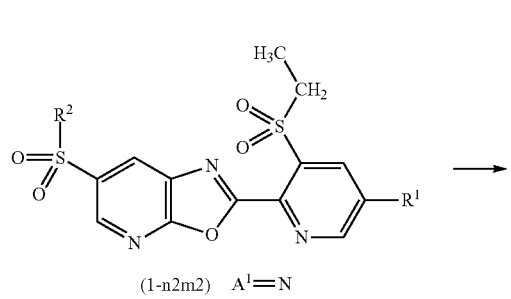

(1-n2m2)   $A^1$=N

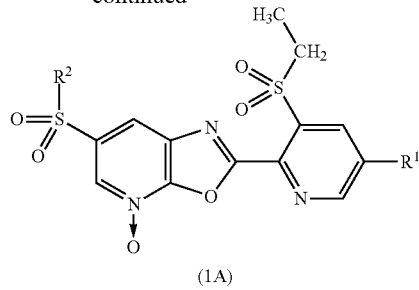

(1A)

wherein the symbols are as defined in the formula (1).

The reaction is generally conducted in the presence of a solvent.

Examples of the solvent to be used in the reaction include aliphatic halogenated hydrocarbons such as dichloromethane and chloroform; alcohols such as methanol and ethanol; acetic acid; water; and mixtures thereof.

Examples of the oxidant to be used in the reaction include m-chloroperbenzoic acid, a hydrogen peroxide solution and Oxone®.

The reaction may be conducted in the presence of a catalyst.

Examples of the catalyst to be used in the reaction include tungstic acid, sodium tungstate and potassium tungstate.

The amount of the oxidant to be used in the reaction is generally 1 to 10 moles relative to 1 mole of the present compound (1-n2m2). The amount of the catalyst to be used in the reaction is generally 0.01 to 0.5 moles relative to 1 mole of the present compound (1-n2m2). The amount of the oxidant is preferably 2 to 5 moles relative to 1 mole of the present compound (1-n2m2). The amount of the catalyst is preferably 0.05 to 0.2 moles relative to 1 mole of the present compound (1-n2m2).

The reaction temperature of the reaction is generally within a range of 20° C. to 120° C. The reaction time of the reaction is generally within a range of 0.1 to 48 hours.

After the completion of the reaction, the present compound (1A) can be isolated by post-treatments, for example, extracting the reaction mixture with an organic solvent, washing the organic layer with, optionally an aqueous solution of a reduction agent (e.g., sodium sulfite and sodium thiosulfate), followed by an aqueous solution of a base (e.g., sodium hydrogen carbonate), and then drying and concentrating the organic layer. The isolated present compound (1A) can be further purified by chromatography, recrystallization, and the like.

In the production process of the present compound (1A), the present compounds (1B) and/or (1C) may be also produced.

(Production Process 4-2)

The present compound (1B) is can be produced by oxidizing the present compound (1-n2m2) wherein $A^1$ is N or CH, $A^2$ is N, n is 2, and m is 2.

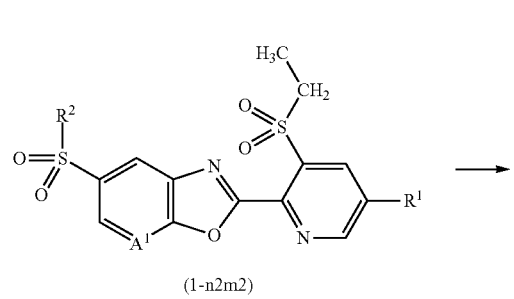

(1-n2m2)

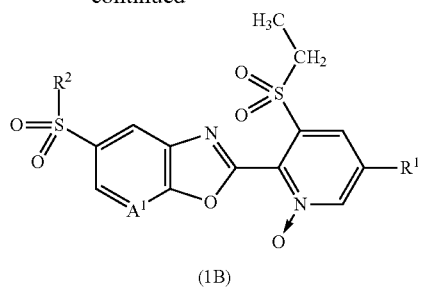

(1B)

wherein A¹ represents N or CH, and the other symbols are as defined in the formula (1).

The reaction is generally conducted in the presence of a solvent.

Examples of the solvent to be used in the reaction include aliphatic halogenated hydrocarbons such as dichloromethane and chloroform; alcohols such as methanol and ethanol; acetic acid; water; and mixtures thereof.

Examples of the oxidant to be used in the reaction include m-chloroperbenzoic acid, a hydrogen peroxide solution and Oxone®.

The reaction may be conducted in the presence of a catalyst.

Examples of the catalyst to be used in the reaction include tungstic acid, sodium tungstate and potassium tungstate.

The amount of the oxidant to be used in the reaction is generally 1 to 10 moles relative to 1 mole of the present compound (1-n2m2). The amount of the catalyst to be used in the reaction is generally 0.01 to 0.5 moles relative to 1 mole of the present compound (1-n2m2). The amount of the oxidant is preferably 2 to 5 moles relative to 1 mole of the present compound (1-n2m2). The amount of the catalyst is preferably 0.05 to 0.2 moles relative to 1 mole of the present compound (1-n2m2).

The reaction temperature of the reaction is generally within a range of 20° C. to 120° C. The reaction time of the reaction is generally within a range of 0.1 to 48 hours.

After the completion of the reaction, the present compound (1B) can be isolated by post-treatments, for example, extracting the reaction mixture with an organic solvent, washing the organic layer with, optionally an aqueous solution of a reduction agent (e.g., sodium sulfite and sodium thiosulfate), followed by an aqueous solution of a base (e.g., sodium hydrogen carbonate), and then drying and concentrating the organic layer. The isolated present compound (1B) can be further purified by chromatography, recrystallization, and the like.

In the production process of the present compound (1B), the present compounds (1A) and/or (1C) may be also produced.

(Production Process 4-3)

The present compound (1C) can be produced by oxidizing the present compound (1-n2m2) wherein A¹ is N, A² is N, n is 2, and m is 2.

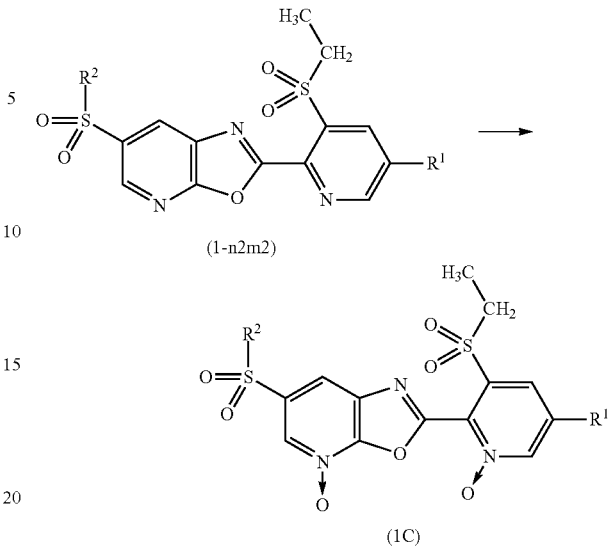

wherein the symbols are as defined in the formula (1).

The reaction is generally conducted in the presence of a solvent.

Examples of the solvent to be used in the reaction include aliphatic halogenated hydrocarbons such as dichloromethane and chloroform; alcohols such as methanol and ethanol; acetic acid; water; and mixtures thereof.

Examples of the oxidant to be used in the reaction include m-chloroperbenzoic acid, a hydrogen peroxide solution and Oxone®.

The reaction may be conducted in the presence of a catalyst.

Examples of the catalyst to be used in the reaction include tungstic acid, sodium tungstate and potassium tungstate.

The amount of the oxidant to be used in the reaction is generally 2 to 20 moles relative to 1 mole of the present compound (1-n2m2). The amount of the catalyst to be used in the reaction is generally 0.01 to 0.5 moles relative to 1 mole of the present compound (1-n2m2). The amount of the oxidant is preferably 3 to 10 moles relative to 1 mole of the present compound (1-n2m2). The amount of the catalyst is preferably 0.05 to 0.2 moles relative to 1 mole of the present compound (1-n2m2).

The reaction temperature of the reaction is generally within a range of 50° C. to 150° C. The reaction time of the reaction is generally within a range of 1 to 48 hours.

After the completion of the reaction, the present compound (1C) can be isolated by post-treatments, for example, extracting the reaction mixture with an organic solvent, washing the organic layer with, optionally an aqueous solution of a reduction agent (e.g., sodium sulfite and sodium thiosulfate), followed by an aqueous solution of a base (e.g., sodium hydrogen carbonate), and then drying and concentrating the organic layer. The isolated present compound (1C) can be further purified by chromatography, recrystallization, and the like.

In the production process of the present compound (1C), the present compounds (1A) and/or (1B) may be also produced.

(Production Process 5-1)

The present compound wherein A¹ is N or CH, and A² is N can be produced by reacting the intermediate compound (M1) and the intermediate compound (M2) to obtain the intermediate compound (M4), and then subjecting the resulting intermediate compound (M4) to intramolecular condensation.

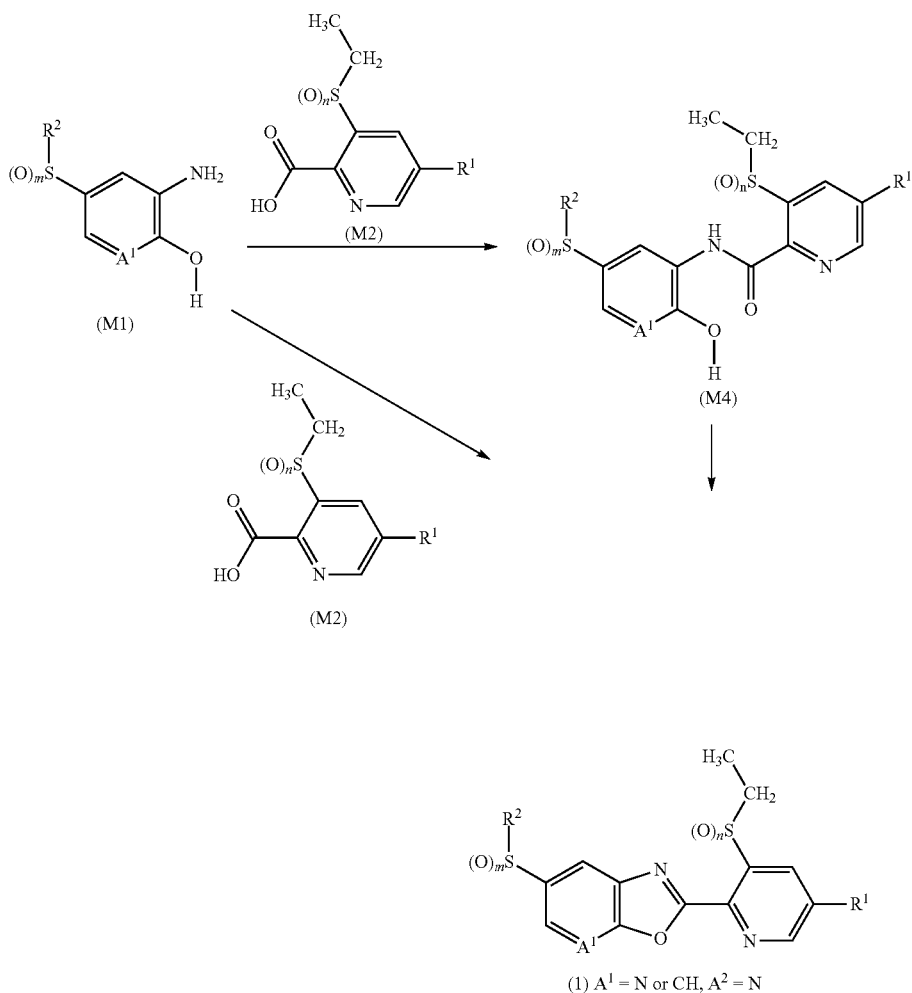

(1) A¹ = N or CH, A² = N wherein $A^1$ represents N or CH, and the other symbols are as defined in the formula (1).

The intermediate compound (M4) can be produced by reacting the intermediate compound (M1) and the intermediate compound (M2) in the presence of a condensing agent.

The reaction is generally conducted in the presence of a solvent. Examples of the solvent to be used in the reaction include ethers such as 1,4-dioxane, diethyl ether, tetrahydrofuran (hereinafter referred to as "THF"), and tert-butylmethyl ether; halogenated hydrocarbons such as dichloromethane, chloroform, carbon tetrachloride, 1,2-dichloroethane, and chlorobenzene; aromatic hydrocarbons such as toluene, benzene, and xylene; esters such as ethyl acetate, and butyl acetate; nitriles such as acetonitrile; aprotic polar solvents such as N,N-dimethylformamide (hereinafter referred to as "DMF"), N-methylpyrrolidone (hereinafter referred to as "NMP"), 1,3-dimethyl-2-imidazolidinone, and dimethylsulfoxide (hereinafter referred to as "DMSO"); nitrogen-containing aromatic compounds such as pyridine and quinoline; and mixtures thereof.

Examples of the condensing agent to be used in the reaction include carbodiimides such as 1-ethyl-3-(3-dimethylaminopropyl)carbodiimide hydrochloride (hereinafter referred to as "EDCI hydrochloride") and 1,3-dicyclohexyl carbodiimide.

The reaction may be conducted in the presence of a catalyst.

Examples of the catalyst to be used in the reaction include 1-hydroxybenzotriazol (hereinafter referred to as "HOBt").

The amount of the intermediate compound (M2) to be used in the reaction is generally 0.5 to 2 moles relative to 1 mole of the intermediate compound (M1). The amount of the condensing agent to be used in the reaction is generally 1 to 5 moles relative to 1 mole of the intermediate compound (M1). The amount of the catalyst to be used in the reaction is generally 0.01 to 1 moles relative to 1 mole of the intermediate compound (M1).

The reaction temperature of the reaction is generally within a range of 0° C. to 120° C. The reaction time of the reaction is generally within a range of 0.1 to 24 hours.

After the completion of the reaction, the intermediate compound (M4) can be isolated by post-treatments, for example, pouring water to the reaction mixture, extracting the reaction mixture with an organic solvent, and concentrating the organic layer; pouring water to the reaction mixture, and collecting a solid by filtration; or collecting a solid formed in the reaction mixture by filtration. The isolated intermediate compound (M4) can be further purified by chromatography, recrystallization, and the like.

The present compound (1) wherein $A^1$ is N or CH, and $A^2$ is N can be produced by subjecting the intermediate compound (M4) to intramolecular condensation.

The reaction is generally conducted in the presence of a solvent. Examples of the solvent to be used in the reaction include ethers such as 1,4-dioxane, diethyl ether, THF, and tert-butylmethyl ether; halogenated hydrocarbons such as dichloromethane, chloroform, carbon tetrachloride, 1,2-dichloroethane, and chlorobenzene; aromatic hydrocarbons such as toluene, benzene, and xylene; esters such as ethyl acetate, and butyl acetate; nitriles such as acetonitrile; aprotic polar solvents such as DMF, NMP, 1,3-dimethyl-2-imidazolidinone, and DMSO; nitrogen-containing aromatic compounds such as pyridine and quinoline; and mixtures thereof.

The reaction may be conducted in the presence of a condensing agent, an acid, a base or a chlorinating agent.

Examples of the condensing agent to be used in the reaction include acetic acid anhydride, trifluoroacetic acid anhydride, EDCI hydrochloride, a mixture of triphenyl phosphine, a base, and carbon tetrachloride or carbon tetrabromide, a mixture of triphenyl phosphine and azodiesters such as diethyl azodicarboxylate.

Examples of the acid to be used in the reaction include sulfonic acids such as para-toluenesulfonic acid and methanesulfonic acid; carboxylic acids such as acetic acid; sulfuric acid; phosphoric acid; polyphosphoric acid; and the like.

Examples of the base to be used in the reaction include nitrogen-containing heterocyclic compounds such as pyridine, picoline, 2,6-lutidine, 1,8-diazabicyclo[5.4.0]-7-undecene (hereinafter referred to as "DBU"), and 1,5-diazabicyclo[4.3.0]-5-nonene; tertiary amines such as triethylamine and N,N-diisopropylethylamine; inorganic bases such as tripotassium phosphate, potassium carbonate, and sodium hydride.

Examples of the chlorinating agent to be used in the reaction include phosphorous oxychloride; and the like.

When a condensing agent is used in the reaction, the amount of the condensing agent is generally 1 to 5 moles relative to 1 mole of the intermediate compound (M4). When an acid is used in the reaction, the amount of the acid is generally 0.1 to 5 moles relative to 1 mole of the intermediate compound (M4). When a base is used in the reaction, the amount of the base is generally 1 to 5 moles relative to 1 mole of the intermediate compound (M4). When a chlorinating agent is used in the reaction, the amount of the chlorinating agent is generally 1 to 5 moles relative to 1 mole of the intermediate compound (M4).

The reaction temperature of the reaction is generally within a range of 0° C. to 200° C. The reaction time of the reaction is generally within a range of 0.1 to 24 hours.

After the completion of the reaction, the present compound (1) wherein $A^1$ is N or CH, and $A^2$ is N can be isolated by post-treatments, for example, pouring water to the reaction mixture, extracting the reaction mixture with an organic solvent, and concentrating the organic layer; pouring water to the reaction mixture, and collecting a solid by filtration; or collecting a solid formed in the reaction mixture by filtration. The isolated present compound (1) wherein $A^1$ is N or CH, and $A^2$ is N can be further purified by recrystallization, chromatography, and the like.

The present compound (1) wherein $A^1$ is N or CH, and $A^2$ is N can be also produced in one step (one pot) by reacting the intermediate compound (M1) with the intermediate compound (M2) in the presence of a condensing agent.

The reaction is generally conducted in the presence of a solvent. Examples of the solvent to be used in the reaction include ethers such as 1,4-dioxane, diethyl ether, THF, and tert-butylmethyl ether; halogenated hydrocarbons such as dichloromethane, chloroform, carbon tetrachloride, 1,2-dichloroethane, and chlorobenzene; aromatic hydrocarbons such as toluene, benzene, and xylene; esters such as ethyl acetate, and butyl acetate; nitriles such as acetonitrile; aprotic polar solvents such as DMF, NMP, 1,3-dimethyl-2-imidazolidinone, and DMSO; nitrogen-containing aromatic compounds such as pyridine and quinoline; and mixtures thereof.

Examples of the dehydrating condensing agent to be used in the reaction include carbodiimides such as EDCI hydrochloride, 1,3-dicyclohexyl carbodiimide, and boric acid.

The reaction may be conducted in the presence of a catalyst.

Examples of the catalyst to be used in the reaction include 1-hydroxybenzotriazol.

The amount of the intermediate compound (M2) to be used in the reaction is generally 0.5 to 2 moles relative to 1 mole of the intermediate compound (M1). The amount of the condensing agent to be used in the reaction is generally 1 to 5 moles relative to 1 mole of the intermediate compound (M1). The amount of the catalyst to be used in the reaction is generally 0.01 to 1 moles relative to 1 mole of the intermediate compound (M1).

The reaction temperature of the reaction is generally within a range of 0° C. to 200° C. The reaction time of the reaction is generally within a range of 0.1 to 24 hours.

After the completion of the reaction, the present compound (1) wherein $A^1$ is N or CH, and $A^2$ is N can be isolated by post-treatments, for example, pouring water to the reaction mixture, extracting the reaction mixture with an organic solvent, and concentrating the organic layer; pouring water to the reaction mixture, and collecting a solid by filtration; or collecting a solid formed in the reaction mixture by filtration. The isolated present compound (1) wherein $A^1$ is N or CH, and $A^2$ is N can be further purified by recrystallization, chromatography, and the like.

(Production Process 5-2)

The present compound wherein $A^1$ is N or CH, and $A^2$ is N can be produced by reacting the intermediate compound (M1) and the intermediate compound (M3) to obtain the intermediate compound (M4), then subjecting the resulting intermediate compound (M4) to intramolecular condensation.

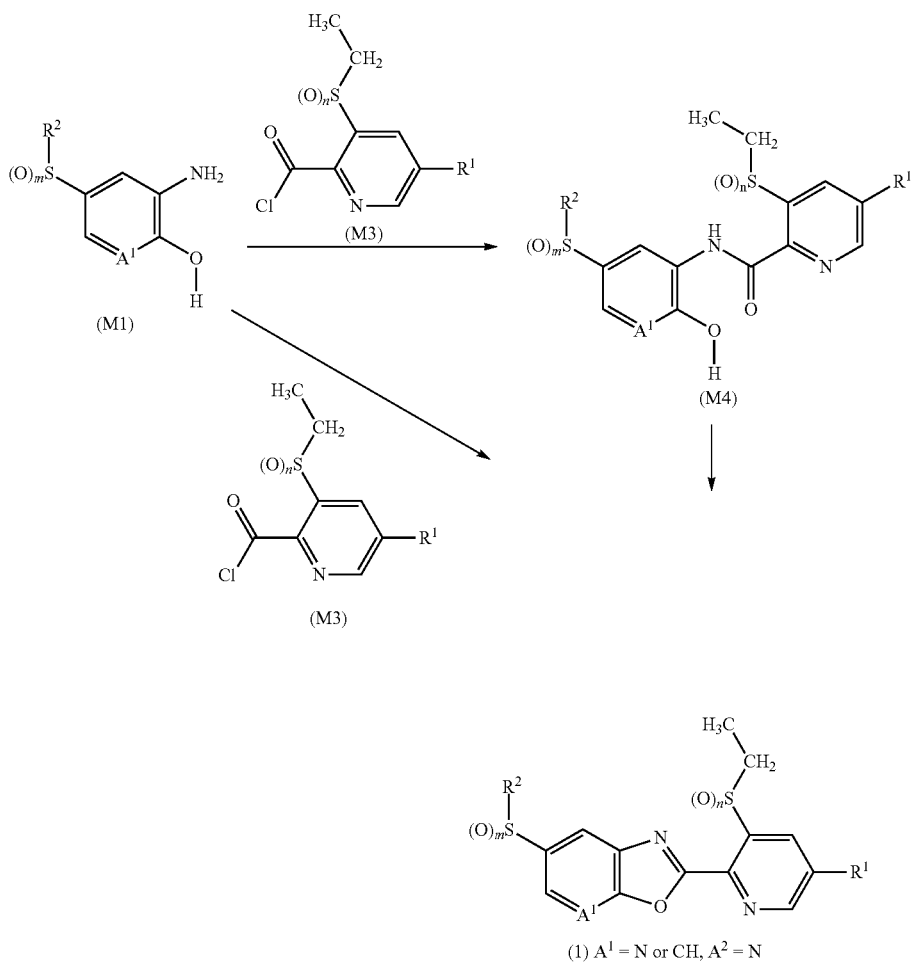

wherein $A^1$ represents N or CH, and the other symbols are as defined in the formula (1).

The intermediate compound (M4) can be produced by reacting the intermediate compound (M1) and the intermediate compound (M3).

The reaction is generally conducted in the presence of a solvent.

Examples of the solvent to be used in the reaction include ethers such as THF, ethylene glycol dimethyl ether, tert-butylmethyl ether, and 1,4-dioxane; aliphatic hydrocarbons such as hexane, heptane, and octane; aromatic hydrocarbons such as toluene and xylene; halogenated hydrocarbons such as chlorobenzene; esters such as ethyl acetate and butyl acetate; nitriles such as acetonitrile; aprotic polar solvents such as DMF, NMP, and DMSO; and mixtures thereof.

The reaction may be conducted in the presence of a base.

Examples of the base to be used in the reaction include alkali metal carbonates such as sodium carbonate and potassium carbonate; tertiary amines such as triethylamine and N,N-diisopropylethylamine; and nitrogen-containing aromatic compounds such as pyridine and 4-dimethylaminopyridine.

The amount of the intermediate compound (M3) to be used in the reaction is generally 1 to 3 moles relative to 1 mole of the intermediate compound (M1). The amount of the base to be used in the reaction is generally 1 to 10 moles relative to 1 mole of the intermediate compound (M1).

The reaction temperature of the reaction is generally within a range of −20° C. to 100° C. The reaction time of the reaction is generally within a range of 0.1 to 24 hours.

After the completion of the reaction, the intermediate compound (M4) can be isolated by post-treatments, for example, pouring water to the reaction mixture, extracting the reaction mixture with an organic solvent, and drying and concentrating the organic layer. The isolated intermediate compound (M4) can be further purified by chromatography, recrystallization, and the like.

The present compound (1) wherein $A^1$ is N or CH, and $A^2$ is N can be produced by subjecting the intermediate compound (M4) to intramolecular condensation in accordance with Production process 5-1.

The isolated present compound (1) wherein $A^1$ is N or CH, and $A^2$ is N can be also produced in one step (one pot) by reacting the intermediate compound (M1) with the intermediate compound (M3) in the presence of a condensing agent.

The reaction is generally conducted in the presence or absence of a solvent.

Examples of the solvent to be used in the reaction include ethers such as THF, ethylene glycol dimethyl ether, tert-butylmethyl ether, and 1,4-dioxane; aliphatic hydrocarbons such as hexane, heptane, and octane; aromatic hydrocarbons such as toluene and xylene; halogenated hydrocarbons such as chlorobenzene; esters such as ethyl acetate and butyl acetate; nitriles such as acetonitrile; aprotic polar solvents such as DMF, NMP, and DMSO; and mixtures thereof.

The reaction may be conducted in the presence of a base.

Examples of the base to be used in the reaction include alkali metal carbonates such as sodium carbonate and potassium carbonate; tertiary amines such as triethylamine and N,N-diisopropylethylamine; and nitrogen-containing aromatic compounds such as pyridine and 4-dimethylaminopyridine.

The amount of the intermediate compound (M3) to be used in the reaction is generally 1 to 3 moles relative to 1 mole of the intermediate compound (M1). The amount of the base to be used in the reaction is generally 1 to 10 moles relative to 1 mole of the intermediate compound (M1).

The reaction temperature of the reaction is generally within a range of 20° C. to 200° C. The reaction time of the reaction is generally within a range of 0.1 to 24 hours.

After the completion of the reaction, the present compound (1) wherein $A^1$ is N or CH, and $A^2$ is N can be isolated by post-treatments, for example, pouring water to the reaction mixture, extracting the reaction mixture with an organic solvent, and drying and concentrating the organic layer. The isolated present compound (1) wherein $A^1$ is N or CH, and $A^2$ can be further purified by chromatography, recrystallization, and the like.

(Production Process 6)

The isolated present compound (1) wherein $A^1$ is N or CH, and $A^2$ is N can be also produced by reacting the intermediate compound (M1) with the intermediate compound (M5) in the presence of an oxidant.

The reaction is generally conducted in the presence of a solvent. Examples of the solvent to be used in the reaction include alcohols such as methanol and ethanol; ethers such as 1,4-dioxane, diethyl ether, THF, and tert-butylmethyl ether; halogenated hydrocarbons such as dichloromethane, chloroform, carbon tetrachloride, 1,2-dichloroethane, and chlorobenzene; aromatic hydrocarbons such as toluene, benzene, and xylene; esters such as ethyl acetate, and butyl acetate; nitriles such as acetonitrile; aprotic polar solvents such as DMF, NMP, 1,3-dimethyl-2-imidazolidinone, and DMSO; nitrogen-containing aromatic compounds such as pyridine and quinoline; and mixtures thereof.

Examples of the oxidant to be used in the reaction include oxygen, copper (II) chloride, 2,3-dichloro-5,6-dicyanobenzoquinone (hereinafter referred to as "DDQ"); and the like.

The reaction may be conducted in the presence of an acid.

Examples of the acid to be used in the reaction include sulfonic acids such as para-toluenesulfonic acid; carboxylic acids such as acetic acid; polyphosphoric acid; and the like.

The reaction may be conducted in the presence of a sulfite.

Examples of the sulfite to be used in the reaction include sodium hydrogen sulfite, and disodium sulfite.

The amount of the intermediate compound (M5) to be used in the reaction is generally 1 to 2 moles relative to 1 mole of the intermediate compound (M1). The amount of the oxidant to be used in the reaction is generally 1 to 5 moles relative to 1 mole of the intermediate compound (M1). The amount of the acid to be used in the reaction is generally 0.1 to 2 moles relative to 1 mole of the intermediate compound (M1). The amount of the sulfite to be used in the reaction is generally 1 to 5 moles relative to 1 mole of the intermediate compound (M1).

The reaction temperature of the reaction is generally within a range of 0° C. to 200° C.

After the completion of the reaction, the present compound (1) wherein $A^1$ is N or CH, and $A^2$ is N can be isolated by post-treatments, for example, pouring water to the reaction mixture, extracting the reaction mixture with an organic solvent, and concentrating the organic layer; pouring water to the reaction mixture, and collecting a solid by filtration; or collecting a solid formed in the reaction mixture by filtration. The isolated present compound (1) wherein $A^1$ is N or CH, and $A^2$ is N can be further purified by recrystallization, chromatography, and the like.

(Production Process 7)

The present compound (1-n0) wherein $A^1$ is N or CH, $A^2$ is N, and n is 0 can be also produced by reacting the intermediate compound (M6) with the intermediate compound (M7) in the presence of a base.

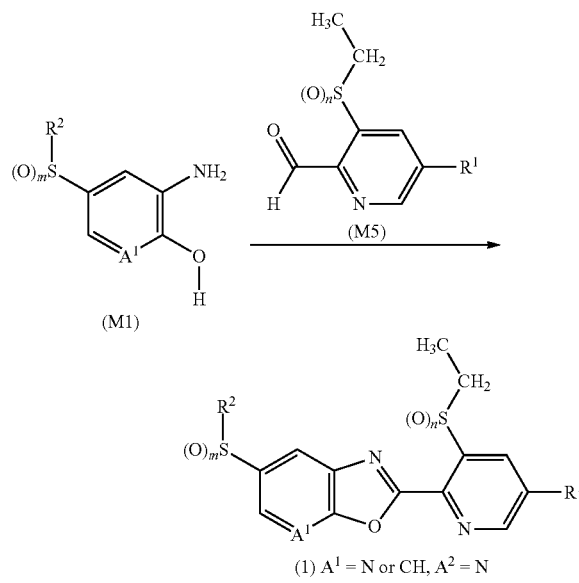

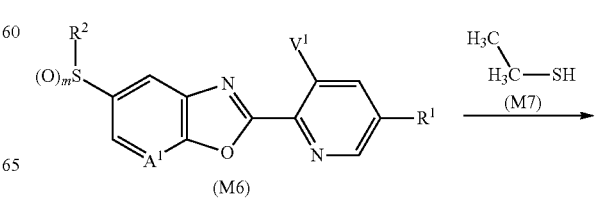

wherein $A^1$ represents N or CH, and the other symbols are as defined in the formula (1).

-continued

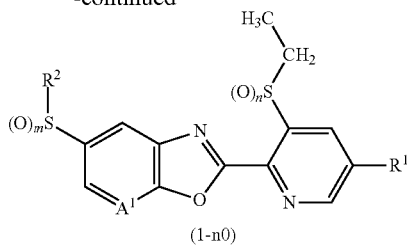

(1-n0)

wherein $A^1$ represents N or CH, $V^1$ represents a halogen atom and the other symbols are as defined in the formula (1).

The reaction is generally conducted in the presence of a solvent.

Examples of the solvent to be used in the reaction include ethers such as THF, ethylene glycol dimethyl ether, tert-butylmethyl ether, and 1,4-dioxane; aromatic hydrocarbons such as toluene and xylene; nitriles such as acetonitrile; aprotic polar solvents such as DMF, NMP, and DMSO; water; and mixtures thereof.

Examples of the base to be used in the reaction include alkali metal carbonates such as sodium carbonate and potassium carbonate; and alkali metal hydrides such as sodium hydride.

The amount of the intermediate compound (M7) to be used in the reaction is generally 1 to 10 moles relative to 1 mole of the intermediate compound (M6). The amount of the base to be used in the reaction is generally 1 to 10 moles relative to 1 mole of the intermediate compound (M6).

The reaction temperature of the reaction is generally within a range of −50° C. to 100° C. The reaction time of the reaction is generally within a range of 0.1 to 12 hours.

After the completion of the reaction, the present compound (1-n0) wherein $A^1$ is N or CH, $A^2$ is N and n is 0 can be isolated by post-treatments, for example, extracting the reaction mixture with an organic solvent, and drying and concentrating the organic layer. The isolated present compound (1-n0) wherein $A^1$ is N or CH, $A^2$ is N and n is 0 can be further purified by chromatography, recrystallization, and the like.

In the reaction, $V^1$ is preferably a fluorine atom or a chlorine atom.

(Production Process 8-1)

The intermediate compound (M6) can be produced by reacting the intermediate compound (M1) with the intermediate compound (M8) to obtain the intermediate compound (M10), and then subjecting the resulting intermediate compound (M10) to intramolecular condensation.

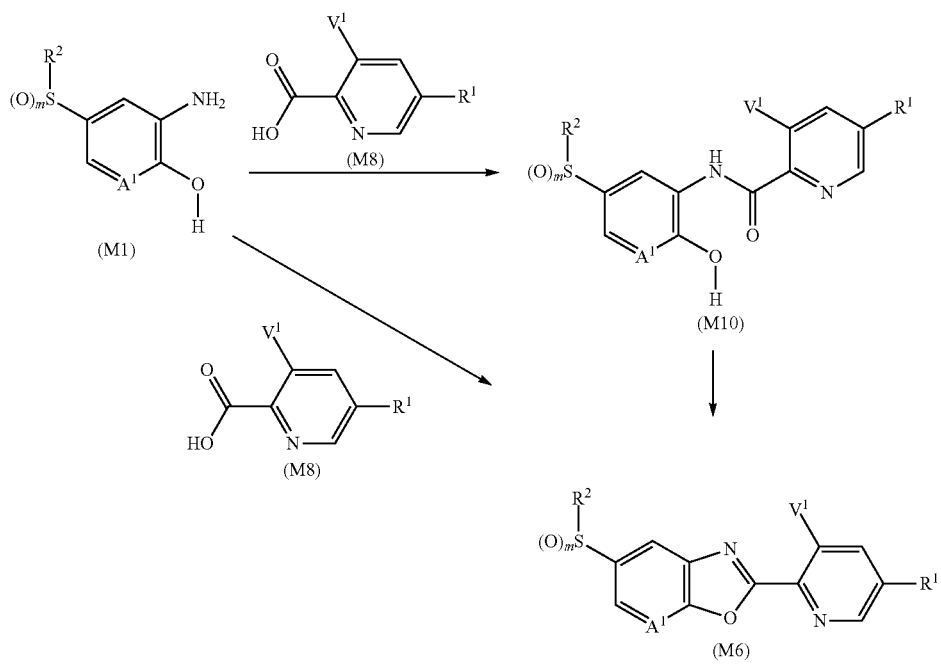

wherein $A^1$ represents N or CH, $V^1$ represents a halogen atom and the other symbols are as defined in the formula (1).

The intermediate compound (M10) can be produced in the same manner as in Production process 5-1 by using the intermediate compound (M8) instead of the intermediate compound (M2).

The intermediate compound (M6) can be produced in the same manner as in Production process 5-1 or 5-2 by using the intermediate compound (M10) instead of the intermediate compound (M4).

The intermediate compound (M6) can be also produced in one step (one pot) in accordance with Production process 5-1 by using the intermediate compound (M8) instead of the intermediate compound (M2).

In the reaction, $V^1$ is preferably a fluorine atom or a chlorine atom.

(Production Process 8-2)

The intermediate compound (M6) can be produced by reacting the intermediate compound (M1) and the intermediate compound (M9) to obtain the intermediate compound (M10), and then subjecting the resulting intermediate compound (M10) to intramolecular condensation.

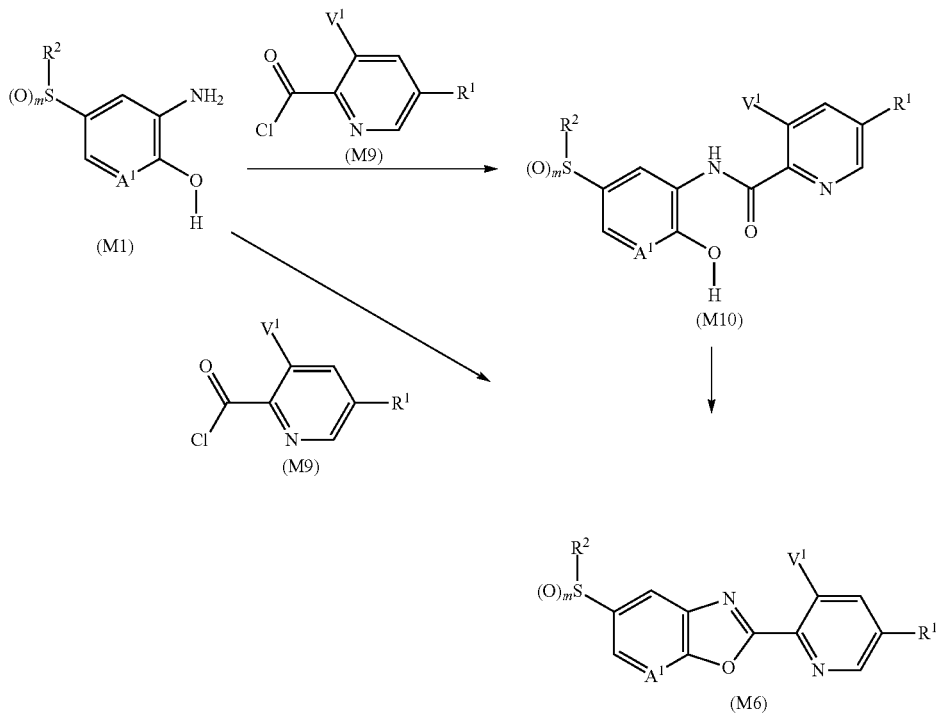

wherein $A^1$ represents N or CH, $V^1$ represents a halogen atom and the other symbols are as defined in the formula (1).

The intermediate compound (M10) can be produced in the same manner as in Production process 5-2 by using the intermediate compound (M9) instead of the intermediate compound (M3).

The intermediate compound (M6) can be produced in the same manner as in Production process 5-1 or 5-2 by using the intermediate compound (M10) instead of the intermediate compound (M4).

The intermediate compound (M6) can be also produced in one step (one pot) in accordance with Production process 5-2 by using the intermediate compound (M9) instead of the intermediate compound (M2).

In the reaction, $V^1$ is preferably a fluorine atom or a chlorine atom.

(Production Process 9)

The intermediate compound (M6) can be produced by reacting the intermediate compound (M1) and the intermediate compound (M11).

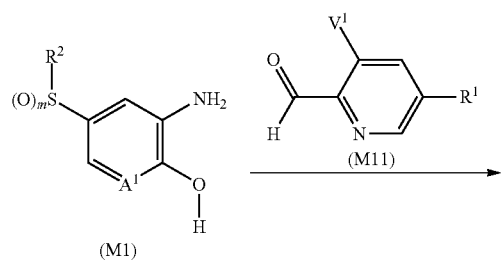

-continued

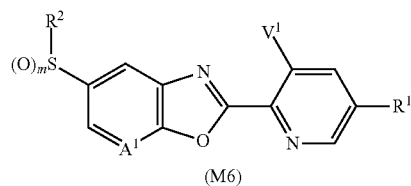

wherein $A^1$ represents N or CH, and the other symbols are as defined in the formula (1).

The intermediate compound (M6) can be produced in the same manner as in Production process 6 by using the intermediate compound (M11) instead of the intermediate compound (M5).

(Production Process 10)

The intermediate compound (M4-n0) wherein n is 0 can be produced by reacting the intermediate compound (M10) and the intermediate compound (M7).

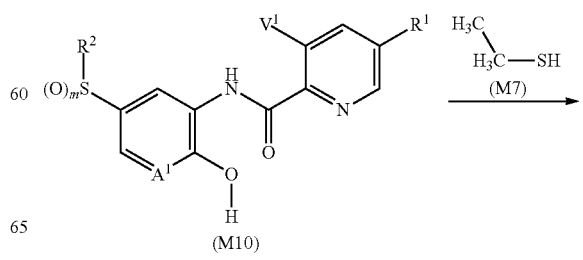

-continued

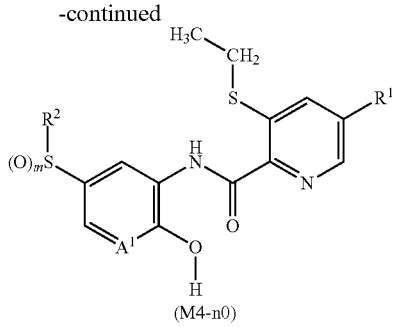

(M4-n0)

wherein $A^1$ represents N or CH, $V^1$ represents a halogen atom and the other symbols are as defined in the formula (1).

The intermediate compound (M4-n0) wherein n is 0 can be produced in the same manner as in Production process 7 by using the intermediate compound (M10) instead of the intermediate compound (M6).

In the reaction, $V^1$ is preferably a fluorine atom or a chlorine atom.

(Production Process 11)

The intermediate compound (M2) can be produced by hydrolyzing the intermediate compound (M12).

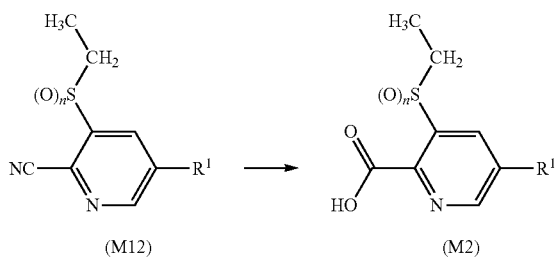

(M12) → (M2)

wherein the symbols are as defined in the formula (1).

When the hydrolysis is conducted by using an acid, an aqueous solution of the acid is generally used as a solvent in the reaction.

Examples of the acid to be used in the reaction include mineral acids such as hydrochloric acid, nitric acid, phosphoric acid, and sulfuric acid; and carboxylic acids such as acetic acid and trifluoroacetic acid.

The reaction temperature of the reaction is generally within a range of 0° C. to 150° C. The reaction time of the reaction is generally within a range of 0.1 to 24 hours.

After the completion of the reaction, the intermediate compound (M2) can be isolated by post-treatments, for example, extracting the reaction mixture with an organic solvent, and drying and concentrating the organic layer. The isolated intermediate compound (M2) can be further purified by chromatography, recrystallization, and the like.

When the hydrolysis is conducted by using a base, the reaction is generally conducted in the presence of a solvent.

Examples of the solvent to be used in the reaction include ethers such as THF, ethylene glycol dimethyl ether, tert-butylmethyl ether, and 1,4-dioxane; alcohols such as methanol and ethanol; water; and mixtures thereof.

Examples of the base to be used in the reaction include alkali metal hydroxides such as sodium hydroxide and potassium hydroxide.

The amount of the base to be used in the reaction is generally 1 to 10 moles relative to 1 mole of the intermediate compound (M12).

The reaction temperature of the reaction is generally within a range of 0° C. to 150° C. The reaction time of the reaction is generally within a range of 0.1 to 24 hours.

After the completion of the reaction, the intermediate compound (M2) can be isolated by post-treatments, for example, acidifying the reaction solution, extracting the reaction mixture with an organic solvent, and drying and concentrating the organic layer. The isolated intermediate compound (M2) can be further purified by chromatography, recrystallization, and the like.

(Production Process 12)

The intermediate compound (M3) can be produced by reacting the intermediate compound (M2) with a chlorinating agent.

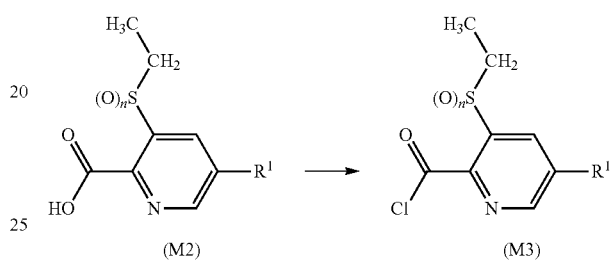

(M2) → (M3)

wherein the symbols are as defined in the formula (1).

The reaction is generally conducted in the presence of a solvent.

Examples of the solvent to be used in the reaction include ethers such as THF, ethylene glycol dimethyl ether, tert-butylmethyl ether, and 1,4-dioxane; aromatic hydrocarbons such as toluene and xylene; aliphatic halogenated hydrocarbons such as dichloromethane and chloroform; and mixtures thereof.

Examples of the chlorinating agent to be used in the reaction include thionyl chloride, oxalyl dichloride, phosphorous oxychloride; and the like.

The amount of the chlorinating agent to be used in the reaction is generally 1 to 5 moles relative to 1 mole of the intermediate compound (M2).

The reaction temperature of the reaction is generally within a range of 0° C. to 100° C. The reaction time of the reaction is generally within a range of 0.1 to 24 hours.

After the completion of the reaction, the intermediate compound (M3) can be isolated by removing the solvent from the reaction mixture.

(Production Process 13)

The intermediate compound (M2), the intermediate compound (M5) or the intermediate compound (M12) can be produced by reacting the intermediate compound (M7) with the intermediate compound (M8), the intermediate compound (M11) or the intermediate compound (M13), respectively, and optionally oxidizing the resulting compound.

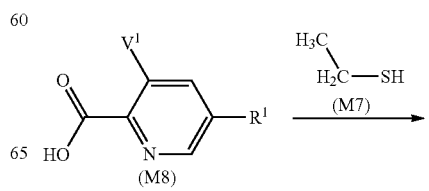

(M8)

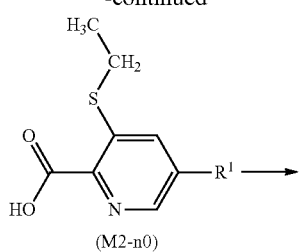

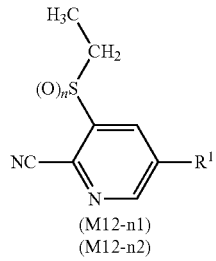

wherein $V^1$ represents a halogen atom and the other symbols are as defined in the formula (1).

The intermediate compound (M2) wherein n is 0 can be produced in the same manner as in Production process 7 by using the intermediate compound (M8) instead of the intermediate compound (M6).

The intermediate compound (M5) wherein n is 0 can be produced in the same manner as in Production process 7 by using the intermediate compound (M11) instead of the intermediate compound (M6).

The intermediate compound (M12) wherein n is 0 can be produced in the same manner as in Production process 7 by using the intermediate compound (M13) instead of the intermediate compound (M6).

The intermediate compound (M2-n1) wherein n is 1 or the intermediate compound (M2-n2) wherein n is 2 can be produced in the same manner as in Production process 1 by using the intermediate compound (M2) wherein n is 0 instead of the present compound (1) wherein n is 0.

The intermediate compound (M5-n1) wherein n is 1 or the intermediate compound (M5-n2) wherein n is 2 can be produced in the same manner as in Production process 1 by using the intermediate compound (M5) wherein n is 0 instead of the present compound (1) wherein n is 0.

The intermediate compound (M12-n1) wherein n is 1 or the intermediate compound (M12-n2) wherein n is 2 can be produced in the same manner as in Production process 1 by using the intermediate compound (M12) wherein n is 0 instead of the present compound (1) wherein n is 0.

In the reaction, $V^1$ is preferably a fluorine atom or a chlorine atom.

(Production Process 14)

The intermediate compound (M1) can be produced by nitrating the intermediate compound (M14) to obtain the intermediate compound (M15), and reducing the resulting intermediate compound (M15).

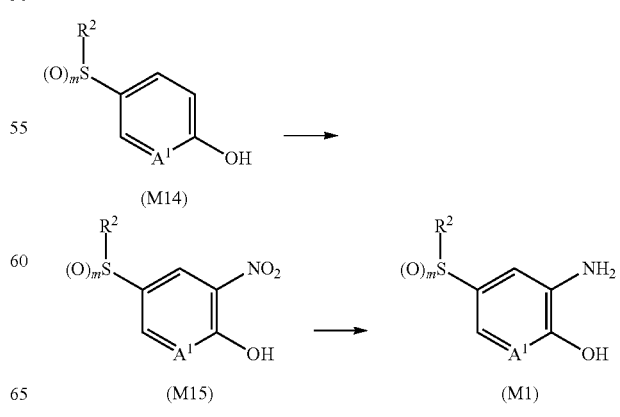

wherein $A^1$ represents N or CH, and the other symbols are as defined in the formula (1).

The intermediate compound (M15) can be produced by reacting the intermediate compound (M14) with a nitrating agent.

The reaction is generally conducted in the presence of a solvent.

Examples of the solvent to be used in the reaction include aliphatic halogenated hydrocarbons such as dichloromethane, and chloroform; acetic acid, concentrated sulfuric acid, concentrated nitric acid, water; and mixtures thereof.

Examples of the nitrating agent to be used in the reaction include concentrated nitric acid; and the like.

The amount of the nitrating agent to be used in the reaction is generally 1 to 3 moles relative to 1 mole of the intermediate compound (M14).

The reaction temperature of the reaction is generally within a range of −10° C. to 100° C. The reaction time of the reaction is generally within a range of 0.1 to 24 hours.

After the completion of the reaction, the intermediate compound (M15) can be isolated by post-treatments, for example, pouring water to the reaction mixture, extracting the reaction mixture with an organic solvent, and drying and concentrating the organic layer. The isolated intermediate compound (M15) can be further purified by chromatography, recrystallization, and the like.

The intermediate compound (M1) can be produced by reacting the intermediate compound (M15) with hydrogen in the presence of a hydrogenating catalyst.

The reaction is generally conducted in the presence of a solvent under hydrogen atmosphere at 1 to 100 atm.

Examples of the solvent to be used in the reaction include ethers such as THF, ethylene glycol dimethyl ether, tert-butylmethyl ether, and 1,4-dioxane; esters such as ethyl acetate and butyl acetate; alcohols such as methanol and ethanol; water; and mixtures thereof.

Examples of the hydrogenating catalyst to be used in the reaction include transition metal compounds such as palladium carbon, palladium hydroxide, Raney nickel, and platinum oxide.

The amount of the hydrogen to be used in the reaction is generally 3 moles relative to 1 mole of the intermediate compound (M15). The amount of the hydrogenating catalyst to be used in the reaction is generally 0.001 to 0.5 moles relative to 1 mole of the intermediate compound (M15).

The reaction temperature of the reaction is generally within a range of −20° C. to 100° C. The reaction time of the reaction is generally within a range of 0.1 to 24 hours.

After the completion of the reaction, the intermediate compound (M1) can be isolated by post-treatments, for example, filtrating the reaction mixture, optionally extracting the reaction mixture with an organic solvent, and drying and concentrating the organic layer. The isolated intermediate compound (M1) can be further purified by chromatography, recrystallization, and the like.

The intermediate compound (M1) can be produced by reacting the intermediate compound (M15) with a reductant.

The reduction reaction may be conducted in the presence of, for example, reductant; acids such as hydrochloric acid and acetic acid; and water.

The reaction is generally conducted in the presence of a solvent.

Examples of the solvent to be used in the reaction include ethers such as THF, ethylene glycol dimethyl ether, tert-butylmethyl ether, and 1,4-dioxane; esters such as ethyl acetate and butyl acetate; alcohols such as methanol and ethanol; aprotic polar solvents such as DMF, NMP, and DMSO; and mixtures thereof.

Examples of the reductant to be used in the reaction include metal powders such as iron powders, zinc powders and tin dichloride powders.

The amount of the reductant to be used in the reaction is generally 3 to 10 moles relative to 1 mole of the intermediate compound (M15). The amount of the acid to be used in the reaction is generally 0.01 to 0.5 moles relative to 1 mole of the intermediate compound (M15). The amount of water to be used in the reaction is generally 3 moles or more relative to 1 mole of the intermediate compound (M15).

The reaction temperature of the reaction is generally within a range of 0° C. to 100° C. The reaction time of the reaction is generally within a range of 0.1 to 24 hours.

After the completion of the reaction, the intermediate compound (M1) can be isolated by post-treatments, for example, pouring water to the reaction mixture, extracting the reaction mixture with an organic solvent, and drying and concentrating the organic layer. The isolated intermediate compound (M1) can be also purified by chromatography, recrystallization, and the like.

(Production Process 15)

The intermediate compound (M17) can be produced by reacting the intermediate compound (M16) with a sulfidizing agent. The intermediate compound (M18), which is a disulfide of the intermediate compound (M17), can be produced by oxidizing two molecules of the intermediate compound (M17).

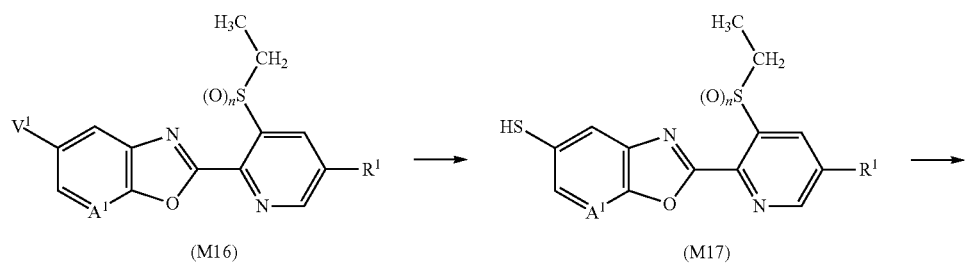

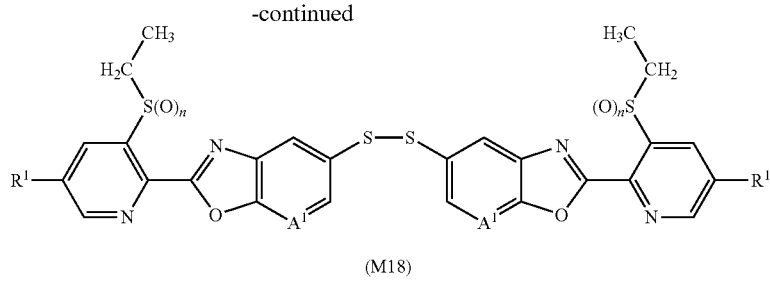

(M18)

wherein $A^1$ represents N or CH, $V^1$ represents a halogen atom and the other symbols are as defined in the formula (1).

The intermediate compound (M17) can be produced by reacting the intermediate compound (M16) in the presence of a sulfidizing agent and a catalyst.

The reaction is generally conducted in the presence of a solvent.

Examples of the solvent to be used in the reaction include aromatic hydrocarbons such as toluene and xylene; aprotic polar solvents such as DMF, NMP, and DMSO; and mixtures thereof.

Examples of the sulfidizing agent to be used in the reaction include sodium sulfide, sodium sulfide 9-hydrate, and thiourea.

Examples of the catalyst to be used in the reaction include copper (I) chloride, copper (I) bromide, and copper (I) iodide.

The reaction may be conducted in the presence of a ligand.

Examples of the ligand to be used in the reaction include acetylacetone, salen, phenanthroline; and the like.

The reaction may be conducted in the presence of a base.

Examples of the base to be used in the reaction include inorganic bases such as potassium carbonate, cesium carbonate, and tripotassium phosphate; and organic bases triethylamine.

The amount of the sulfidizing agent to be used in the reaction is generally 1 to 10 moles relative to 1 mole of the intermediate compound (M16). The amount of the catalyst to be used in the reaction is generally 0.1 to 5 moles relative to 1 mole of the intermediate compound (M16). The amount of the ligand to be used in the reaction is generally 0.1 to 5 moles relative to 1 mole of the intermediate compound (M16). The amount of the base to be used in the reaction is generally 1 to 2 moles relative to 1 mole of the intermediate compound (M16).

The reaction temperature of the reaction is generally within a range of 50° C. to 200° C. The reaction time of the reaction is generally within a range of 0.5 to 24 hours.

After the completion of the reaction, the intermediate compound (M17) can be isolated by post-treatments, for example, extracting the reaction mixture with an organic solvent, and drying and concentrating the organic layer. The isolated intermediate compound (M17) can be further purified by chromatography, recrystallization, and the like.

In the reaction, $V^1$ is preferably a bromine atom and an iodine atom.

In the reaction, the reaction from the intermediate compound (M17) to intermediate compound (M18) is easily progressed, and thus the intermediate compound (M18) may be produced during the synthesis of the present compound (M17).

The intermediate compound (M18) can be produced by reacting two molecules of the intermediate compound (M17) in the presence of an oxidant.

The reaction is generally conducted in the presence of a solvent.

Examples of the solvent to be used in the reaction include water; alcohols such as methanol and ethanol; ethers such as THF, ethylene glycol dimethyl ether, tert-butylmethyl ether, and 1,4-dioxane; aromatic hydrocarbons such as toluene and xylene; nitriles such as acetonitrile; aprotic polar solvents such as DMF, NMP, and DMSO; carboxylic acids such as acetic acid; and mixtures thereof.

Examples of the oxidant to be used in the reaction include oxygen, iodine, hydrogen peroxide solution, potassium ferricyanide, and the like.

The amount of the oxidant to be used in the reaction is generally 0.5 to 10 moles relative to 1 mole of the intermediate compound (M17).

The reaction temperature of the reaction is generally within a range of 0 to 100° C. The reaction time of the reaction is generally within a range of 0.1 to 24 hours.

After the completion of the reaction, the intermediate compound (M18) can be isolated by post-treatments, for example, extracting the reaction mixture with an organic solvent, and drying and concentrating the organic layer. The isolated intermediate compound (M18) can be further purified by chromatography, recrystallization, and the like.

(Production Process 16)

The intermediate compound (M17) can be produced by thioesterificating the intermediate compound (M16) to obtain the intermediate compound (M19), and then hydrolyzing the resulting intermediate compound (M19).

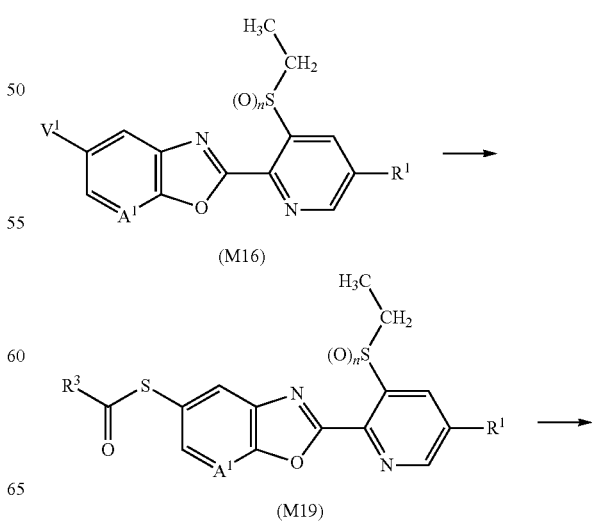

-continued

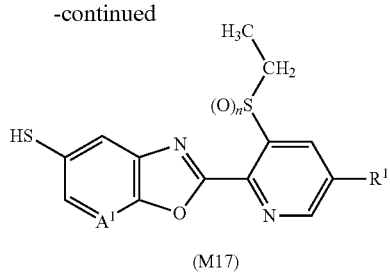

(M17)

wherein $A^1$ represents N or CH, $R^3$ represents a phenyl having one or more halogen atoms and the other symbols are as defined in the formula (1).

The intermediate compound (M19) can be produced by reacting the intermediate compound (M16) in the presence of a thioesterificating agent, a base and a catalyst.

The reaction is generally conducted in the presence of a solvent.

Examples of the solvent to be used in the reaction include aromatic hydrocarbons such as toluene and xylene; aprotic polar solvents such as DMF, NMP, and DMSO; and mixtures thereof.

Examples of the thioesterificating agent to be used in the reaction include thiobenzoic acid.

Examples of the catalyst to be used in the reaction include copper (I) chloride, copper (I) bromide, and copper (I) iodide.

The reaction may be conducted in the presence of a ligand.

Examples of the ligand to be used in the reaction include acetylacetone, salen, phenanthroline; and the like.

Examples of the base to be used in the reaction include inorganic bases such as potassium carbonate, cesium carbonate, and tripotassium phosphate; and organic bases triethylamine.

The amount of the thioesterificating agent to be used in the reaction is generally 1 to 10 moles relative to 1 mole of the intermediate compound (M16). The amount of the catalyst to be used in the reaction is generally 0.1 to 5 moles relative to 1 mole of the intermediate compound (M16). The amount of the ligand to be used in the reaction is generally 0.1 to 5 moles relative to 1 mole of the intermediate compound (M16). The amount of the base to be used in the reaction is generally 1 to 2 moles relative to 1 mole of the intermediate compound (M16).

The reaction temperature of the reaction is generally within a range of 50° C. to 200° C. The reaction time of the reaction is generally within a range of 0.5 to 24 hours.

After the completion of the reaction, the intermediate compound (M19) can be isolated by post-treatments, for example, extracting the reaction mixture with an organic solvent, and drying and concentrating the organic layer. The isolated intermediate compound (M19) can be further purified by chromatography, recrystallization, and the like.

In the reaction, $V^1$ is preferably a bromine atom and an iodine atom.

The intermediate compound (M17) can be produced by hydrolyzing the intermediate compound (M19).

When the hydrolysis is conducted by using an acid, an aqueous solution of the acid is generally used as a solvent in the reaction.

Examples of the acid to be used in the reaction include mineral acids such as hydrochloric acid, nitric acid, phosphoric acid, and sulfuric acid; and carboxylic acids such as acetic acid and trifluoroacetic acid.

The reaction temperature of the reaction is generally within a range of 0° C. to 100° C. The reaction time of the reaction is generally within a range of 0.1 to 24 hours.

After the completion of the reaction, the intermediate compound (M17) can be isolated by post-treatments, for example, extracting the reaction mixture with an organic solvent, and drying and concentrating the organic layer. The isolated intermediate compound (M17) can be further purified by chromatography, recrystallization, and the like.

When the hydrolysis is conducted by using a base, the reaction is generally conducted in the presence of a solvent.

Examples of the solvent to be used in the reaction include ethers such as THF, ethylene glycol dimethyl ether, tert-butylmethyl ether, and 1,4-dioxane; alcohols such as methanol and ethanol; water; and mixtures thereof.

Examples of the base to be used in the reaction include alkali metal hydroxides such as sodium hydroxide and potassium hydroxide.

The amount of the base to be used in the reaction is generally 1 to 10 moles relative to 1 mole of the intermediate compound (M19).

The reaction temperature of the reaction is generally within a range of 0° C. to 120° C. The reaction time of the reaction is generally within a range of 0.1 to 24 hours.

After the completion of the reaction, the intermediate compound (M17) can be isolated by post-treatments, for example, acidifying the reaction solution, extracting the reaction mixture with an organic solvent, and drying and concentrating the organic layer. The isolated intermediate compound (M17) can be further purified by chromatography, recrystallization, and the like.

In the reaction, the reaction from the intermediate compound (M17) to intermediate compound (M18) is easily progressed, and thus the intermediate compound (M18) may be produced during the synthesis of the present compound (M17).

(Production Process 17)

The present compound (1-m0) wherein m is 0 can be produced by reacting the intermediate compound (M18) with the intermediate compound (M20) in the presence of a reductant.

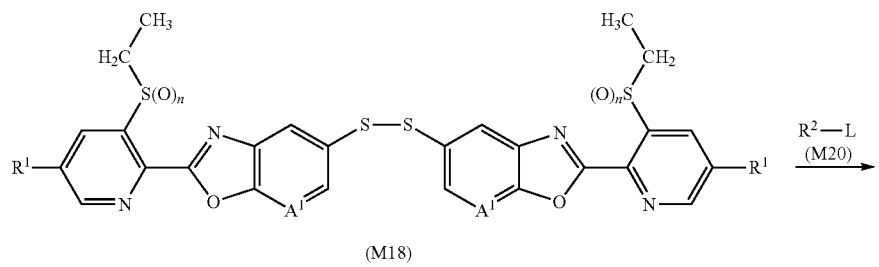

(M18)

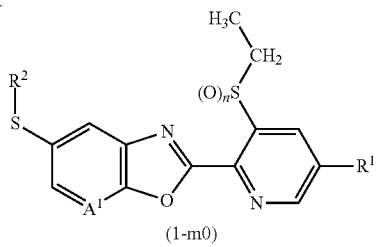

(1-m0)

wherein $A^1$ represents N or CH, L represents a bromine atom or an iodine atom, and the other symbols are as defined in the formula (1).

The reaction is generally conducted in the presence of a solvent.

Examples of the solvent to be used in the reaction include ethers such as THF, ethylene glycol dimethyl ether, tert-butylmethyl ether, and 1,4-dioxane; aromatic hydrocarbons such as toluene and xylene; nitriles such as acetonitrile; aprotic polar solvents such as DMF, NMP, and DMSO; and mixtures thereof.

Examples of the reductant to be used in the reaction include tetrakis(dimethylamino)ethylene, hydrazine, hydrazine monohydrate, and the like.

Examples of the intermediate compound (M20) to be used in the reaction include trifluoromethane iodide, pentafluoroethane iodide, heptafluoro-2-iodopropane, and the like.

The amount of the intermediate compound (M20) to be used in the reaction is generally 2 to 10 moles relative to 1 mole of the intermediate compound (M18). The amount of the reductant to be used in the reaction is generally 1 to 5 moles relative to 1 mole of the intermediate compound (M18).

The reaction temperature of the reaction is generally within a range of −80° C. to 50° C. The reaction time of the reaction is generally within a range of 0.1 to 24 hours.

After the completion of the reaction, the present compound (1-m0) wherein m is 0 can be isolated by post-treatments, for example, extracting the reaction mixture with an organic solvent, and drying and concentrating the organic layer. The isolated present compound (1-m0) can be further purified by chromatography, recrystallization, and the like.

(Production Process 18)

The compound represented by formula (1-n1):

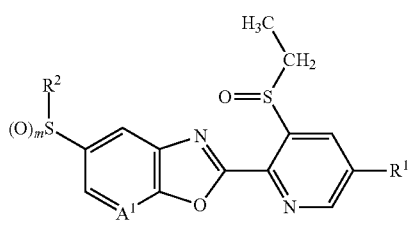

(1-n1)

wherein m represents 0 or 2, and the other symbols are as defined in the formula (1), and the compound represented by formula (1-m1):

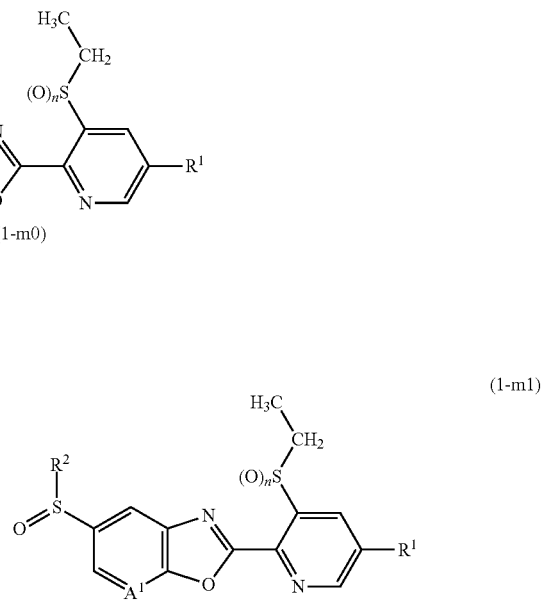

(1-m1)

wherein n represents 0 or 2, and the other symbols are as defined in the formula (1) include stereoisomers, and they can be subjected to optical resolution to give enantiomers thereof.

Namely, the compound represented by formula (1-n1) or (1-m1) can be divided into (+)-enantiomer and (−)-enantiomer by HPLC for using optical resolution column.

Examples of column for optical resolution include those commercially available, for example, CHRALPAK IC® and CHIRALPAK AD® manufactured by Daicel Corporation.

Examples of the mobile phase to be used in optical resolution include aliphatic hydrocarbons such as hexane, heptane, and octane; alcohols such as methanol, ethanol and 2-propanol; aliphatic halogenated hydrocarbons such as dichloromethane and chloroform; ethers such as THF, ethylene glycol dimethyl ether, tert-butylmethyl ether, and 1,4-dioxane; esters such as ethyl acetate and butyl acetate; nitriles such as acetonitrile; carboxylic acids such as acetic acid and formic acid; water; and mixtures thereof.

The temperature of optical resolution is generally −20° C. to 60° C.

Examples of the enantiomer in the present invention include the following present compound (1E) and present compound (1F).

A compound represented by formula (1E):

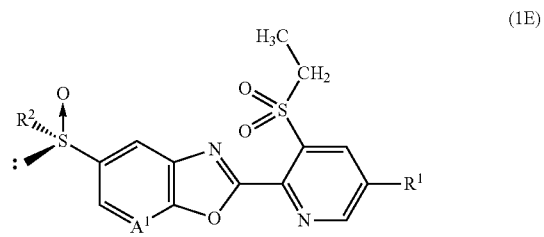

(1E)

wherein $A^1$ represents N or CH, and the other symbols are as defined in the formula (1).

A compound represented by formula (1F):

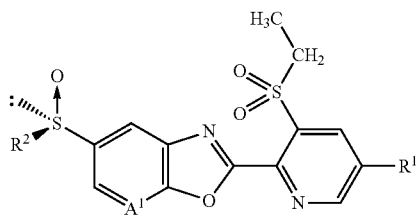

wherein $A^1$ represents N or CH, and the other symbols are as defined in the formula (1).

Examples of the intermediate compounds include the following compounds:

A compound represented by formula (M4):

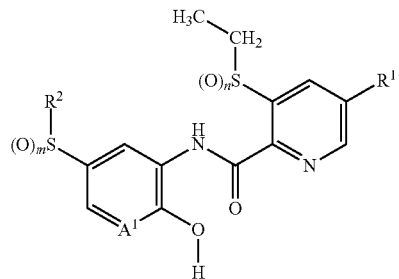

wherein $A^1$ represents N or CH, and the other symbols are as defined in the formula (1).

Examples of the intermediate compound (M4) include the following compounds:

A compound represented by formula (M4) wherein $A^1$ is N, $R^1$ is a trifluoromethyl group, and $R^2$ is a trifluoromethyl group;
A compound represented by formula (M4) wherein $A^1$ is N, $R^1$ is a chlorine atom, and $R^2$ is a trifluoromethyl group;
A compound represented by formula (M4) wherein $A^1$ is N, $R^1$ is a bromine atom, and $R^2$ is a trifluoromethyl group;
A compound represented by formula (M4) wherein $A^1$ is N, $R^1$ is a hydrogen atom, and $R^2$ is a trifluoromethyl group;
A compound represented by formula (M4) wherein $A^1$ is CH, $R^1$ is a trifluoromethyl group, and $R^2$ is a trifluoromethyl group;
A compound represented by formula (M4) wherein $A^1$ is CH, $R^1$ is a chlorine atom, and $R^2$ is a trifluoromethyl group;
A compound represented by formula (M4) wherein $A^1$ is CH, $R^1$ is a bromine atom, and $R^2$ is a trifluoromethyl group;
A compound represented by formula (M4) wherein $A^1$ is CH, $R^1$ is a hydrogen atom, and $R^2$ is a trifluoromethyl group;
A compound represented by formula (M6):

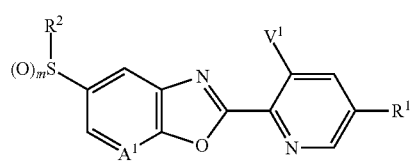

wherein $A^1$ represents N or CH, $V^1$ represents a fluorine atom or chlorine atom, and the other symbols are as defined in the formula (1).

Examples of the intermediate compound (M6) include the following compounds:

A compound represented by formula (M6) wherein $V^1$ is a fluorine atom;
A compound represented by formula (M6) wherein $V^1$ is a chlorine atom;
A compound represented by formula (M6) wherein $A^1$ is N, $R^1$ is a trifluoromethyl group, and $R^2$ is a trifluoromethyl group;
A compound represented by formula (M6) wherein $A^1$ is N, $R^1$ is a chlorine atom, and $R^2$ is a trifluoromethyl group;
A compound represented by formula (M6) wherein $A^1$ is N, $R^1$ is a bromine atom, and $R^2$ is a trifluoromethyl group;
A compound represented by formula (M6) wherein $A^1$ is N, $R^1$ is a hydrogen atom, and $R^2$ is a trifluoromethyl group;
A compound represented by formula (M6) wherein $A^1$ is CH, $R^1$ is a trifluoromethyl group, and $R^2$ is a trifluoromethyl group;
A compound represented by formula (M6) wherein $A^1$ is CH, $R^1$ is a chlorine atom, and $R^2$ is a trifluoromethyl group;
A compound represented by formula (M6) wherein $A^1$ is CH, $R^1$ is a bromine atom, and $R^2$ is a trifluoromethyl group;
A compound represented by formula (M6) wherein $A^1$ is CH, $R^1$ is a hydrogen atom, and $R^2$ is a trifluoromethyl group;
A compound represented by formula (M10):

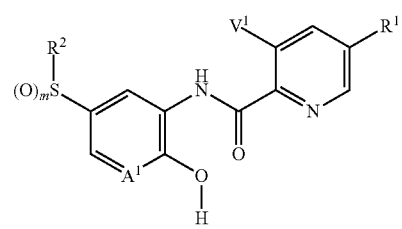

wherein $A^1$ represents N or CH, $V^1$ represents a fluorine atom or chlorine atom, and the other symbols are as defined in the formula (1).

Examples of the intermediate compound (M10) include the following compounds:

A compound represented by formula (M10) wherein $V^1$ is a fluorine atom;
A compound represented by formula (M10) wherein $V^1$ is a chlorine atom;
A compound represented by formula (M10) wherein $A^1$ is N, $R^1$ is a trifluoromethyl group, and $R^2$ is a trifluoromethyl group;
A compound represented by formula (M10) wherein $A^1$ is N, $R^1$ is a chlorine atom, and $R^2$ is a trifluoromethyl group;
A compound represented by formula (M10) wherein $A^1$ is N, $R^1$ is a bromine atom, and $R^2$ is a trifluoromethyl group;
A compound represented by formula (M10) wherein $A^1$ is N, $R^1$ is a hydrogen atom, and $R^2$ is a trifluoromethyl group;
A compound represented by formula (M10) wherein $A^1$ is CH, $R^1$ is a trifluoromethyl group, and $R^2$ is a trifluoromethyl group;
A compound represented by formula (M10) wherein $A^1$ is CH, $R^1$ is a chlorine atom, and $R^2$ is a trifluoromethyl group;

A compound represented by formula (M10) wherein $A^1$ is CH, $R^1$ is a bromine atom, and $R^2$ is a trifluoromethyl group;

A compound represented by formula (M10) wherein $A^1$ is CH, $R^1$ is a hydrogen atom, and $R^2$ is a trifluoromethyl group;

A compound represented by formula (M16):

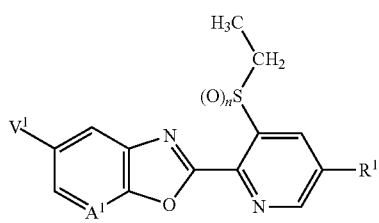

(M16)

wherein $A^1$ represents N or CH, $V^1$ represents a bromine atom or an iodine atom, and the other symbols are as defined in the formula (1) (the intermediate compound (M16)").

Examples of the intermediate compound (M16) include the following compounds:

A compound represented by formula (M16) wherein $V^1$ is a bromine atom;

A compound represented by formula (M16) wherein $V^1$ is an iodine atom;

A compound represented by formula (M16) wherein $A^1$ is N, and $R^1$ is a trifluoromethyl group;

A compound represented by formula (M16) wherein $A^1$ is N, and $R^1$ a chlorine atom;

A compound represented by formula (M16) wherein $A^1$ is N, and $R^1$ a bromine atom;

A compound represented by formula (M16) wherein $A^1$ is N, and $R^1$ a hydrogen atom;

A compound represented by formula (M16) wherein $A^1$ is CH, and $R^1$ is a trifluoromethyl group;

A compound represented by formula (M16) wherein $A^1$ is CH, and $R^1$ a chlorine atom;

A compound represented by formula (M16) wherein $A^1$ is CH, and $R^1$ a bromine atom;

A compound represented by formula (M16) wherein $A^1$ is CH, and $R^1$ a hydrogen atom;

Next, specific examples of the present compound are described below.

A compound represented by formula (1):

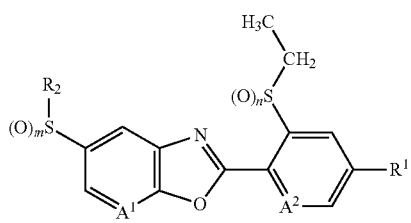

(1)

wherein n is 0, m is 0, $A^2$ is N, and $R^1$, $R^2$ and $A^1$ represent any one of the combinations as listed in Table 1 to table 2.

TABLE 1

| $R^1$ | $R^2$ | $A^1$ |
|---|---|---|
| H | $CF_3$ | N |
| H | $CF_3$ | CH |

TABLE 1-continued

| $R^1$ | $R^2$ | $A^1$ |
|---|---|---|
| $CF_3$ | $CF_3$ | N |
| $CF_3$ | $CF_3$ | CH |
| F | $CF_3$ | N |
| F | $CF_3$ | CH |
| Cl | $CF_3$ | N |
| Cl | $CF_3$ | CH |
| Br | $CF_3$ | N |
| Br | $CF_3$ | CH |
| I | $CF_3$ | N |
| I | $CF_3$ | CH |
| H | $CF_2CF_3$ | N |
| H | $CF_2CF_3$ | CH |
| $CF_3$ | $CF_2CF_3$ | N |
| $CF_3$ | $CF_2CF_3$ | CH |
| F | $CF_2CF_3$ | N |
| F | $CF_2CF_3$ | CH |
| Cl | $CF_2CF_3$ | N |
| Cl | $CF_2CF_3$ | CH |
| Br | $CF_2CF_3$ | N |
| Br | $CF_2CF_3$ | CH |
| I | $CF_2CF_3$ | N |
| I | $CF_2CF_3$ | CH |

TABLE 2

| $R^1$ | $R^2$ | $A^1$ |
|---|---|---|
| H | $CF(CF_3)_2$ | N |
| H | $CF(CF_3)_2$ | CH |
| $CF_3$ | $CF(CF_3)_2$ | N |
| $CF_3$ | $CF(CF_3)_2$ | CH |
| F | $CF(CF_3)_2$ | N |
| F | $CF(CF_3)_2$ | CH |
| Cl | $CF(CF_3)_2$ | N |
| Cl | $CF(CF_3)_2$ | CH |
| Br | $CF(CF_3)_2$ | N |
| Br | $CF(CF_3)_2$ | CH |
| I | $CF(CF_3)_2$ | N |
| I | $CF(CF_3)_2$ | CH |
| H | $CF_2CF_2CF_3$ | N |
| H | $CF_2CF_2CF_3$ | CH |
| $CF_3$ | $CF_2CF_2CF_3$ | N |
| $CF_3$ | $CF_2CF_2CF_3$ | CH |
| F | $CF_2CF_2CF_3$ | N |
| F | $CF_2CF_2CF_3$ | CH |
| Cl | $CF_2CF_2CF_3$ | N |
| Cl | $CF_2CF_2CF_3$ | CH |
| Br | $CF_2CF_2CF_3$ | N |
| Br | $CF_2CF_2CF_3$ | CH |
| I | $CF_2CF_2CF_3$ | N |
| I | $CF_2CF_2CF_3$ | CH |

The present compound represented by formula (1) wherein n is 1, m is 0, $A^2$ is N, and $R^1$, $R^2$ and $A^1$ represent any one of the combinations as listed in Table 1 to table 2.

The present compound represented by formula (1) wherein n is 2, m is 0, $A^2$ is N, and $R^1$, $R^2$ and $A^1$ represent any one of the combinations as listed in Table 1 to table 2.

The present compound represented by formula (1) wherein n is 0, m is 1, $A^2$ is N, and $R^1$, $R^2$ and $A^1$ represent any one of the combinations as listed in Table 1 to table 2.

The present compound represented by formula (1) wherein n is 1, m is 1, $A^2$ is N, and $R^1$, $R^2$ and $A^1$ represent any one of the combinations as listed in Table 1 to table 2.

The present compound represented by formula (1) wherein n is 2, m is 1, $A^2$ is N, and $R^1$, $R^2$ and $A^1$ represent any one of the combinations as listed in Table 1 to table 2.

The present compound represented by formula (1) wherein n is 0, m is 2, $A^2$ is N, and $R^1$, $R^2$ and $A^1$ represent any one of the combinations as listed in Table 1 to table 2.

The present compound represented by formula (1) wherein n is 1, m is 2, $A^2$ is N, and $R^1$, $R^2$ and $A^1$ represent any one of the combinations as listed in Table 1 to table 2.

The present compound represented by formula (1) wherein n is 2, m is 2, $A^2$ is N, and $R^1$, $R^2$ and $A^1$ represent any one of the combinations as listed in Table 1 to table 2.

The present compound represented by formula (1E):

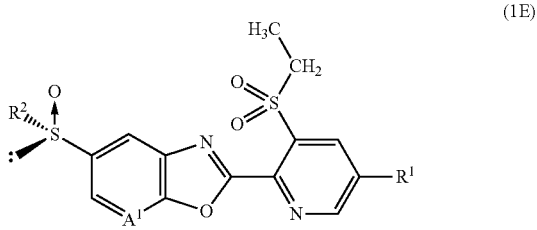

(1E)

wherein $R^1$, $R^2$ and $A^1$ represent any one of the combinations as listed in Table 1 to table 2.

The present compound represented by formula (1F):

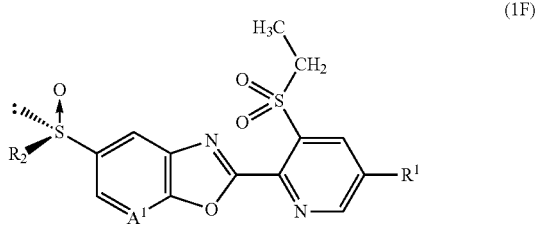

(1F)

wherein $R^1$, $R^2$ and $A^1$ represent any one of the combinations as listed in Table 1 to table 2.

Examples of pests on which the present compound exhibits a controlling effect include arthropod pests such as harmful insects and harmful mites, and nematodes. More specifically, the following pests are included.

Hemiptera: Delphacidae such as *Laodelphax striatella*, *Nilaparvata lugens*, and *Sogatella furcifera*; Deltocephalidae such as *Nephotettix cincticeps*, *Nephotettix virescens*, and *Empoasca onukii*; Aphididae such as *Aphis gossypii*, *Myzus persicae*, *Brevicoryne brassicae*, *Aphis spiraecola*, *Macrosiphum euphorbiae*, *Aulacorthum solani*, *Rhopalosiphum padi*, *Toxoptera citricidus*, and *Hyalopterus pruni*; Pentatomidae such as *Nezara antennata*, *Eysarcoris parvus*, and *Halyomorpha mista*; Alydidae such as *Riptortus clavetus*, *Leptocorisa chinensis*; Kirkaldy such as *Trigonotylus caelestialium*, *Stenotus rubrovittatus*; Aleyrodidae such as *Trialeurodes vaporariorum*, *Bemisia tabaci*, *Dialeurodes citri*, *Aleurocanthus spiniferus*; Coccidea such as *Aonidiella aurantii*, *Comstockaspis perniciosa*, *Unaspis citri*, *Ceroplastes rubens*, *Icerya purchasi*, *Planococcus kraunhiae*, *Pseudococcus longispinis*, and *Pseudaulacaspis pentagona*; Psyllidae such as *Diaphorina citri*, *Psylla pyrisuga*, and *Bactericerca cockerelli*; Tingidae such as *Stephanitis nasi*; Cimicidae such as *Cimex lectularius*.

Lepidoptera: Pyralidae such as *Chilo suppressalis*, *Tryporyza incertulas*, *Cnaphalocrocis medinalis*, *Notarcha derogata*, *Plodia interpunctella*, *Ostrinia furnacalis*, *Hellula undalis*, and *Pediasia teterrellus*; Noctuidae such as *Spodoptera litura*, *Spodoptera exigua*, *Pseudaletia separata*, *Mamestra brassicae*, *Agrotis ipsilon*, *Plusia nigrisigna*, *Trichoplusia* spp., *Heliothis* spp., and *Helicoverpa* spp.; Pieridae such as *Pieris rapae*; Torsuch as *Adoxophyes* spp., *Grapholita molesta*, *Leguminivora glycinivorella*, *Matsumuraeses azukivora*, *Adoxophyes orana fasciata*, *Adoxophyes honmai.*, *Homona magnanima*, *Archips fuscocupreanus*, and *Cydia pomonella*; Gracillariidae such as *Caloptilia theivora*, and *Phyllonorycter ringoneella*; Carposinidae such as *Carposina niponensis*; Lyonetiidae such as *Lyonetia* spp.; Lymantriidae such as *Lymantria* spp., and *Euproctis* spp.; Yponomeutidae such as *Plutella xylostella*; Gelechiidae such as *Pectinophora gossypiella*, and *Phthorimaea operculella*; Arctiidae such as *Hyphantria cunea*; and Tineidae such as *Tinea translucens*, and *Tineola bisselliella*.

Thysanoptera: Thripidae such as *Frankliniella occidentalis*, *Thrips parmi*, *Scirtothrips dorsalis*, *Thrips tabaci*, and *Frankliniella intonsa*.

Diptera: Culices such as *Culex pipiens pallens*, *Culex tritaeniorhynchus*, and *Culex quinquefasciatus*; *Aedes* spp. such as *Aedes aegypti*, and *Aedes albopictus*; *Anopheles* spp. such as *Anopheles sinensis*; Chironomidae; Muscidae such as *Musca domestica*, and *Muscina stabulans*; Calliphoridae; Sarcophagidae; Fanniidae; Anthomyiidae such as *Delia platura*, and *Delia antiqua*; Agromyzidae such as *Agromyza oryzae*, *Hydrellia griseola*, *Liriomyza sativae*, *Liriomyza trifolii*, and *Chromatomyia horticola*; Chloropidae such as *Chlorops oryzae*; Tephritidae such as *Dacus cucurbitae*, and *Ceratitis capitata*; Drosophilidae; Phoridae such as *Megaselia spiracularis*; Psychodidae such as *Clogmia albipunctata*; Simuliidae; Tabanidae such as *Tabanus trigonus*; Hippoboscidae; and Stomoxyini.

Coleoptera: *Diabrotica* spp. such as *Diabrotica virgifera virgifera*, *Diabrotica undecimpunctata howardi*, *Oulema oryzae*, *Aulacophora femoralis*, *Phyllotreta striolata*, and *Leptinotarsa decemlineata*; Scarabaeidae such as *Anomala cuprea*, *Anomala rufocuprea*, and *Popillia japonica*; Sitophilini such as *Sitophilus zeamais*, *Echinocnemus squameus*, *Lissorhoptrus oryzophilus*, and *Sphenophorus venatus*; Curculionoidea such as *Anthonomus grandis*; Bruchinae such as *Callosobruchuys chienensis*; Heteromera such as *Tenebrio molitor*, and *Tribolium castaneum*; Dermestidae such as *Anthrenus verbasci*), and *Dermestes maculates*; Anobiidae such as *Lasioderma serricorne*; Epilachna such as *Epilachna vigintioctopunctata*; Scolytidae such as *Lyctus brunneus*, and *Tomicus piniperda*; Bostrychidae; Ptinidae; Cerambycidae such as *Anoplophora malasiaca*; *Agriotes* spp. such as *Agriotes ogurae fuscicollis*; and Staphylinidae such as *Paederus fuscipes*.

Orthoptera: *Locusta migratoria*, *Gryllotalpa africana*, *Oxya yezoensis*, *Oxya japonica*, and Gryllidae.

Siphonaptera: *Ctenocephalides felis*, *Ctenocephalides canis*, *Pulex irritans*, *Xenopsylla cheopis*, and the like.

Anoplura: *Pediculus humanus corporis*, *Pediculus humanus humanus*, *Phthirus pubis*, *Haematopinus eurysternus*, *Dalmalinia ovis*, *Haematopinus suis*, *Linognathus setosus*, and the like.

Mallophage: *Dalmalinia ovis*, *Dalmalinia bovis*, *Menopon gallinae*, *Trichodectes canis*, *Felicola subrostrata*, and the like.

Hymenoptera: Formicidae such as *Monomorium pharaosis*, *Formica fusca japonica*, *Ochetellus glaber*, *Pristomyrmex pungens*, *Pheidole noda*, *Acromyrmex* spp., *Solenopsis* spp., and *Linepithema humile*; Vespidae, Bethylidae, and Symphyta such as *Athalia rosae*, and *Athalia japonica*.

Nematoda: *Aphelenchoides besseyi*, *Nothotylenchus acris*, *Meloidogyne incognita*, *Meloidogyne hapla*, *Meloidogyne javanica*, *Heterodera glycines*, *Globodera rostochiensis*, *Pratylenchus coffeae*, *Pratylenchus neglectus*, and the like.

Blattodea: *Blattella germanica, Periplaneta fuliginosa, Periplaneta americana, Periplaneta brunnea, Blatta orientalis*, and the like.

Termitidae: *Reticulitermes speratus, Coptotermes formosanus, Incisitermes minor, Cryptotermes domesticus, Odontotermes formosanus, Neotermes koshunensis, Glyptotermes satsumensis, Glyptotermes nakajimai, Glyptotermes fuscus, Glyptotermes kodamai, Glyptotermes kushimensis, Hodotermopsis japonica, Coptotermes guangzhoensis, Reticulitermes miyatakei, Reticulitermes flaviceps amamianus, Reticulitermes* sp., *Nasutitermes takasagoensis, Pericapritermes nitobei, Sinocapritermes mushae*, and the like.

Acari: Tetranychidae such as *Tetranychus urticae, Tetranychus kanzawai, Panonychus citri, Panonychus ulmi,* and *Oligonychus* spp.; Eriophyidae such as *Aculops pelekassi, Phyllocoptruta citri, Aculops lycopersici, Calacarus carinatus, Acaphylla theavagrans, Eriophyes chibaensis,* and *Aculus schlechtendali;* Tarsonemidae such as *Polyphagotarsonemus latus;* Tenuipalpidae such as *Brevipalpus phoenicis;* Tuckerellidae; Ixodidae such as *Haemaphysalis longicornis, Haemaphysalis flava, Dermacentor taiwanicus, Dermacentor variabilis, Ixodes ovatus, Ixodes persulcatus, Ixodes scapularis, Amblyomma americanum, Boophilus microplus,* and *Rhipicephalus sanguineus;* Acaridae such as *Tyrophagus putrescentiae, and Tyrophagus similis;* Pyroglyphidae such as *Dermatophagoides farinae,* and *Dermatophagoides ptrenyssnus;* Cheyletidae such as *Cheyletus eruditus, Cheyletus malaccensis, Cheyletus moorei,* and *Cheyletiella yasguri;* Sarcoptidae such as *Octodectes cynotis,* and *Sacroptes scabiei; Demodex* such as *Demodex canis;* Listrophoridae; Oribatida; Dermanyssidae such as *Ornithonyssus bacoti, Ornithonyssus sylvairum,* and *Dermanyssus gallinae;* and Trombiculidae such as *Leptotrombidium akamushi.*

Araneae: Opisthothelae such as *Chiracanthium japonicum,* and *Latrodectus hasseltii;* and the like.

Chilopoda: *Thereuonema hilgendorfi,* and *Scolopendra subspinipes.*

Diplopoda: *Oxidus gracilis, Nedyopus tambanus,* and the like.

Isopoda: *Armadillidium vulgare,* and the like.

Gastropoda: *Limax marginatus, Limax flavus,* and the like.

The pest control agent of the present invention comprises the present compound and an inert carrier. The pest control agent of the present invention generally comprises the present compound in combination with a solid carrier, a liquid carrier and/or a gaseous carrier, and if necessary, a surfactant or other formulation additives and takes the form of emulsifiable concentrate, oil solution, dusts, granules, wettable powder, suspension concentrate, microcapsules, aerosol, smoking agent, poison bait, resin formulation, shampoo formulation, paste, foam, carbon dioxide gas formulation, tablet or the like. The pest control agent of the present invention may be processed into mosquito coil, electric mosquito mat, electric mosquito liquid, smoking agent, fumigant, sheet, spot-on pesticide, or oral pesticide, and then be used.

The pest control agent of the present invention generally contains 0.01 to 95% by weight of the present compound.

The pest control agent of the present invention comprising any one of the present compounds 1-1 to 1-98 and an inert carrier, wherein the inert carrier is water, and the compound is dispersed in water containing a surfactant, can be generally produced by mixing any one of the present compound 1-1 to 1-98, a surfactant and water, optionally adding other formulation additives thereto, to form a formulation such as suspension concentrate or microcapsules.

Said pest control agent of the present invention generally contains 0.01 to 95% by weight of any of the present compounds 1-1 to 1-98.

The situation that "compound is dispersed in water" used herein includes those that any of the present compound 1-1 to 1-98 is emulsified in water or suspended in water.

Examples of the surfactant include nonionic surfactants and/or anionic surfactants. Examples of the nonionic surfactant include polyoxyalkylene alkyl ether, polyoxyalkylene alkyl aryl ether, polyethylene glycol fatty acid esters, and the like. Examples of anionic surfactant include alkylsulfonates, alkylbenzene sulfoantes, alkyl sulfates, polyoxyalkylene aryl phenyl ether sulfates, polyoxyalkylene aryl phenyl ether phosphate, and the like.

Examples of the other formulation additives include a fixing agent, a dispersant, a colorant, a thickening agent, a preservative, an antifoamer, an antifreezing agent and a stabilizer, and the like, and specific examples include casein, gelatin, starch, gum Arabic, a cellulose derivative, alginic acid, a lignin derivative, a synthetic water-soluble polymer (polyvinyl alcohol, polyvinylpyrrolidone, polyacrylic acids, etc.), PAP (acidic isopropyl phosphate), BHT (2,6-di-tert-butyl-4-methylphenol), and BHA (a mixture of 2-tert-butyl-4-methoxyphenol and 3-tert-butyl-4-methoxyphenol).

The method for controlling a pest of the present invention in agriculture includes a method comprising applying an effective amount of any of the present compounds 1-1 to 1-98 to stem and leaf of a plant or a soil where a plant is grown, specifically, for example, application to stem and leaf of a plant such as foliage application, and application to an area where a plant is grown such as soil application and submerged application soil treatment. The application is generally performed once or more times.

Specific examples of the application to stem and leaf of a plant include application onto the surface of a plant such as foliage application and spraying to the trunk.

Specific examples of the soil application include spraying onto the soil, admixing with the soil, perfusion of an agent liquid into the soil (irrigation of an agent liquid, injection into the soil, dripping of an agent liquid). Examples of the place to be applied include a planting hole, a furrow, peripheral of the planting hole, peripheral of the planting furrow, the entire surface of the growing area, the parts between the soil and the plant, area between roots, area beneath the trunk, main furrow, growing soil, box for raising seedlings, tray for raising seedlings, and seedbed. Examples of the timing of application include before dissemination, at the time of dissemination, immediately after the dissemination, during the raising period of seedlings, before settled planting, at the time of settled planting and growing time after settled planting.

Examples of the submerged application include injection to irrigating facilities (irrigating tube, irrigating pipe, sprinkler, etc.), mixing into the flooding liquid between furrows, and mixing into a water culture medium.

In the method for controlling a pest of the present invention, the present compound is typically applied as the pest control agent of the present invention.

When the pest control agent of the present invention is used for controlling a pest in an agricultural field, the amount is usually in the range from 1 to 10,000 g in terms of the present compound per 10,000 m$^2$. When the pest control agent of the present invention is formulated into an emulsifiable concentrate, a wettable powder, a flowable formulation and so on, the pest control agent is usually applied after diluting with water so that the concentration of the active ingredient becomes 0.01 to 10,000 ppm, and a granule or a dust is usually applied as it is.

When the pest control agent of the present invention is used for controlling a pest in a paddy field, the amount is usually in the range from 0.1 to 10 g in terms of the present compound per a box for raising seedlings. When the pest control agent of the present invention is formulated into an emulsifiable concentrate, a wettable powder, a flowable formulation and so on, the pest control agent is usually applied after diluting with water so that the concentration of the active ingredient becomes 0.01 to 10,000 ppm, and a granule or a dust is usually applied in an amount of 1 to 500 g as it is.

These formulations or water dilutions of the formulations may be directly sprayed over a pest or a plant such as crop plant to be protected from a pest, or may be used in soil treatment for controlling a pest which inhabits a soil of cultivated land.

Application can also be conducted by a method of directly winding the resin formulation formed into sheet-shaped, or corded-shaped formulation around plants, disposing the formulation in the neighborhood of a plant, or spreading the formulation on a soil surface at the root of a plant.

The pest control agent of the present invention containing any of the present compounds 1-1 to 1-98 and an eating carrier (hereinafter referred to as "the poison bait of the present invention") can be generally produced by mixing any of the present compounds 1-1 to 1-98 with an eating carrier (for example, water or nutrients such as carbohydrates, proteins, lipids, etc.).

Examples of the eating carrier include sugars such as sucrose, glucose, granulated sugar, fructose, lactose, maltose, muscovado sugar, brown sugar, soft brown sugar, dextrin, arabinose, galactose, sorbitose, molasses, honey, etc.; milk products such as skim milk, nonfat dry milk, cheese; starches from corn, potato, sweet potato, etc.; grain powders such wheat flour, rice flour, corn flour, potato flour, etc.; animal powders or insect powders such as cows, pigs, fish and shellfish, insects, etc.; vegetable oils such as palm oil, cacao oil, corn oil, sesame oil, peanut oil, and salad oil; animal oils such as body fat (mammal oil), butter fat, oils from birds, reptiles, amphibians, insects, etc.; seasoning agents such as sauce, soy sauce, etc. The poison bait of the present invention may further contain antioxidants such as dibutylhydroxytoluene, nordihydroguaiaretic acid, etc.; preservatives such as dehydroacetic acid; agents for the prevention of accidental ingestion by children or pets such as powdered capsicum; insect pest-attracting agents such as cheese flavoring, onion fragrance, peanut oil, etc.; and the like.

The form of the poison bait composition of the present invention is not particularly limited to, but includes, for example, granule, aggregate, tablet, liquid, paste, gel, etc.

The method for controlling a pest of the present invention in epidemic prevention comprises (1) spreading the poison bait composition of the present invention in the form of a solid such as powder, granule, aggregate, and tablet to a place where a pest is likely to be gathered, or putting the composition into an open container and then placing the container on a place where a pest is likely to be gathered, (2) applying the poison bait composition of the present invention in the form of a liquid on a place where a pest is likely to be gathered, or (3) injecting or attaching the poison bait composition of the present invention in the form of a gel or a past into a gap where a pest is likely to be gathered by using baitgun, etc. to feed a pest the composition.

The pest control agent of the present invention containing any of the present compounds 1-1 to 1-98, a solvent and an propellant gas (hereinafter referred to as "the aerosol of the present invention") can be generally produced by putting any of the present compounds 1-1 to 1-98 and the solvent into an aerosol can, mounting an aerosol valve thereon, introducing an propellant gas thereinto, and then mounting an actuator thereon.

Examples of the solvent include water, alcohols (methanol, ethanol, isopropyl alcohol, butanol, hexanol, benzyl alcohol, ethylene glycol, propylene glycol, phenoxyethanol, etc.), ketones (acetone, methyl ethyl ketone, cyclohexanone, etc.), aromatic hydrocarbons (toluene, xylene, ethylbenzene, dodecylbenzene, phenylxylylethane, methylnaphthalene, etc.), aliphatic hydrocarbons (hexane, cyclohexane, kerosene, gas oil, etc.), esters (ethyl acetate, butyl acetate, isopropyl myristate, ethyl oleate, diisopropyl adipate, diisobutyl adipate, propylene glycol monomethyl ether acetate, etc.), nitriles (acetonitrile, isobutyronitrile, etc.), ethers (diisoprpyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, 3-methoxy-3-methyl-1-butanol, etc.), acid amides (N,N-dimethylformamide, N,N-dimethylacetamide, etc.), halogenated hydrocarbons (dichloromethane, trichloroethane, carbon tetrachloride, etc.), sulfoxides (dimethyl sulfoxide, etc.), propylene carbonate and vegetable oils (soybean oil, cottonseed oil, etc.).

Examples of the propellant gas include fluorocarbons, butane gas, LPG (liquefied petroleum gas), dimethyl ether and carbon dioxide.

The aerosol valve is not particularly limited, but includes, for example, push-down type aerosol valves.

The pest control agent of the present invention containing any of the present compounds 1-1 to 1-98 and a gas-forming agent (hereinafter referred to as "the smoking agent of the present invention") can be generally produced by mixing any of the present compound 1-1 to 1-98 and a gas-forming agent.

Examples of the gas-forming agent include azodicarbonamide, 4,4'-oxybis(benzenesulfonylhydrazide), dinitrosopentamethylenetetramine, 2,2'-azobisisobutyronitrile, p-toluenesulfonylhydrazide, and the like.

When the pest control agent of the present invention is used for epidemic prevention, the application amount is usually 0.01 to 1,000 mg as the present compound per 1 $m^2$ in case of application for plane surface, and 0.01 to 500 mg as the present compound per 1 $m^3$ in case of application for space. When the pest control agent of the present invention is a formulation of emulsions, wettable powders or flowables, they are usually applied after a dilution with water to have an active ingredient concentration of 0.1 to 10,000 ppm. When the pest control agent of the present invention is a formulation of oil solutions, aerosols, smoking agents and poison baits, they are usually applied as such. When the pest control agent of the present invention is sprayed on a pest or a habitat of pest, the application amount is usually 0.01 to 1,000 mg as the present compound per 1 $m^2$ in case of application for plane surface, and 0.01 to 500 mg as the present compound per 1 $m^3$ in case of application for space.

When the pest control agent of the present invention is used for epidemic prevention, the pest control agent can be applied to the body surface of an animal parasitized by a pest, or orally administered to an animal parasitized by a pest. Specifically, the pest control agent can be used for controlling an ectoparasite in livestock such as cattle, horse, pig, sheep, goat, and chicken or a small animal such as dog, cat, rat, and mouse by a known method in the veterinary field. Specifically, when systemic control in an animal is intended, the pest control agent is administered to the animal as a tablet, a mixture with feed or a suppository, or by injection (including intramuscular, subcutaneous, intravenous and intraperitoneal injections). On the other hand, when non-systemic control is intended, the pest control agent is applied to the animal by means of spraying of oil solution or aqueous solution, pour-on or spot-on treatment, or washing of the animal with a shampoo formulation, or by putting a collar or ear tag made of the resin transpiration formulation to the animal. When administered to the body surface of an animal, the amount of the present compound is usually in the range of 0.1 to 1,000 mg per 1 kg body weight of the animal. When orally administered to an animal, the amount of the present compound is usually in the range of 0.1 to 1,000 mg per 1 kg body weight of the animal.

The pest control agent of the present invention can be used in farmlands on which "crops" shown below are cultivated.

Crops: corn, rice, wheat, barley, rye, oat, sorghum, cotton, soybean, peanut, buckwheat, sugar beet, rapeseed, sunflower, sugar cane, tobacco, etc.;

Vegetables: Solanaceae vegetables (eggplant, tomato, green pepper, hot pepper, potato, etc.), Cucurbitaceae vegetables (cucumber, pumpkin, zucchini, watermelon, melon, etc.), Cruciferae vegetables (Japanese radish, turnip, horseradish, kohlrabi, Chinese cabbage, cabbage, brown mustard, broccoli, cauliflower, etc.), Compositae vegetables (burdock, garland chrysanthemum, artichoke, lettuce, etc.), Liliaceae vegetables (Welsh onion, onion, garlic, asparagus), Umbelliferae vegetables (carrot, parsley, celery, parsnip, etc.), Chenopodiaceae vegetables (spinach, Swiss chard, etc.), Labiatae vegetables (Japanese basil, mint, basil, etc.), strawberry, sweat potato, yam, aroid, etc.;

Fruit trees: pomaceous fruits (apple, common pear, Japanese pear, Chinese quince, quince, etc.), stone fleshy fruits (peach, plum, nectarine, Japanese plum, cherry, apricot, prune, etc.), citrus plants (Satsuma mandarin, orange, lemon, lime, grapefruit, etc.), nuts (chestnut, walnut, hazel nut, almond, pistachio, cashew nut, macadamia nut, etc.), berry fruits (blueberry, cranberry, blackberry, raspberry, etc.), grape, persimmon, olive, loquat, banana, coffee, date, coconut, oil palm, etc.;

Trees other than fruit trees: tea, mulberry, flowering trees (azalea, camellia, hydrangea, sasanqua, Japanese star anise, cherry, tulip tree, crape myrtle, orange osmanthus, etc.), street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew, elm, horse chestnut, etc.), coral tree, podocarpus, cedar, Japanese cypress, croton, *Euonymus japonicus*, *Photinia glabra*, etc.;

Lawns: *Zoysia* (zoysiagrass, *Zoysia matrella*, etc.), Bermuda grasses (*Cynodon dactylon*, etc.), bent grasses (*Agrostis alba*, creeping bent grass, hiland bent, etc.), blueglasses (meadow grass, bird grass, etc.), fescue (tall fescue, chewings fescue, creeping red fescue, etc.), ryegrasses (darnel, rye grass, etc.), orchard grass, timothy grass, etc.;

Others: flowers (rose, carnation, chrysanthemum, prairie gentian, gypsophila, gerbera, marigold, salvia, petunia, verbena, tulip, aster, gentian, lily, pansy, cyclamen, orchid, convallaria, lavender, stock, ornamental cabbage, primula, poinsettia, gladiolus, cattleya, daisy, cymbidium, begonia, etc.), bio-fuel plants (Jatropha, safflower, camelina, switchgrass, Miscanthus, reed canary grass, giant reed, kenaf, cassava, willow, etc.), ornamental plants, etc.

The "crops" include genetically modified crops.

The pest control agent of the present invention can be used as a mixture with or together with other insecticides, acaricides, nematocides, fungicides, plant growth regulators, herbicides, and synergists. Examples of active ingredients of the insecticide, the acaricide, the nematocide, the fungicide, the herbicide, and the synergist are shown below.

Examples of active ingredients of the insecticides include:
(1) Organic Phosphorus Compounds:
acephate, Aluminium phosphide, butathiofos, cadusafos, chlorethoxyfos, chlorfenvinphos, chlorpyrifos, chlorpyrifos-methyl, cyanophos: CYAP, diazinon, DCIP (dichlorodiisopropyl ether, dichlofenthion: ECP, dichlorvos: DDVP, dimethoate, dimethylvinphos, disulfoton, EPN, ethion, ethoprophos, etrimfos, fenthion: MPP, fenitrothion: MEP, fosthiazate, formothion, Hydrogen phosphide, isofenphos, isoxathion, malathion, mesulfenfos, methidathion: DMTP, monocrotophos, naled: BRP, oxydeprofos: ESP, parathion, phosalone, phosmet: PMP, pirimiphos-methyl, pyridafenthion, quinalphos, phenthoate: PAP, profenofos, propaphos, prothiofos, pyraclorfos, salithion, sulprofos, tebupirimfos, temephos, tetrachlorvinphos, terbufos, thiometon, trichlorphon: DEP, vamidothion and phorate.

(2) Carbamate Compounds:
alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb: MIPC, metolcarb, methomyl, methiocarb, NAC, oxamyl, pirimicarb, propoxur: PHC, XMC, thiodicarb, xylylcarb, and aldicarb.

(3) Pyrethroid Compounds:
acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, profluthrin, dimefluthrin, 2,3,5,6-tetrafluoro-4-(methoxymethyl)benzyl (EZ)-(1RS,3RS;1RS,3SR)-2,2-dimethyl-3-prop-1-enylcyclopropanecarboxylate, 2,3,5,6-tetrafluoro-4-methylbenzyl (EZ)-(1RS,3RS;1RS,3SR)-2,2-dimethyl-3-prop-1-enylcyclopropanecarboxylate, and 2,3,5,6-tetrafluoro-4-(methoxymethyl)benzyl (1RS,3RS;1RS,3SR)-2,2-dimethyl-3-(2-methyl-1-propenyl)cyclopropanecarboxylate, 2,3,5,6-tetrafluoro-4-(methoxymethyl)benzyl (EZ)-(1RS,3RS;1RS,3SR)-2,2-dimethyl-3-(2-cyano-1-propenyl)cyclopropanecarboxylate.

(4) Nereistoxin Compounds:
cartap, bensultap, thiocyclam, monosultap, and bisultap.

(5) Neonicotinoid Compounds:
imidacloprid, nitenpyram, acetamiprid, thiamethoxam, thiacloprid, dinotefuran, and clothianidin.

(6) Benzoylurea Compounds:
chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, and triazuron.

(7) Phenylpyrazole Compounds:
acetoprole, ethiprole, fipronil, vaniliprole, pyriprole, and pyrafluprole.

(8) Bt Toxins:
live spores derived from and crystal toxins produced from *Bacillus thuringiesis* and a mixture thereof;

(9) Hydrazine Compounds:
chromafenozide, halofenozide, methoxyfenozide, and tebufenozide.

(10) Organic Chlorine Compounds:
aldrin, dieldrin, dienochlor, endosulfan, and methoxychlor.

(11) Other Insecticides:
machine oil, nicotine-sulfate; avermectin-B, bromopropylate, buprofezin, chlorphenapyr, cyromazine, D-D(1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, lepimectin, Arsenic acid, benclothiaz, Calcium cyanamide, Calcium polysulfide, chlordane, DDT, DSP, flufenerim, flonicamid, flurimfen, formetanate, metam-ammonium, metam-sodium, Methyl bromide, Potassium oleate, protrifenbute, spiromesifen, sulfoxaflor, Sulfur, metaflumizone, spirotetramat, pyrifluquinazone, spinetoram, tralopyril, flupyradifurone, chlorantraniliprole, cyantraniliprole, flubendiamide, the compound represented by formula (K):

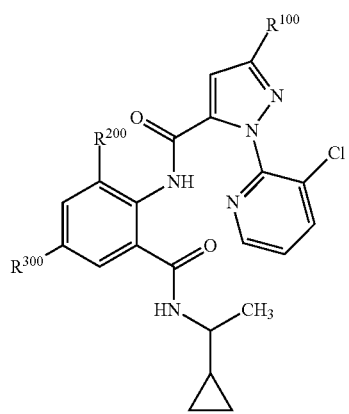

wherein
$R^{100}$ represents chlorine, bromine or a trifluoromethyl group,
$R^{200}$ represents chlorine, bromine or a methyl group, and
$R^{300}$ represents chlorine, bromine or a cyano group, and the compound represented by formula (L):

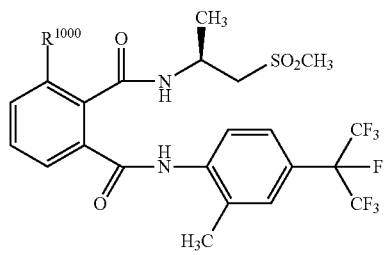

wherein
$R^{1000}$ represents chlorine, bromine or iodine.

Examples of active ingredients of the acaricides include: acequinocyl, amitraz, benzoximate, bifenaate, bromopropylate, chinomethionat, chlorobenzilate, CPCBS (chlorfenson), clofentezine, cyflumetofen, dicofol, etoxazole, fenbutatin oxide, fenothiocarb, fenpyroximate, fluacrypyrim, fluproxyfen, hexythiazox, propargite: BPPS, polynactins, pyridaben, Pyrimidifen, tebufenpyrad, tetradifon, spirodiclofen, spiromesifen, spirotetramat, amidoflumet, and cyenopyrafen.

Examples of active ingredients of the nematocides include: DCIP, fosthiazate, levamisol, methyisothiocyanate, morantel tartarate, and imicyafos.

Examples of active ingredients of the fungicides include:
(1) Azole Compounds:
triforine, imazalil, pefurazoate, prochloraz, triflumizole, bitertanol, bromuconazole, cyproconazole, difenoconazole, diniconazole-M, epoxiconazole, fenbuconazole, fluquinconazole, flusilazole, flutriafol, hexaconazole, ipconazole, metconazole, myclobutanil, penconazole, propiconazole, prothioconazole, tebuconazole, tetraconazole, triadimenol, triticonazole, and the like;

(2) Strobilurin Compounds:
azoxystrobin, kresoxim-methyl, metominostrobin, trifloxystrobin, picoxystrobin, pyraclostrobin, enestrobin, dimoxystrobin, orysastrobin, fluoxastrobin, famoxadone, fenamidone, pyribencarb, and the like;

(3) Other Active Ingredients of Fungicides:
carbendezim, benomyl, thiabendazole, thiophanate-methyl, zoxamide, diethofencarb, pencycuron, fluopicolide, carboxin, frutolanil, frametpyr, thifluzamide, boscalid, penthiopyrad, fluopyram, bixafen, isopyrazam, penflufen, sedaxan, fluxapyroxad, fluazinam, ferimzone, silthiofam, procymidone, iprodione, vinclozolin, metalaxyl, benalaxyl, pyrimethanil, mepanipyrim, cyprodinil, quinoxyfen, proquinazid, fenpiclonil, fludioxonil, fenhexamid, fenpropimorph, tridemorph, fenpropidin, spiroxamine, thiuram, ziram, mancozeb, chlorothalonil, dichlofluanid, captan, folpet, iminoctadine, ethaboxam, metrafenone, dodine, fthalide, tricyclazole, pyroquilon, carpropamid, diclocymet, fenoxanil, dimethomorph, iprovalicarb, benthiavalicarb, mandipropamid, tolclofos-methyl, quintozene, cyazofamid, amisulbrom, ametoctradin, cyflufenamid, validamycin A, polyoxin B, blastcidin-S, kasugamycin, oxolinic acid, and the like;

(4) Resistance Inducing Compounds:
acibenzolar-S-methyl, probenazole, isotianil and tiadinil.

Examples of active ingredients of the herbicides include:
(1) Phenoxyfatty Acid Herbicidal Compounds:
2,4-PA, MCP, MCPB, phenothiol, mecoprop, fluroxypyr, triclopyr, clomeprop, and naproanilide.

(2) Benzoic Acid Herbicidal Compounds:
2,3,6-TBA, dicamba, clopyralid, picloram, aminopyralid, quinclorac, and quinmerac.

(3) Urea Herbicidal Compounds:
diuron, linuron, chlortoluron, isoproturon, fluometuron, isouron, tebuthiuron, methabenzthiazuron, cumyluron, daimuron, and methyl-daimuron.

(4) Triazine Herbicidal Compounds:
atrazine, ametoryn, cyanazine, simazine, propazine, simetryn, dimethametryn, prometryn, metribuzin, triaziflam, and indaziflam.

(5) Bipyridinium Herbicidal Compounds:
paraquat, and diquat.

(6) Hydroxybenzonitrile Herbicidal Compounds:
bromoxynil, and ioxynil.

(7) Dinitroaniline Herbicidal Compounds:
pendimethalin, prodiamine, and trifluralin.

(8) Organic Phosphorus Herbicidal Compounds:
  amiprofos-methyl, butamifos, bensulide, piperophos, anilofos, glyphosate, glufosinate, glufosinate-P, and bialaphos.
(9) Carbamate Herbicidal Compounds:
  di-allate, tri-allate, EPTC, butylate, benthiocarb, esprocarb, molinate, dimepiperate, swep, chlorpropham, phenmedipham, phenisopham, pyributicarb, and asulam.
(10) Acid Amide Herbicidal Compounds:
  propanil, propyzamide, bromobutide, and etobenzanid.
(11) Chloroacetanilide Herbicidal Compounds:
  acetochlor, alachlor, butachlor, dimethenamid, propachlor, metazachlor, metolachlor, pretilachlor, thenylchlor, and pethoxamid.
(12) Diphenylether Herbicidal Compounds:
  acifluorfen-sodium, bifenox, oxyfluorfen, lactofen, fomesafen, chlomethoxynil, and aclonifen.
(13) Cyclic Imide Herbicidal Compounds:
  oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, bencarbazone, and saflufenacil.
(14) Pyrazole Herbicidal Compounds:
  benzofenap, pyrazolate, pyrazoxyfen, topramezone, and pyrasulfotole.
(15) Triketone Herbicidal Compounds:
  isoxaflutole, benzobicyclon, sulcotrione, mesotrione, tembotrione, and tefuryltrione.
(16) Aryloxyphenoxypropionic Acid Herbicidal Compounds:
  clodinafop-propargyl, cyhalofop-butyl, diclofop-methyl, fenoxaprop-ethyl, fluazifop-butyl, haloxyfop-methyl, and quizalofop-ethyl, metamifop.
(17) Trioneoxime Herbicidal Compounds:
  alloxydim-sodium, sethoxydim, butroxydim, clethodim, cloproxydim, cycloxydim, tepraloxydim, tralkoxydim, and profoxydim.
(18) Sulfonylurea Herbicidal Compounds:
  chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, and propyrisulfuron.
(19) Imidazolinone Herbicidal Compounds:
  imazamethabenz-methyl, imazamethapyr, imazamox, imazapyr, imazaquin, and imazethapyr.
(20) Sulfonamide Herbicidal Compounds:
  flumetsulam, metosulam, diclosulam, florasulam, cloransulam-methyl, penoxsulam, and pyroxsulam.
(21) Pyrimidinyloxybenzoic Acid Herbicidal Compounds:
  pyrithiobac-sodium, bispyribac-sodium, pyriminobac-methyl, pyribenzoxim, pyriftalid, and pyrimisulfan.
(22) Other Herbicidal Compounds
  bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone, and methiozolin.

Examples of active ingredients of the synergists include: piperonyl butoxide, sesamex, sulfoxide, N-(2-ethylhexyl)-8,9,10-trinorborn-5-ene-2,3-dicarboximide (MGK 264), N-declyimidazole, WARF-antiresistant, TBPT, TPP, IBP, PSCP, methyl iodide ($CH_3I$), t-phenylbutenone, diethylmaleate, DMC, FDMC, ETP, and ETN.

EXAMPLES

Hereinafter, the present invention will be described in more detail with reference to Production Examples, Formulation Examples and Test Examples, but not limited thereto.

Firstly, Production Examples of the present compound are described below.

Production Example 1(1)

To a mixture of 3-chloro-2-cyanopyridine (1.39 g), ethyl mercaptan (0.9 ml) and DMF (10 ml) was added sodium hydride (60%, oil) (0.52 g) under ice cooling, and then the mixture was stirred for one hour at room temperature. After that, water was added to the reaction mixture, and the mixture was extracted with ethyl acetate. The resultant organic layer was washed with a saturated aqueous sodium bicarbonate solution, followed by a saturated brine, dried on anhydrous sodium sulfate, and concentrated under reduced pressure. The residue was subjected to silica gel column chromatography to give 2-cyano-3-ethylsulfanylpyridine (1.52 g).

2-cyano-3-ethylsulfanylpyridine:

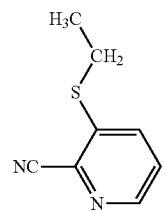

$^1$H-NMR ($CDCl_3$) δ: 8.49 (1H, dd), 7.75 (1H, dd), 7.43 (1H, dd), 3.06 (2H, q), 1.38 (3H, t).

Production Example 1(2)

To a mixture of concentrated sulfuric acid (15 ml) and water (5 ml) was added 2-cyano-3-ethylsulfanylpyridine (1.4 g), and then the mixture was stirred at 130° C. for 2 hours. After allowing the reaction mixture to cool to room temperature, to the reaction mixture was added an aqueous potassium hydroxide solution, and then the mixture was extracted with ethyl acetate. To the resultant aqueous layer was added concentrated hydrochloric acid, and then the mixture was extracted with chloroform, dried on anhydrous sodium sulfate, and concentrated under reduced pressure to give 3-ethylsulfanylpicolinic acid (1.15 g).

3-ethylsulfanylpicolinic acid:

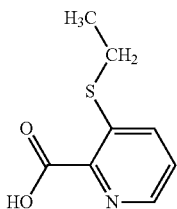

$^1$H-NMR(CDCl$_3$) δ: 8.31 (1H, d), 7.75 (1H, d), 7.49 (1H, dd), 2.97 (2H, q), 1.44 (3H, t).

Production Example 1(3)

A mixture of 2-amino-4-(trifluoromethylsulfanyl)phenol (1.0 g), which had been synthesized by a process described in WO2009-131237, 3-ethylsulfanylpicolinic acid (0.87 g), EDCI hydrochloride (1.10 g) and chloroform (10 ml) was stirred for 30 minutes at room temperature. To the reaction mixture was added water, and the mixture was extracted with ethyl acetate. The organic layer was washed with a saturated aqueous sodium bicarbonate solution, followed by a saturated brine, and dried on anhydrous magnesium sulfate, and then concentrated under reduced pressure. The residue was subjected to silica gel column chromatography to give 3-ethylsulfanyl-N-[2-hydroxy-5-(trifluoromethylsulfanyl)phenyl]picolinamide (hereinafter referred to as "the intermediate compound M4-6") (1.32 g).
The Intermediate Compound M4-6:

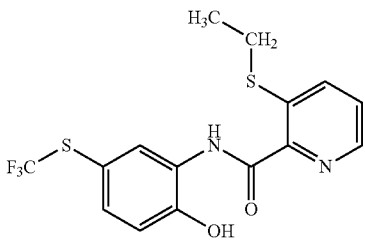 [SMILES: CCSc1cccnc1C(=O)Nc1cc(SC(F)(F)F)ccc1O]

$^1$H-NMR (CDCl$_3$) δ: 10.40 (1H, brs), 9.63 (1H, s), 8.36 (1H, dd), 7.75 (1H, dd), 7.53 (1H, d), 7.45 (1H, dd), 7.41 (1H, dd), 7.08 (1H, d), 2.97 (2H, q), 1.44 (3H, t).

Production Example 1(4)

A mixture of the intermediate compound M4-6 (1.23 g), di-2-methoxyethyl azodicarboxylate (hereinafter referred to as "DMEAD") (1.28 g), triphenylphosphine (1.39 g) and THF (30 ml) was stirred for one hour at room temperature followed by one hour at 50° C. After allowing the reaction mixture to cool to room temperature, the reaction mixture was concentrated under reduced pressure. Water was poured to the mixture, and then the mixture was extracted with ethyl acetate. The organic layer was washed with a saturated aqueous sodium bicarbonate solution, followed by a saturated brine, and dried on anhydrous magnesium sulfate, and then concentrated under reduced pressure. The residue was subjected to silica gel column chromatography to give 2-(3-ethylsulfanylpyridine-2-yl)-5-(trifluoromethylsulfanyl)benzoxazole (hereinafter referred to as "the present compound 1-6") (1.21 g).

The Present Compound 1-6:

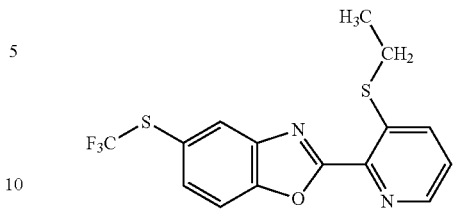

$^1$H-NMR (CDCl$_3$) δ: 8.59 (1H, dd), 8.27 (1H, s), 7.78 (1H, dd), 7.75-7.69 (2H, m), 7.42 (1H, dd), 3.07 (2H, q), 1.47 (3H, t).

Production Example 2

To a mixture of the present compound 1-6 (1.06 g) and chloroform (30 ml) was added m-chloroperbenzoic acid (purity: 65% or more, 1.47 g) under ice cooling, and then the mixture was stirred for 6 hours at room temperature. To the reaction mixture was added 10% aqueous sodium sulfite solution, and then the mixture was extracted with chloroform. The organic layer was washed with a saturated aqueous sodium bicarbonate solution, and dried on anhydrous magnesium sulfate, and concentrated under reduced pressure. The residue was subjected to silica gel column chromatography to give 2-(3-ethylsulfonylpyridin-2-yl)-5-(trifluoromethylsulfanyl)benzoxazole (hereinafter referred to as "the present compound 1-8") (0.87 g) and 2-(3-ethylsulfonylpyridin-2-yl)-5-(trifluoromethylsulfinyl)benzoxazole (hereinafter referred to as "the present compound 1-9") (0.17 g).
The Present Compound 1-8:

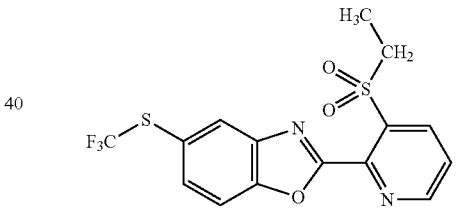

$^1$H-NMR (CDCl$_3$) δ: 9.03 (1H, dd), 8.60 (1H, dd), 8.19 (1H, d), 7.80-7.71 (3H, m), 4.02 (2H, q), 1.43 (3H, t).
The Present Compound 1-9:

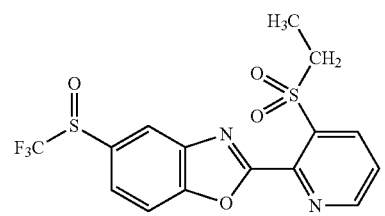 [SMILES: CCS(=O)(=O)c1cccnc1-c1nc2cc(S(=O)C(F)(F)F)ccc2o1]

$^1$H-NMR (CDCl$_3$) δ: 9.04 (1H, dd), 8.61 (1H, dd), 8.35 (1H, d), 7.96-7.86 (2H, m), 7.77 (1H, dd), 4.01 (2H, q), 1.44 (3H, t).

Production Example 3

To a mixture of the present compound 1-8 (0.35 g) and chloroform (8 ml) was added m-chloroperbenzoic acid (purity: 65% or more, 0.43 g) under ice cooling, and then the mixture was stirred at 40° C. for 6 hours. After allowing the reaction mixture to cool to room temperature, to the reaction mixture was added 10% aqueous sodium sulfite solution, and then the mixture was extracted with chloroform. The organic layer was washed with a saturated aqueous sodium bicarbonate solution, and dried on anhydrous magnesium sulfate, and then concentrated under reduced pressure. To the resultant residue were added acetonitrile (4 ml), sodium tungstate dihydrate (30 mg) and 30% hydrogen peroxide solution (4 ml), and then the mixture was stirred at 80° C. for 6 hours. After allowing the reaction mixture to cool to room temperature, to the reaction mixture was added water, the precipitated solid was collected by filtration. Then, 10% aqueous sodium sulfite solution was added to the precipitated solid, and the mixture was extracted with ethyl acetate. The organic layer was washed with water and a saturated brine, dried on anhydrous magnesium sulfate, and concentrated under reduced pressure. The residue was subjected to silica gel column chromatography to give 2-(3-ethylsulfonylpyridin-2-yl)-5-(trifluoromethylsulfonyl)benzoxazole (hereinafter referred to as "the present compound 1-10") (0.35 g).

The Present Compound 1-10:

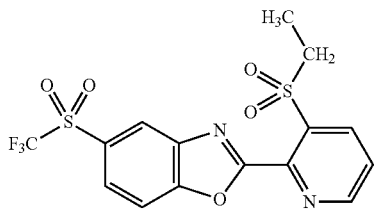 [SMILES: CCS(=O)(=O)c1cccnc1-c1nc2cc(S(=O)(=O)C(F)(F)F)ccc2o1]

¹H-NMR (CDCl₃) δ: 9.05 (1H, dd), 8.61 (1H, dd), 8.59 (1H, d), 8.17 (1H, dd), 7.96 (1H, d), 7.80 (1H, dd), 3.98 (2H, q), 1.45 (3H, t).

Production Example 4(1)

A mixture of 2-amino-4-(trifluoromethylsulfanyl)phenol (1.0 g), 3-chloro-5-trifluoromethylpicolinic acid (1.08 g), EDCI hydrochloride (1.10 g) and chloroform (10 ml) was stirred at room temperature for one hour. To the reaction mixture was added water, and the mixture was extracted with ethyl acetate. The organic layer was washed with a saturated aqueous sodium bicarbonate solution, water and a saturated brine, dried on anhydrous magnesium sulfate, and concentrated under reduced pressure to give 3-chloro-5-trifluoromethyl-N-[2-hydroxy-5-(trifluoromethylsulfanyl)phenyl]picolinamide (hereinafter referred to as "the intermediate compound M10-40") (1.94 g).

The Intermediate Compound M10-40:

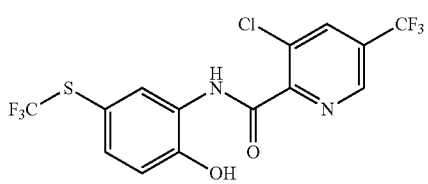 [SMILES: O=C(Nc1cc(SC(F)(F)F)ccc1O)c1ncc(C(F)(F)F)cc1Cl]

¹H-NMR(CDCl₃) δ: 8.78 (1H, d), 8.15 (1H, d), 8.09 (1H, d), 7.37 (1H, dd), 7.04 (1H, d).

Production Example 4(2)

To a mixture of the intermediate compound M10-40 (1.93 g), DMF (6 ml), THF (1 ml) and ethyl mercaptan (0.38 ml) was added potassium tert-butoxide (0.62 g) under ice cooling, and then the mixture was stirred for 2 hours at room temperature. To the reaction mixture was added water, and the mixture was extracted with ethyl acetate. The organic layer was washed with water and a saturated brine, dried on anhydrous magnesium sulfate, and concentrated under reduced pressure. The residue was subjected to silica gel column chromatography to give 3-ethylsulfanyl-5-trifluoromethyl-N-[2-hydroxy-5-(trifluoromethylsulfanyl)phenyl]picolinamide (hereinafter referred to as "the intermediate compound M4-16") (1.45 g).

The Intermediate Compound M4-16

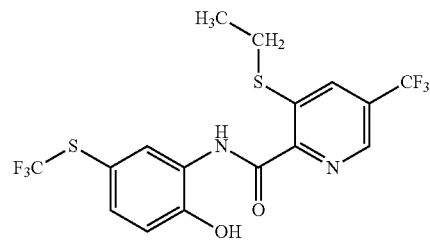 [SMILES: CCSc1cc(C(F)(F)F)cnc1C(=O)Nc1cc(SC(F)(F)F)ccc1O]

¹H-NMR (CDCl₃) δ: 10.31 (1H, s), 8.96 (1H, brs), 8.58 (1H, d), 7.91 (1H, d), 7.70 (1H, d), 7.43 (1H, dd), 7.07 (1H, d), 3.00 (2H, q), 1.47 (3H, t).

Production Example 4(3)

A mixture of the intermediate compound M4-16 (1.45 g), DMEAD (1.19 g), triphenylphosphine (1.29 g) and THF (30 ml) was stirred for one hour at room temperature followed by one hour at 50° C. After allowing the reaction mixture to cool to room temperature, the reaction mixture was concentrated under reduced pressure and water was added thereto. Then, the mixture was extracted with ethyl acetate. The organic layer was washed with a saturated aqueous sodium bicarbonate solution, followed by a saturated brine, dried on anhydrous magnesium sulfate, and concentrated under reduced pressure. The residue was subjected to silica gel column chromatography to give 2-(3-ethylsulfanyl-5-trifluoromethylpyridine-2-yl)-5-(trifluoromethylsulfanyl)benzoxazole (hereinafter referred to as "the present compound 1-16") (1.31 g).

The Present Compound 1-16

¹H-NMR (CDCl₃) δ: 8.78 (1H, d), 8.30 (1H, s), 7.94 (1H, d), 7.77-7.75 (2H, m), 3.11 (2H, q), 1.51 (3H, t).

Production Example 5

To a mixture of the present compound 1-16 (1.13 g) and chloroform (25 ml) was added m-chloroperbenzoic acid (purity: 65% or more, 0.56 g) under ice cooling, and then the mixture was stirred for 40 minutes at 0° C. To the reaction mixture was added 10% aqueous sodium sulfite solution, and then the mixture was extracted with chloroform. The organic layer was washed with a saturated aqueous sodium bicarbonate solution, and dried on anhydrous magnesium sulfate, and concentrated under reduced pressure. The residue was subjected to silica gel column chromatography to give 2-(3-ethylsulfinyl-5-trifluoromethylpyridine-2-yl)-5-(trifluoromethylsulfanyl)benzoxazole (hereinafter referred to as "the present compound 1-17") (1.01 g).

The Present Compound 1-17

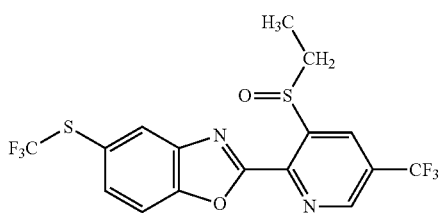 [SMILES: CCS(=O)c1cc(C(F)(F)F)cnc1-c1nc2cc(SC(F)(F)F)ccc2o1]

$^1$H-NMR (CDCl$_3$) δ: 9.13 (1H, d), 8.91 (1H, d), 8.25 (1H, s), 7.85-7.79 (2H, m), 3.60-3.49 (1H, m), 3.13-3.02 (1H, m), 1.44 (3H, t).

Production Example 6

To a mixture of the present compound 1-17 (1.01 g) and chloroform (20 ml) was added m-chloroperbenzoic acid (purity: 65% or more, 0.56 g) under ice cooling, and then the mixture was stirred for 6 hours at room temperature. Further, m-chloroperbenzoic acid (purity: 65% or more, 0.20 g) was added to the reaction mixture, and then the mixture was stirred for 3 hours at room temperature. To the reaction mixture was added 10% aqueous sodium sulfite solution, and then the mixture was extracted with chloroform. The organic layer was washed with a saturated aqueous sodium bicarbonate solution, and dried on anhydrous magnesium sulfate, and concentrated under reduced pressure. The residue was subjected to silica gel column chromatography to give 2-(3-ethylsulfonyl-5-trifluoromethylpyridine-2-yl)-5-(trifluoromethylsulfanyl)benzoxazole (hereinafter referred to as "the present compound 1-18") (0.53 g) and 2-(3-ethylsulfonyl-5-trifluoromethylpyridine-2-yl)-5-(trifluoromethylsulfinyl)benzoxazole (hereinafter referred to as "the present compound 1-19") (0.48 g).

The Present Compound 1-18:

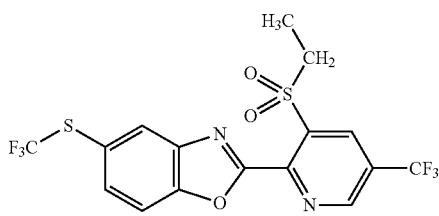 [SMILES: CCS(=O)(=O)c1cc(C(F)(F)F)cnc1-c1nc2cc(SC(F)(F)F)ccc2o1]

$^1$H-NMR (CDCl$_3$) δ: 9.25 (1H, d), 8.84 (1H, d), 8.22 (1H, d), 7.82 (1H, dd), 7.77 (1H, d), 4.11 (2H, q), 1.47 (3H, t).

The Present Compound 1-19:

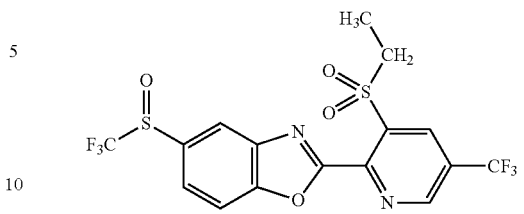

$^1$H-NMR (CDCl$_3$) δ: 9.27 (1H, d), 8.85 (1H, d), 8.39 (1H, s), 7.96 (1H, d), 7.92 (1H, d), 4.09 (2H, q), 1.48 (3H, t).

Production Example 7

A mixture of the present compound 1-19 (0.26 g), acetonitrile (4 ml), sodium tungstate dihydrate (18 mg) and 30% hydrogen peroxide solution (3.5 ml) was stirred for 5 hours at 85° C. After allowing the reaction mixture to cool to room temperature, to the reaction mixture was added 30% hydrogen peroxide solution (0.5 ml), and then the mixture was stirred for 3 hours at 85° C. After allowing the reaction mixture to cool to room temperature, to the reaction mixture was added water, the precipitated solid was collected by filtration. To the solid was added 10% aqueous sodium sulfite solution, and the mixture was extracted with ethyl acetate. The organic layer was washed with water and a saturated brine, dried on anhydrous magnesium sulfate, and concentrated under reduced pressure. The residue was subjected to silica gel column chromatography to give 2-(3-ethylsulfonyl-5-trifluoromethylpyridine-2-yl)-5-(trifluoromethylsulfonyl)benzoxazole (hereinafter referred to as "the present compound 1-20") (0.24 g).

The Present Compound 1-20:

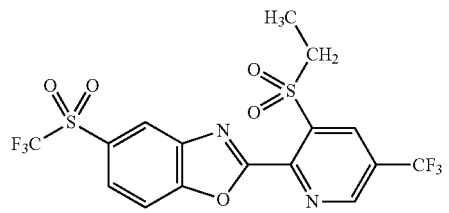 [SMILES: CCS(=O)(=O)c1cc(C(F)(F)F)cnc1-c1nc2cc(S(=O)(=O)C(F)(F)F)ccc2o1]

$^1$H-NMR (CDCl$_3$) δ: 9.28 (1H, d), 8.84 (1H, d), 8.62 (1H, d), 8.21 (1H, dd), 8.00 (1H, d), 4.05 (2H, q), 1.49 (3H, t).

Production Example 8(1)

A mixture of tert-butanol (27 ml) and potassium hydroxide (3.15 g) was stirred for one hour under reflux with heating. To the mixture were added 2-chloro-5-trifluoromethylsulfanylpyridine (6.0 g), which had been synthesized by a process described in WO2012-086848, and tert-butanol (3 mL) with a dropping funnel. The mixture was stirred for 5 hours under reflux with heating. After allowing the reaction mixture to cool to room temperature, to the reaction mixture was added concentrated hydrochloric acid. The precipitated solid was filtrated and washed with ethanol. The resultant filtrate was concentrated under reduced pressure, and 1N hydrochloric acid was added thereto. Then, the precipitated solid was collected by filtration, washed with water, followed by hexane, and then dried to give 2-hydroxy-5-trifluoromethylsulfanylpyridine (4.42 g).

2-hydroxy-5-trifluoromethylsulfanylpyridine:

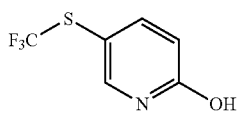

¹H-NMR (CDCl₃) δ: 7.73 (1H, d), 7.62 (1H, dd), 6.61 (1H, d).

Production Example 8(2)

To a mixture of 2-hydroxy-5-trifluoromethylsulfanylpyridine (2 g) and concentrated sulfuric acid (10 mL) was added fuming nitric acid (0.74 mL) under ice cooling, and then the mixture was stirred for 2 hours at 60° C. After allowing the reaction mixture to cool to room temperature, the reaction mixture was poured into an ice-water (50 mL), and the mixture was extracted with ethyl acetate. The organic layer was washed with a saturated brine, dried on anhydrous sodium sulfate, and concentrated under reduced pressure. The resultant solid was washed with tert-butylmethylether to give 2-hydroxy-3-nitro-5-trifluoromethylsulfinylpyridine (2.13 g).
2-hydroxy-3-nitro-5-trifluoromethylsulfinylpyridine:

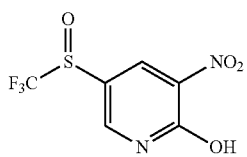 [SMILES: Nc1cc(S(=O)C(F)(F)F)cnc1O]

¹H-NMR (DMSO-D₆) δ: 8.67 (1H, brs), 8.59 (1H, brs).

Production Example 8(3)

A mixture of an iron powder (4.6 g), acetic acid (0.5 mL), ethanol (20 mL) and water (15 mL) was stirred at 70° C., and then 2-hydroxy-3-nitro-5-trifluoromethylsulfinylpyridine (2 g) was added thereto and the mixture was stirred for 2 hours at 70° C. After allowing the reaction mixture to cool to room temperature, the reaction mixture was filtered through Celite®. The resultant filtrate was concentrated under reduced pressure, a saturated aqueous sodium bicarbonate solution was added thereto, and the mixture was extracted with ethyl acetate. The organic layer was dried on anhydrous sodium sulfate, and concentrated under reduced pressure. The resultant solid was washed with tert-butylmethylether to give 3-amino-2-hydroxy-5-trifluoromethylsulfinylpyridine (1.45 g).
3-amino-2-hydroxy-5-trifluoromethylsulfinylpyridine:

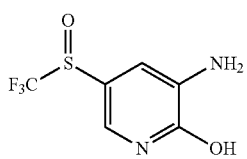

¹H-NMR (DMSO-D₆) δ: 12.23 (1H, brs), 7.49 (1H, s), 6.68 (1H, s), 5.72 (2H, brs).

Production Example 8(4)

A mixture of 3-amino-2-hydroxy-5-trifluoromethylsulfinylpyridine (0.63 g), 3-ethylsulfanylpicolinic acid (0.55 g), EDCI hydrochloride (0.68 g) and pyridine (20 ml) was stirred for 3 hours at room temperature. Water was poured to the reaction mixture, and the mixture was stirred for 30 minutes at room temperature. The precipitated solid was collected by filtration, and dried under reduced pressure to give 3-ethylsulfanyl-N-[2-hydroxy-5-trifluoromethylsulfinylpyridine-3-yl]picolinamide (hereinafter referred to as "the intermediate compound M4-61") (0.73 g).
The Intermediate Compound M4-61:

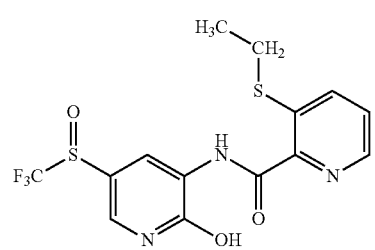 [SMILES: CCSc1cccnc1C(=O)Nc1cc(S(=O)C(F)(F)F)cnc1O]

¹H-NMR (DMSO-D₆) δ: 10.83 (1H, s), 8.71 (1H, s), 8.48 (1H, dd), 8.09 (1H, d), 7.98 (1H, d), 7.65 (1H, dd), 2.99 (2H, q), 1.31 (3H, t).

Production Example 8(5)

A mixture of the intermediate compound M4-61 (0.67 g), DMEAD (0.64 g), triphenylphosphine (0.68 g) and THF (40 ml) was stirred for 3 hours at 50° C. After allowing the reaction mixture to cool to room temperature, the reaction mixture was concentrated under reduced pressure and water was added thereto. Then, the mixture was extracted with ethyl acetate. The organic layer was washed with a saturated aqueous ammonium chloride solution and a saturated brine, dried on anhydrous sodium sulfate, and concentrated under reduced pressure. The residue was subjected to silica gel column chromatography to give 2-(3-ethylsulfanylpyridine-2-yl)-6-(trifluoromethylsulfinyl)oxazolo[5,4-b]pyridine (hereinafter referred to as "the present compound 1-61") (0.59 g).
The Present Compound 1-61:

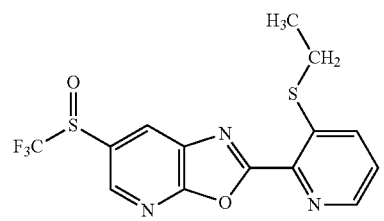 [SMILES: CCSc1cccnc1-c1nc2cc(S(=O)C(F)(F)F)cnc2o1]

¹H-NMR (CDCl₃) δ: 8.76 (1H, d), 8.70 (1H, d), 8.64 (1H, dd), 7.82 (1H, dd), 7.47 (1H, dd), 3.09 (2H, q), 1.47 (3H, q).

Production Example 9

To a mixture of the present compound 1-61 (0.43 g) and chloroform (30 ml) was added m-chloroperbenzoic acid (purity: 65% or more, 0.53 g) under ice cooling, and then the mixture was stirred for 5 hours at room temperature. To the reaction mixture was added 10% aqueous sodium sulfite solution, and then the mixture was extracted with chloroform. The organic layer was washed with a saturated aqueous sodium bicarbonate solution, and dried on anhydrous sodium sulfate, and concentrated under reduced pressure. The residue was subjected to silica gel column chromatography to give 2-(3-ethylsulfonylpyridin-2-yl)-6-(trifluoromethylsulfinyl)oxazolo[5,4-b]pyridine (hereinafter referred to as "the present compound 1-4") (0.34 g).

The Present Compound 1-4:

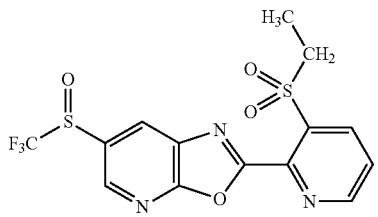 [SMILES: CCS(=O)(=O)c1cccnc1-c1nc2cc(S(=O)C(F)(F)F)cnc2o1]

$^1$H-NMR (CDCl$_3$) δ: 9.08 (1H, dd), 8.80 (1H, d), 8.69 (1H, d), 8.60 (1H, dd), 7.81 (1H, dd), 3.91 (2H, q), 1.45 (3H, t).

Production Example 10

A mixture of the present compound 1-4 (0.17 g), acetonitrile (4 ml), sodium tungstate dihydrate (14 mg) and 30% hydrogen peroxide solution (4 ml) was stirred for 4 hours at 80° C. After allowing the reaction mixture to cool to room temperature, water was added thereto. The precipitated solid was collected by filtration, and 10% aqueous sodium sulfite solution was added to the solid. Then, the mixture was extracted with ethyl acetate. The organic layer was washed with water and a saturated brine, dried on anhydrous sodium sulfate, and concentrated under reduced pressure. The residue was subjected to silica gel column chromatography to give 2-(3-ethylsulfonylpyridin-2-yl)-6-(trifluoromethylsulfonyl)oxazolo[5,4-b]pyridine (hereinafter referred to as "the present compound 1-5") (0.09 g).

The Present Compound 1-5:

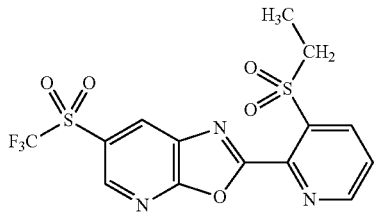 [SMILES: CCS(=O)(=O)c1cccnc1-c1nc2cc(S(=O)(=O)C(F)(F)F)cnc2o1]

$^1$H-NMR (CDCl$_3$) δ: 9.13 (1H, d), 9.09 (1H, dd), 8.79 (1H, d), 8.60 (1H, dd), 7.83 (1H, dd), 3.88 (2H, q), 1.46 (3H, t).

Production Example 11(1)

To a mixture of 3-chloro-2-cyano-5-trifluoromethylpyridine (10.0 g), ethyl mercaptan (4.38 ml) and DMF (40 ml) was added sodium hydride (60%, oil) (2.53 g) under ice cooling, and then the mixture was stirred for 2 hours at room temperature. To the reaction mixture was added water, and the mixture was extracted with ethyl acetate. The organic layer was washed with a saturated aqueous sodium bicarbonate solution, followed by a saturated brine, dried on anhydrous sodium sulfate, and concentrated under reduced pressure. The residue was subjected to silica gel column chromatography to give 2-cyano-3-ethylsulfanyl-5-trifluoromethylpyridine (9.25 g).

2-cyano-3-ethylsulfanyl-5-trifluoromethylpyridine:

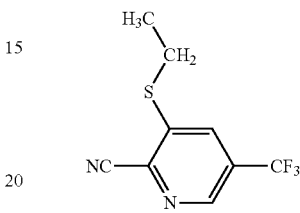

$^1$H-NMR (CDCl$_3$) δ: 8.68 (1H, s), 7.88 (1H, s), 3.13 (2H, q), 1.44 (3H, t).

Production Example 11(2)

To a mixture of concentrated sulfuric acid (30 ml) and water (10 ml) was added 2-cyano-3-ethylsulfanyl-5-trifluoromethylpyridine (6.0 g), and then the mixture was stirred for 2 hours at 130° C. After allowing the reaction mixture to cool to room temperature, the reaction mixture was cooled with ice, water (200 ml) was added thereto and then the mixture was stirred for 30 minutes at room temperature. The precipitated solid was collected by filtration, washed with water, and dried under reduced pressure to give 3-ethylsulfanyl-5-trifluoromethylpicolinic acid (6.74 g).

3-ethylsulfanyl-5-trifluoromethylpicolinic acid:

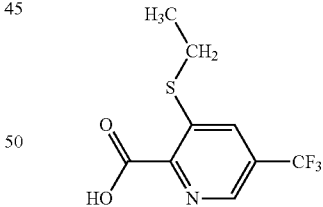

$^1$H-NMR (CDCl$_3$) δ: 8.55 (1H, s), 7.92 (1H, s), 3.02 (2H, d), 1.47 (3H, t).

Production Example 11(3)

A mixture of 3-amino-2-hydroxy-5-trifluoromethylsulfinylpyridine (0.67 g), 3-ethylsulfanyl-5-trifluoromethylpicolinic acid (0.75 g), EDCI hydrochloride (0.68 g) and pyridine (20 ml) was stirred for 1.5 hours at room temperature. Water was poured to the reaction mixture, and then the mixture was stirred for 15 minutes at room temperature. The precipitated solid was collected by filtration, and dried under reduced pressure to give 3-ethylsulfanyl-5-trifluoromethyl-N-[2-hydroxy-5-trifluoromethylsulfinylpyridine-3-yl]picolinamide (hereinafter referred to as "the intermediate compound M4-65") (1.28 g).

The Intermediate Compound M4-65:

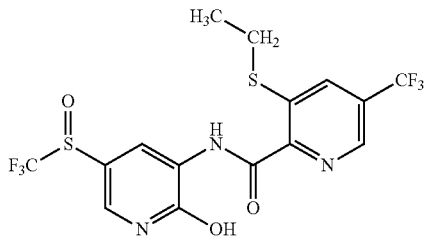 [SMILES: CCSc1cc(C(F)(F)F)cnc1C(=O)Nc1cc(S(=O)C(F)(F)F)cnc1O]

$^1$H-NMR (CDCl$_3$) δ: 10.99 (1H, s), 8.90 (1H, s), 8.68 (1H, s), 7.91 (1H, s), 7.81 (1H, s), 3.02 (2H, q), 1.48 (3H, t).

Production Example 11(4)

A mixture of the intermediate compound M4-65 (1.24 g), DMEAD (1.01 g), triphenylphosphine (1.06 g) and THF (40 ml) was stirred for 3 hours at 50° C. After allowing the reaction mixture to cool to room temperature, the reaction mixture was concentrated under reduced pressure and water was added thereto. Then, the mixture was extracted with ethyl acetate. The organic layer was washed with a saturated aqueous ammonium chloride solution and a saturated brine, dried on anhydrous sodium sulfate, and concentrated under reduced pressure. The residue was subjected to silica gel column chromatography to give 2-(3-ethylsulfanyl-5-trifluoromethylpyridine-2-yl)-6-(trifluoromethylsulfinyl)oxazolo[5,4-b]pyridine (hereinafter referred to as "the present compound 1-65") (0.94 g).

The Present Compound 1-65:

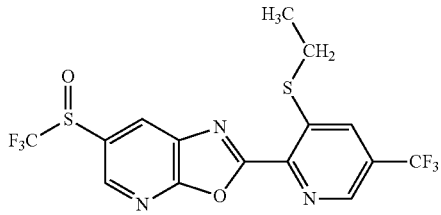 [SMILES: CCSc1cc(C(F)(F)F)cnc1-c1nc2cc(S(=O)C(F)(F)F)cnc2o1]

$^1$H-NMR (CDCl$_3$) δ: 8.83 (1H, d), 8.81 (1H, d), 8.75 (1H, d), 7.97 (1H, d), 3.13 (2H, q), 1.51 (3H, t).

Production Example 12

To a mixture of the present compound 1-65 (0.74 g) and chloroform (30 ml) was added m-chloroperbenzoic acid (purity: 65% or more, 0.77 g) under ice cooling, and then the mixture was stirred for 4 hours at room temperature. To the reaction mixture was added 10% aqueous sodium sulfite solution, and then the mixture was extracted with chloroform. The organic layer was washed with a saturated aqueous sodium bicarbonate solution, and dried on anhydrous sodium sulfate, and concentrated under reduced pressure.

The residue was subjected to silica gel column chromatography to give 2-(3-ethylsulfonyl-5-trifluoromethylpyridine-2-yl)-6-(trifluoromethylsulfinyl)oxazolo[5,4-b]pyridine (hereinafter referred to as "the present compound 1-14") (0.75 g).

The Present Compound 1-14:

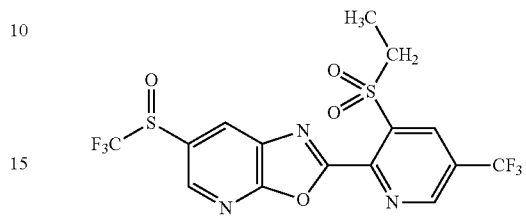

$^1$H-NMR (CDCl$_3$) δ: 9.31 (1H, d), 8.84-8.81 (2H, m), 8.73 (1H, d), 3.98 (2H, q), 1.49 (3H, t).

Production Example 13

A mixture of the present compound 1-14 (0.38 g), acetonitrile (4 ml), sodium tungstate dihydrate (27 mg) and 30% hydrogen peroxide solution (4 ml) was stirred for 4.5 hours at 80° C. After allowing the reaction mixture to cool to room temperature, water was added to thereto. Then, the precipitated solid was collected by filtration, 10% aqueous sodium sulfite solution was added thereto, and then the mixture was extracted with ethyl acetate. The organic layer was washed with water and a saturated brine, dried on anhydrous sodium sulfate, and concentrated under reduced pressure. The residue was subjected to silica gel column chromatography to give 2-(3-ethylsulfonyl-5-trifluoromethylpyridine-2-yl)-6-(trifluoromethylsulfonyl)oxazolo[5,4-b]pyridine (hereinafter referred to as "the present compound 1-15") (0.21 g).

The Present Compound 1-15:

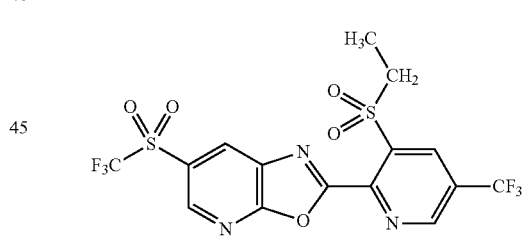

$^1$H-NMR (CDCl$_3$) δ: 9.32 (1H, d), 9.17 (1H, d), 8.85-8.82 (2H, m), 3.95 (2H, q), 1.50 (3H, t).

Production Example 14(1)

To a mixture of 4-(trifluoromethylsulfanyl)phenol (4.85 g) and chloroform (100 ml) was added m-chloroperbenzoic acid (purity: 65% or more, 6.33 g) under ice cooling, and then the mixture was stirred for 4 hours under ice cooling. To the reaction mixture was added 10% aqueous sodium sulfite solution, and then the mixture was extracted with ethyl acetate. The organic layer was washed with a saturated aqueous sodium bicarbonate solution, and dried on anhydrous magnesium sulfate, and concentrated under reduced pressure. The resultant solid was collected by filtration, washed with hexane to give 4-(trifluoromethylsulfinyl)phenol (5.16 g).

4-(trifluoromethylsulfinyl)phenol:

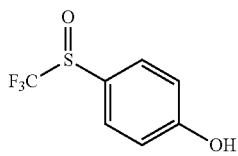

$^1$H-NMR (CDCl$_3$) δ: 7.70 (2H, d), 7.06 (2H, d).

4-(trifluoromethylsulfinyl)phenol could also be produced by following method:

To a mixture of 4-(trifluoromethylsulfanyl)phenol (5.0 g) and 50% sulfuric acid (10.1 g) was added 35% hydrogen peroxide solution (1.26 g) at 70° C., and then the mixture was stirred for 1 hour at 70° C. To the reaction mixture was added 35% hydrogen peroxide solution (0.50 g) at 70° C., and then the mixture was stirred for 1 hour at 70° C. To the reaction mixture was added 35% hydrogen peroxide solution (0.26 g) at 70° C., and then the mixture was stirred for 1 hour at 70° C. To the reaction mixture was added 35% hydrogen peroxide solution (0.6 g) at 70° C., and then the mixture was stirred for 30 minutes at 70° C. After allowing the reaction mixture to cool to room temperature, sodium bicarbonate solution was added to thereto. And then the mixture was extracted with ethyl acetate, and dried on anhydrous magnesium sulfate, and concentrated under reduced pressure. The resultant solid was collected by filtration, washed with hexane to give 4-(trifluoromethylsulfinyl)phenol (4.62 g, purity: 93.6% calculated by area percentage of LC).

Production Example 14(2)

To a mixture of 4-(trifluoromethylsulfinyl)phenol (0.42 g) and acetic acid (4 ml) were added nitric acid (0.29 g) and concentrated sulfuric acid (160 µl), and then the mixture was stirred for 8 hours at room temperature. A ice-water was poured to the reaction mixture, and the precipitated solid was collected by filtration. The solid was washed with water and dried under reduced pressure to give 2-nitro-4-(trifluoromethylsulfinyl)phenol (0.28 g).

2-nitro-4-(trifluoromethylsulfinyl)phenol:

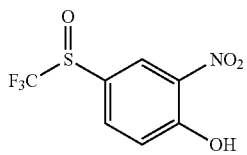 [SMILES: O=[N+]([O-])c1cc(S(=O)C(F)(F)F)ccc1O]

$^1$H-NMR (CDCl$_3$) δ: 10.97 (1H, s), 8.59 (1H, d), 8.00 (1H, dd), 7.45 (1H, d).

Production Example 14(3)

A mixture of 2-nitro-4-(trifluoromethylsulfinyl)phenol (5.0 g), palladium carbon (Pd 5%) (0.50 g) and ethanol (65 ml) was stirred for 6 hours at 35° C. under hydrogen atmosphere. After allowing the reaction mixture to cool to room temperature, the reaction mixture was filtered through Celite®. Water was added to the filtrate, and then the mixture was extracted with ethyl acetate. The organic layer was washed with water, dried on anhydrous sodium sulfate, and concentrated under reduced pressure. The resultant solid was washed with chloroform to give 2-amino-4-(trifluoromethylsulfinyl)phenol (3.87 g).

2-amino-4-(trifluoromethylsulfinyl)phenol:

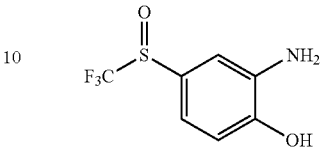

$^1$H-NMR (DMSO-D$_6$) δ: 10.30 (1H, brs), 7.06 (1H, d), 6.91 (1H, dd), 6.87 (1H, d), 5.18 (2H, brs).

Production Example 14(4)

To a mixture of 3-ethylsulfanylpicolinic acid (1.0 g), toluene (12 ml) and DMF (0.1 ml) was added thionyl chloride (0.8 ml) under ice cooling, and then the mixture was stirred at 100° C. for 4 hours. After allowing the reaction mixture to cool to room temperature, the reaction mixture was concentrated under reduced pressure. THF (8 ml) was added to the reaction mixture, and the mixture was added to a mixture of 2-amino-4-(trifluoromethylsulfinyl)phenol (1.23 g) and THF (12 ml), and stirred for 2 hours at room temperature. Water was added to the reaction mixture, and the mixture was extracted with ethyl acetate. The organic layer was washed with a saturated aqueous sodium bicarbonate solution and a saturated brine, dried on anhydrous sodium sulfate, and concentrated under reduced pressure to give 3-ethylsulfanyl-N-[2-hydroxy-5-(trifluoromethylsulfinyl)phenyl]picolinamide (hereinafter referred to as "the intermediate compound M4-63") (2.07 g).

The Intermediate Compound M4-63:

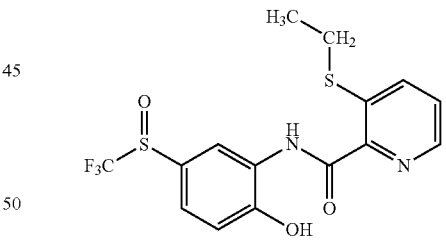

$^1$H-NMR (DMSO-D$_6$) δ: 10.67 (1H, s), 8.90 (1H, d), 8.48 (1H, dd), 7.97 (1H, dd), 7.64 (1H, dd), 7.52 (1H, dd), 7.22 (1H, d), 2.98 (2H, q), 1.31 (3H, t).

Production Example 14(5)

A mixture of the intermediate compound M4-63 (0.60 g), DMEAD (0.52 g), triphenylphosphine (0.56 g) and THF (12 ml) was stirred at 50° C. for 2.5 hours. After allowing the reaction mixture to cool to room temperature, the reaction mixture was concentrated under reduced pressure and water was added thereto. Then, the mixture was extracted with ethyl acetate. The organic layer was washed with a saturated aqueous ammonium chloride solution and a saturated brine, dried on anhydrous sodium sulfate, and concentrated under reduced pressure. The residue was subjected to silica gel column chromatography to give 2-(3-ethylsulfanylpyridine-2-yl)-5-(trifluoromethylsulfinyl)benzoxazole (hereinafter referred to as "the present compound 1-63") (0.51 g).

The Present Compound 1-63:

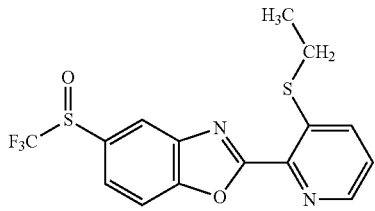 [SMILES: CCSc1cccnc1-c1nc2cc(S(=O)C(F)(F)F)ccc2o1]

$^1$H-NMR (CDCl$_3$) δ: 8.61 (1H, dd), 8.39 (1H, s), 7.93 (1H, d), 7.88 (1H, d), 7.81 (1H, dd), 7.45 (1H, dd), 3.08 (2H, q), 1.48 (3H, t).

Production Example 15

To a mixture of the present compound 1-8 (915 mg) and chloroform (8.5 ml) was added m-chloroperbenzoic acid (purity: 65% or more, 1.42 g), and then the mixture was stirred for 4 days at room temperature. To the reaction mixture was added 10% aqueous sodium thiosulfate solution and then the mixture was stirred for 10 minutes at room temperature. The organic layer was washed with a saturated aqueous sodium bicarbonate solution, followed by water and a saturated aqueous sodium chloride solution, dried on anhydrous magnesium sulfate, and concentrated under reduced pressure. The residue was subjected to silica gel column chromatography to give 2-(3-ethylsulfonyl-oxypyridine-2-yl)-5-(trifluoromethylsulfonyl)benzoxazole (hereinafter referred to as "the present compound 1-76") (117 mg).

The Present Compound 1-76:

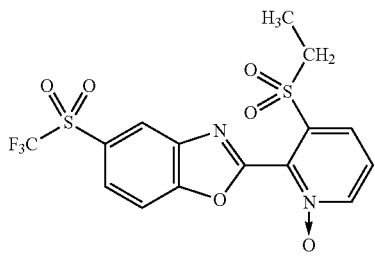 [SMILES: CCS(=O)(=O)c1ccc[n+]([O-])c1-c1nc2cc(S(=O)(=O)C(F)(F)F)ccc2o1]

$^1$H-NMR (CDCl$_3$) δ: 8.58 (1H, d), 8.54 (1H, dd), 8.18 (1H, dd), 7.99-7.93 (2H, m), 7.73 (1H, dd), 3.56 (2H, q), 1.38 (3H, t).

Production Example 16(1)

To a suspension of 3-ethylsulfonylpicolinic acid (1.00 g) in toluene (5 ml) was added DMF (0.003 g), and then thionyl chloride (1.12 g) was added dropwise thereto at room temperature. After that, the mixture was stirred at 75° C. for one hour, and then the solvent was removed by evaporation to give 3-ethylsulfonylpicolinic acid chloride (1.06 g).

3-ethylsulfonylpicolinic acid chloride:

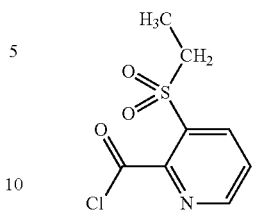

$^1$H-NMR (CDCl$_3$) δ: 8.94 (1H, dd), 8.42 (1H, dd), 7.73 (1H, dd), 3.47 (2H, q), 1.37 (3H, t).

To a solution of 2-amino-4-(trifluoromethylsulfinyl)phenol (0.93 g) in THF (5 ml) was added dropwise a solution of 3-ethylsulfonylpicolinic acid chloride in THF (2 ml) under ice cooling, and then the mixture was stirred for 18 hours at room temperature. The reaction mixture was quenched with water, neutralized by a saturated aqueous sodium bicarbonate solution, and then extracted with ethyl acetate. The organic layer was washed with a saturated aqueous sodium bicarbonate solution, followed by water and a saturated brine, and then the mixture was dried on anhydrous magnesium sulfate, and concentrated under reduced pressure. The resultant residue was subjected to silica gel column chromatography to give 3-ethylsulfonyl-N-[2-hydroxy-5-(trifluoromethylsulfinyl)phenyl]picolinamide (hereinafter referred to as "the intermediate compound M4-9") (1.50 g).

The Intermediate Compound M4-9:

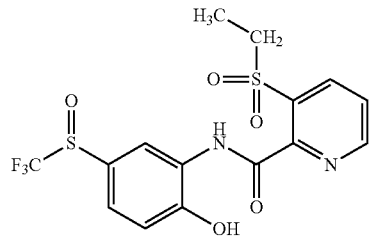 [SMILES: CCS(=O)(=O)c1cccnc1C(=O)Nc1cc(S(=O)C(F)(F)F)ccc1O]

$^1$H-NMR (DMSO-d$_6$) δ: 10.29 (1H, s), 8.95 (1H, d), 8.67 (1H, s), 8.44 (1H, d), 7.87 (1H, dd), 7.56 (1H, d), 7.21 (1H, d), 3.70 (2H, q), 1.19 (3H, t).

Production Example 16(2)

To a suspension of the intermediate compound M4-9 (0.50 g) in xylene (5 ml) was added p-toluenesulfonic acid monohydrate (0.45 g). The mixture was stirred at reflux for 8 hours by using a Dean-Stark apparatus. After allowing the reaction mixture to cool, a saturated aqueous sodium bicarbonate solution was added thereto, and then the mixture was extracted with ethyl acetate. The organic layer was washed with a saturated aqueous sodium bicarbonate solution, followed by water and a saturated brine. Then, the mixture was dried on anhydrous magnesium sulfate, and concentrated under reduced pressure. The resultant residue was subjected to silica gel column chromatography to give the present compound 1-9 (0.38 g).

Production Example 17(1)

To a mixture of 4-(trifluoromethylsulfanil)phenol (10.0 g) and sodium tungstate dihydrate (0.86 g) was added 35% hydrogen peroxide solution (4.99 g) at 70° C., and then the mixture was stirred for 30 minutes at 70° C. To the reaction mixture was added 35% hydrogen peroxide solution (5.0 g) at 70° C., and then the mixture was stirred for 1 hour at 80° C. To the reaction mixture was added 35% hydrogen peroxide solution (2.0 g) at 80° C., and then the mixture was stirred for 3 hours at 80° C. To the reaction mixture was added 35% hydrogen peroxide solution (1.0 g) at 80° C., and then the mixture was stirred for 3 hours at 80° C. After allowing the reaction mixture to cool to room temperature, aqueous sodium sulfite solution was added to thereto. The precipitated solid was collected by filtration, and concentrated under reduced pressure to give 4-(trifluoromethylsulfonyl)phenol (10.81 g).

4-(trifluoromethylsulfonyl)phenol:

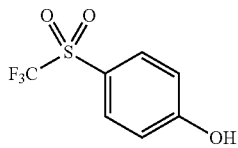

$^1$H-NMR (CDCl$_3$) δ: 7.95-7.91 (2H, m), 7.08-7.04 (2H, m), 6.34 (1H, s).

Production Example 17(2)

To a mixture of 4-(trifluoromethylsulfonyl)phenol (5.0 g) and acetic acid (20 ml) were added 65% nitric acid (1.90 ml) at 50° C., and then the mixture was stirred for 9 hours at 50° C., and stirred for 2 hours at 60° C. To the reaction mixture was added 65% nitric acid (1.26 ml) at 60° C., and then the mixture was stirred for 1 hour at 60° C., and stirred for 8 hours at 70° C. A ice-water was poured to the reaction mixture, and the precipitated solid was collected by filtration. The solid was washed with water and dried under reduced pressure to give 2-nitro-4-(trifluoromethylsulfonyl)phenol (4.98 g).

2-nitro-4-(trifluoromethylsulfonyl)phenol:

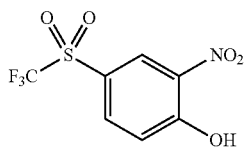 [SMILES: O=[N+]([O-])c1cc(S(=O)(=O)C(F)(F)F)ccc1O]

$^1$H-NMR (CDCl$_3$) δ: 11.22 (1H, s), 8.85 (1H, d), 8.18 (1H, dd), 7.47 (1H, d).

Production Example 17(3)

A mixture of 2-nitro-4-(trifluoromethylsulfonyl)phenol (4.5 g), palladium carbon (Pd 5%) (1.37 g), acetic acid (0.05 ml) and ethanol (45.6 ml) was stirred for 9 hours at 40° C. under hydrogen atmosphere. After allowing the reaction mixture to cool to room temperature, the reaction mixture was filtered through Celite®, and the filtrate was concentrated under reduced pressure. The resultant solid was washed with toluene to give 2-amino-4-(trifluoromethylsulfonyl)phenol (3.78 g).

2-amino-4-(trifluoromethylsulfonyl)phenol:

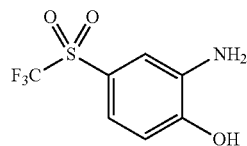

$^1$H-NMR (DMSO-d$_6$) δ: 11.11 (1H, brs), 7.25-7.14 (2H, m), 6.98-6.93 (1H, m), 5.38 (2H, brs).

Production Example 17(4)

Into THF (4.22 g) was dissolved 2-amino-4-(trifluoromethylsulfonyl)phenol (0.60 g), and then 3-ethylsulfonylpicolinic acid chloride (0.59 g) dissolved in THF (3.63 g) was added dropwise thereto at 20 to 25° C. After that, the mixture was stirred for 2 hours at room temperature and then the solvent was removed by evaporation. The precipitated solid was collected by filtration, and dried under reduced pressure to give 3-ethylsulfonyl-N-[2-hydroxy-5-(trifluoromethylsulfonyl)phenyl]picolinamide (hereinafter referred to as "the intermediate compound M4-10") (1.09 g, purity: 86% calculated by $^1$H-NMR).

The Intermediate Compound M4-10:

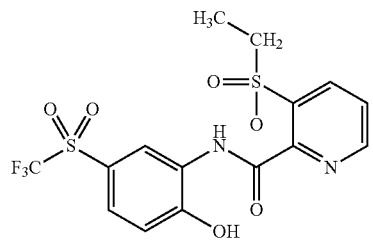

$^1$H-NMR (DMSO-d$_6$) δ: 12.35 (1H, br.s), 10.44 (1H, s), 8.96 (1H, dd), 8.85 (1H, d), 8.44 (1H, dd), 7.87 (1H, dd), 7.81 (1H, dd), 7.31 (1H, d), 3.68 (2H, q), 1.19 (3H, t).

Production Example 17(5)

To the intermediate compound M4-10 (0.60 g) were added monochlorobenzene (7.23 g) and p-toluenesulfonic acid monohydrate (0.52 g), and then the mixture was refluxed by heating for 17 hours. After allowing the reaction mixture to cool to room temperature, water was added thereto. To the mixture was added ethyl acetate (40 mL), and then the organic layer was washed twice with water, followed by a saturated aqueous sodium bicarbonate solution and a saturated brine. The organic layer was dried on anhydrous magnesium sulfate, and concentrated under reduced pressure. The residue was subjected to silica gel column chromatography to give the present compound 1-10 (0.35 g).

The compounds as described in Production Examples and the compounds produced in the same manner as in Production Examples are as listed in Tables as shown below.

The Compound Represented by Formula (1):

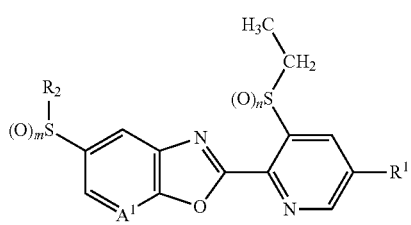

wherein $A^1$, $R^1$, $R^2$, n and m are any of the combinations as listed in Table 3 to Table 5.

TABLE 3

| The present compound | $A^1$ | $R^1$ | $R^2$ | n | m |
|---|---|---|---|---|---|
| 1-1 | N | H | $CF_3$ | 0 | 0 |
| 1-2 | N | H | $CF_3$ | 1 | 0 |
| 1-3 | N | H | $CF_3$ | 2 | 0 |
| 1-4 | N | H | $CF_3$ | 2 | 1 |
| 1-5 | N | H | $CF_3$ | 2 | 2 |
| 1-6 | CH | H | $CF_3$ | 0 | 0 |
| 1-7 | CH | H | $CF_3$ | 1 | 0 |
| 1-8 | CH | H | $CF_3$ | 2 | 0 |
| 1-9 | CH | H | $CF_3$ | 2 | 1 |
| 1-10 | CH | H | $CF_3$ | 2 | 2 |
| 1-11 | N | $CF_3$ | $CF_3$ | 0 | 0 |
| 1-12 | N | $CF_3$ | $CF_3$ | 1 | 0 |
| 1-13 | N | $CF_3$ | $CF_3$ | 2 | 0 |
| 1-14 | N | $CF_3$ | $CF_3$ | 2 | 1 |
| 1-15 | N | $CF_3$ | $CF_3$ | 2 | 2 |
| 1-16 | CH | $CF_3$ | $CF_3$ | 0 | 0 |
| 1-17 | CH | $CF_3$ | $CF_3$ | 1 | 0 |
| 1-18 | CH | $CF_3$ | $CF_3$ | 2 | 0 |
| 1-19 | CH | $CF_3$ | $CF_3$ | 2 | 1 |
| 1-20 | CH | $CF_3$ | $CF_3$ | 2 | 2 |
| 1-21 | N | Cl | $CF_3$ | 0 | 0 |
| 1-22 | N | Cl | $CF_3$ | 1 | 0 |
| 1-23 | N | Cl | $CF_3$ | 2 | 0 |
| 1-24 | N | Cl | $CF_3$ | 2 | 1 |
| 1-25 | N | Cl | $CF_3$ | 2 | 2 |

TABLE 4

| The present compound | $A^1$ | $R^1$ | $R^2$ | n | m |
|---|---|---|---|---|---|
| 1-26 | CH | Cl | $CF_3$ | 0 | 0 |
| 1-27 | CH | Cl | $CF_3$ | 1 | 0 |
| 1-28 | CH | Cl | $CF_3$ | 2 | 0 |
| 1-29 | CH | Cl | $CF_3$ | 2 | 1 |
| 1-30 | CH | Cl | $CF_3$ | 2 | 2 |
| 1-31 | N | Br | $CF_3$ | 0 | 0 |
| 1-32 | N | Br | $CF_3$ | 1 | 0 |
| 1-33 | N | Br | $CF_3$ | 2 | 0 |
| 1-34 | N | Br | $CF_3$ | 2 | 1 |
| 1-35 | N | Br | $CF_3$ | 2 | 2 |
| 1-36 | CH | Br | $CF_3$ | 0 | 0 |
| 1-37 | CH | Br | $CF_3$ | 1 | 0 |
| 1-38 | CH | Br | $CF_3$ | 2 | 0 |
| 1-39 | CH | Br | $CF_3$ | 2 | 1 |
| 1-40 | CH | Br | $CF_3$ | 2 | 2 |
| 1-41 | N | H | $CF_2CF_3$ | 0 | 0 |
| 1-42 | N | H | $CF_2CF_3$ | 1 | 0 |
| 1-43 | N | H | $CF_2CF_3$ | 2 | 0 |
| 1-44 | N | H | $CF_2CF_3$ | 2 | 1 |
| 1-45 | N | H | $CF_2CF_3$ | 2 | 2 |

TABLE 4-continued

| The present compound | $A^1$ | $R^1$ | $R^2$ | n | m |
|---|---|---|---|---|---|
| 1-46 | CH | H | $CF_2CF_3$ | 0 | 0 |
| 1-47 | CH | H | $CF_2CF_3$ | 1 | 0 |
| 1-48 | CH | H | $CF_2CF_3$ | 2 | 0 |
| 1-49 | CH | H | $CF_2CF_3$ | 2 | 1 |
| 1-50 | CH | H | $CF_2CF_3$ | 2 | 2 |

TABLE 5

| The present compound | $A^1$ | $R^1$ | $R^2$ | n | m |
|---|---|---|---|---|---|
| 1-51 | N | $CF_3$ | $CF_2CF_3$ | 0 | 0 |
| 1-52 | N | $CF_3$ | $CF_2CF_3$ | 1 | 0 |
| 1-53 | N | $CF_3$ | $CF_2CF_3$ | 2 | 0 |
| 1-54 | N | $CF_3$ | $CF_2CF_3$ | 2 | 1 |
| 1-55 | N | $CF_3$ | $CF_2CF_3$ | 2 | 2 |
| 1-56 | CH | $CF_3$ | $CF_2CF_3$ | 0 | 0 |
| 1-57 | CH | $CF_3$ | $CF_2CF_3$ | 1 | 0 |
| 1-58 | CH | $CF_3$ | $CF_2CF_3$ | 2 | 0 |
| 1-59 | CH | $CF_3$ | $CF_2CF_3$ | 2 | 1 |
| 1-60 | CH | $CF_3$ | $CF_2CF_3$ | 2 | 2 |
| 1-61 | N | H | $CF_3$ | 0 | 1 |
| 1-62 | N | H | $CF_3$ | 0 | 2 |
| 1-63 | CH | H | $CF_3$ | 0 | 1 |
| 1-64 | CH | H | $CF_3$ | 0 | 2 |
| 1-65 | N | $CF_3$ | $CF_3$ | 0 | 1 |
| 1-66 | N | $CF_3$ | $CF_3$ | 0 | 2 |
| 1-67 | CH | $CF_3$ | $CF_3$ | 0 | 1 |
| 1-68 | CH | $CF_3$ | $CF_3$ | 0 | 2 |
| 1-93 | CH | Cl | $CF_3$ | 1 | 1 |
| 1-94 | CH | Cl | $CF_3$ | 0 | 1 |
| 1-95 | CH | F | $CF_3$ | 0 | 0 |
| 1-96 | CH | F | $CF_3$ | 2 | 0 |
| 1-97 | CH | F | $CF_3$ | 2 | 2 |
| 1-98 | CH | H | $CF_3$ | 1 | 2 |

The Compound Represented by Formula (1A):

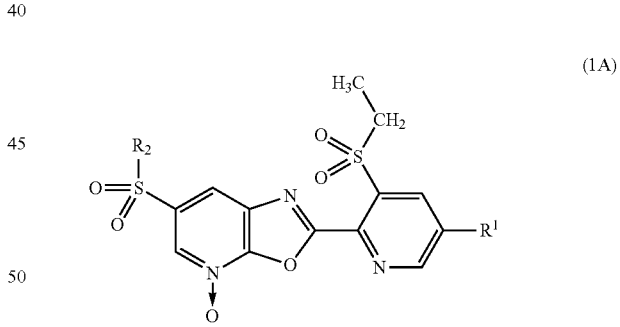

wherein $R^1$ and $R^2$ are any of the combinations as listed in Table 6.

TABLE 6

| The present compound | $R^1$ | $R^2$ |
|---|---|---|
| 1-69 | H | $CF_3$ |
| 1-70 | $CF_3$ | $CF_3$ |
| 1-71 | Cl | $CF_3$ |
| 1-72 | Br | $CF_3$ |
| 1-73 | H | $CF_2CF_3$ |
| 1-74 | $CF_3$ | $CF_2CF_3$ |

The Compound Represented by Formula (1B):

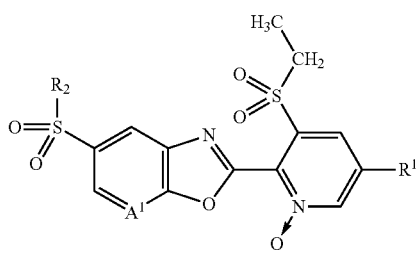

wherein $A^1$, $R^1$ and $R^2$ are any of the combinations as listed in Table 7.

TABLE 7

| The present compound | $A^1$ | $R^1$ | $R^2$ |
|---|---|---|---|
| 1-75 | N | H | $CF_3$ |
| 1-76 | CH | H | $CF_3$ |
| 1-77 | N | $CF_3$ | $CF_3$ |
| 1-78 | CH | $CF_3$ | $CF_3$ |
| 1-79 | N | Cl | $CF_3$ |
| 1-80 | CH | Cl | $CF_3$ |
| 1-81 | N | Br | $CF_3$ |
| 1-82 | CH | Br | $CF_3$ |
| 1-83 | N | H | $CF_2CF_3$ |
| 1-84 | CH | H | $CF_2CF_3$ |
| 1-85 | N | $CF_3$ | $CF_2CF_3$ |
| 1-86 | CH | $CF_3$ | $CF_2CF_3$ |

The Compound Represented by Formula (1C):

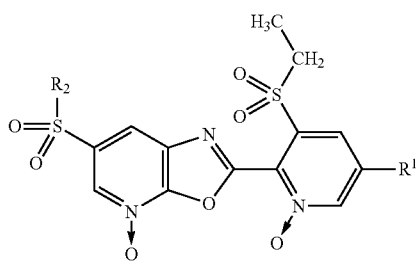

wherein $R^1$ and $R^2$ are any of the combinations as listed in Table 8.

TABLE 8

| The present compound | $R^1$ | $R^2$ |
|---|---|---|
| 1-87 | H | $CF_3$ |
| 1-88 | $CF_3$ | $CF_3$ |
| 1-89 | Cl | $CF_3$ |
| 1-90 | Br | $CF_3$ |
| 1-91 | H | $CF_2CF_3$ |
| 1-92 | $CF_3$ | $CF_2CF_3$ |

Hereinafter, $^1$H-NMR data of the present compounds listed in Table 3 to Table 8 are shown.

The Present Compound 1-26:
$^1$H-NMR (CDCl$_3$) δ: 8.50 (1H, dd), 8.26 (1H, s), 7.74-7.70 (3H, m), 3.07 (2H, q), 1.50 (3H, t).

The Present Compound 1-28:
$^1$H-NMR (CDCl$_3$) δ: 8.96 (1H, d), 8.59 (1H, d), 8.19 (1H, d), 7.79 (1H, dd), 7.74 (1H, d), 4.08 (2H, q), 1.46 (3H, t).

The Present Compound 1-29:
$^1$H-NMR (CDCl$_3$) δ: 8.97 (1H, dd), 8.60 (1H, dd), 8.36 (1H, s), 7.94 (1H, d), 7.89 (1H, d), 4.07 (2H, q), 1.47 (3H, t).

The Present Compound 1-30:
$^1$H-NMR (CDCl$_3$) δ: 8.99 (1H, d), 8.60 (1H, d), 8.59 (1H, d), 8.18 (1H, dd), 7.98 (1H, dd), 4.04 (2H, q), 1.47 (3H, t).

The Present Compound 1-46:
$^1$H-NMR (CDCl$_3$) δ: 8.59 (1H, dd), 8.26 (1H, d), 7.79 (1H, dd), 7.74 (1H, d), 7.70 (1H, dd), 7.43 (1H, dd), 3.07 (2H, q), 1.48 (3H, t).

The Present Compound 1-48:
$^1$H-NMR (CDCl$_3$) δ: 9.03 (1H, dd), 8.61 (1H, dd), 8.18 (1H, s), 7.79-7.71 (3H, m), 4.04 (2H, q), 1.43 (3H, t).

The Present Compound 1-49:
$^1$H-NMR (CDCl$_3$) δ: 9.05 (1H, dd), 8.62 (1H, dd), 8.36 (1H, d), 7.94 (1H, dd), 7.88 (1H, d), 7.78 (1H, dd), 4.02 (2H, q), 1.44 (3H, t).

The Present Compound 1-50:
$^1$H-NMR (CDCl$_3$) δ: 9.06 (1H, dd), 8.62 (1H, dd), 8.58 (1H, d), 8.17 (1H, dd), 7.97 (1H, d), 7.80 (1H, dd), 3.99 (2H, q), 1.45 (3H, t).

The Present Compound 1-64:
$^1$H-NMR (CDCl$_3$) δ: 8.66 (1H, d), 8.61 (1H, dd), 8.12 (1H, dd), 7.98-7.92 (1H, m), 7.82 (1H, dd), 7.47 (1H, dd), 3.09 (2H, q), 1.49 (3H, t).

The Present Compound 1-94:
$^1$H-NMR (CDCl$_3$) δ: 8.52 (1H, d), 8.39 (1H, d), 7.93 (1H, d), 7.88 (1H, dd), 7.74 (1H, d), 3.08 (2H, q), 1.51 (3H, t).

The Present Compound 1-95:
$^1$H-NMR (CDCl$_3$) δ: 8.42 (1H, d), 8.26 (1H, s), 7.73-7.71 (2H, m), 7.48 (1H, dd), 3.05 (2H, q), 1.50 (3H, t).

The Present Compound 1-96:
$^1$H-NMR (CDCl$_3$) δ: 8.88 (1H, d), 8.34 (1H, dd), 8.19 (1H, d), 7.78 (1H, dd), 7.74 (1H, d), 4.08 (2H, q), 1.45 (3H, t).

The Present Compound 1-97:
$^1$H-NMR (CDCl$_3$) δ: 8.90 (1H, d), 8.59 (1H, d), 8.35 (1H, dd), 8.18 (1H, dd), 7.97 (1H, d), 4.04 (2H, q), 1.47 (3H, t).

The Present Compound 1-98:
$^1$H-NMR (CDCl$_3$) δ: 8.96 (1H, dd), 8.70 (1H, dd), 8.61 (1H, d), 8.18 (1H, dd), 8.10-7.96 (1H, m), 7.82 (1H, dd), 3.62-3.45 (1H, m), 3.17-2.99 (1H, m), 1.43 (3H, t).

The Compound Represented by Formula (M4):

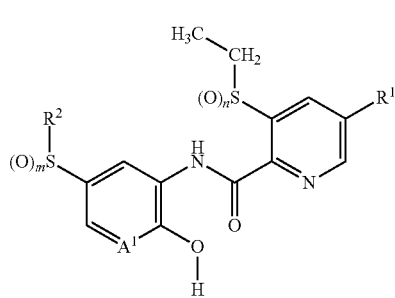

wherein $A^1$, $R^1$, $R^2$, n and m are any of the combinations as listed in Table 9 to Table 11.

TABLE 9

| Intermediate compound | $A^1$ | $R^1$ | $R^2$ | n | m |
|---|---|---|---|---|---|
| M4-1 | N | H | $CF_3$ | 0 | 0 |
| M4-2 | N | H | $CF_3$ | 1 | 0 |
| M4-3 | N | H | $CF_3$ | 2 | 0 |
| M4-4 | N | H | $CF_3$ | 2 | 1 |
| M4-5 | N | H | $CF_3$ | 2 | 2 |
| M4-6 | CH | H | $CF_3$ | 0 | 0 |
| M4-7 | CH | H | $CF_3$ | 1 | 0 |
| M4-8 | CH | H | $CF_3$ | 2 | 0 |
| M4-9 | CH | H | $CF_3$ | 2 | 1 |
| M4-10 | CH | H | $CF_3$ | 2 | 2 |
| M4-11 | N | $CF_3$ | $CF_3$ | 0 | 0 |
| M4-12 | N | $CF_3$ | $CF_3$ | 1 | 0 |
| M4-13 | N | $CF_3$ | $CF_3$ | 2 | 0 |
| M4-14 | N | $CF_3$ | $CF_3$ | 2 | 1 |
| M4-15 | N | $CF_3$ | $CF_3$ | 2 | 2 |
| M4-16 | CH | $CF_3$ | $CF_3$ | 0 | 0 |
| M4-17 | CH | $CF_3$ | $CF_3$ | 1 | 0 |
| M4-18 | CH | $CF_3$ | $CF_3$ | 2 | 0 |
| M4-19 | CH | $CF_3$ | $CF_3$ | 2 | 1 |
| M4-20 | CH | $CF_3$ | $CF_3$ | 2 | 2 |
| M4-21 | N | Cl | $CF_3$ | 0 | 0 |
| M4-22 | N | Cl | $CF_3$ | 1 | 0 |
| M4-23 | N | Cl | $CF_3$ | 2 | 0 |
| M4-24 | N | Cl | $CF_3$ | 2 | 1 |
| M4-25 | N | Cl | $CF_3$ | 2 | 2 |

TABLE 10

| Intermediate compound | $A^1$ | $R^1$ | $R^2$ | n | m |
|---|---|---|---|---|---|
| M4-26 | CH | Cl | $CF_3$ | 0 | 0 |
| M4-27 | CH | Cl | $CF_3$ | 1 | 0 |
| M4-28 | CH | Cl | $CF_3$ | 2 | 0 |
| M4-29 | CH | Cl | $CF_3$ | 2 | 1 |
| M4-30 | CH | Cl | $CF_3$ | 2 | 2 |
| M4-31 | N | Br | $CF_3$ | 0 | 0 |
| M4-32 | N | Br | $CF_3$ | 1 | 0 |
| M4-33 | N | Br | $CF_3$ | 2 | 0 |
| M4-34 | N | Br | $CF_3$ | 2 | 1 |
| M4-35 | N | Br | $CF_3$ | 2 | 2 |
| M4-36 | CH | Br | $CF_3$ | 0 | 0 |
| M4-37 | CH | Br | $CF_3$ | 1 | 0 |
| M4-38 | CH | Br | $CF_3$ | 2 | 0 |
| M4-39 | CH | Br | $CF_3$ | 2 | 1 |
| M4-40 | CH | Br | $CF_3$ | 2 | 2 |
| M4-41 | N | H | $CF_2CF_3$ | 0 | 0 |
| M4-42 | N | H | $CF_2CF_3$ | 1 | 0 |
| M4-43 | N | H | $CF_2CF_3$ | 2 | 0 |
| M4-44 | N | H | $CF_2CF_3$ | 2 | 1 |
| M4-45 | N | H | $CF_2CF_3$ | 2 | 2 |
| M4-46 | CH | H | $CF_2CF_3$ | 0 | 0 |
| M4-47 | CH | H | $CF_2CF_3$ | 1 | 0 |
| M4-48 | CH | H | $CF_2CF_3$ | 2 | 0 |
| M4-49 | CH | H | $CF_2CF_3$ | 2 | 1 |
| M4-50 | CH | H | $CF_2CF_3$ | 2 | 2 |

TABLE 11

| Intermediate compound | $A^1$ | $R^1$ | $R^2$ | n | m |
|---|---|---|---|---|---|
| M4-51 | N | $CF_3$ | $CF_2CF_3$ | 0 | 0 |
| M4-52 | N | $CF_3$ | $CF_2CF_3$ | 1 | 0 |
| M4-53 | N | $CF_3$ | $CF_2CF_3$ | 2 | 0 |
| M4-54 | N | $CF_3$ | $CF_2CF_3$ | 2 | 1 |
| M4-55 | N | $CF_3$ | $CF_2CF_3$ | 2 | 2 |
| M4-56 | CH | $CF_3$ | $CF_2CF_3$ | 0 | 0 |
| M4-57 | CH | $CF_3$ | $CF_2CF_3$ | 1 | 0 |
| M4-58 | CH | $CF_3$ | $CF_2CF_3$ | 2 | 0 |
| M4-59 | CH | $CF_3$ | $CF_2CF_3$ | 2 | 1 |
| M4-60 | CH | $CF_3$ | $CF_2CF_3$ | 2 | 2 |

TABLE 11-continued

| Intermediate compound | $A^1$ | $R^1$ | $R^2$ | n | m |
|---|---|---|---|---|---|
| M4-61 | N | H | $CF_3$ | 0 | 1 |
| M4-62 | N | H | $CF_3$ | 0 | 2 |
| M4-63 | CH | H | $CF_3$ | 0 | 1 |
| M4-64 | CH | H | $CF_3$ | 0 | 2 |
| M4-65 | N | $CF_3$ | $CF_3$ | 0 | 1 |
| M4-66 | N | $CF_3$ | $CF_3$ | 0 | 2 |
| M4-67 | CH | $CF_3$ | $CF_3$ | 0 | 1 |
| M4-68 | CH | $CF_3$ | $CF_3$ | 0 | 2 |

The Compound Represented by Formula (M6):

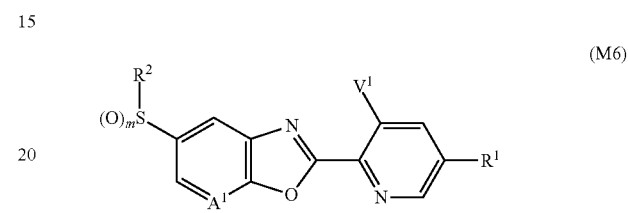

wherein $A^1$, $R^1$, $R^2$, m and $V^1$ are any of the combinations as listed in Table 12 to Table 14.

TABLE 12

| Intermediate compound | $A^1$ | $R^1$ | $R^2$ | m | $V^1$ |
|---|---|---|---|---|---|
| M6-1 | N | H | $CF_3$ | 0 | F |
| M6-2 | N | H | $CF_3$ | 1 | F |
| M6-3 | N | H | $CF_3$ | 2 | F |
| M6-4 | CH | H | $CF_3$ | 0 | F |
| M6-5 | CH | H | $CF_3$ | 1 | F |
| M6-6 | CH | H | $CF_3$ | 2 | F |
| M6-7 | N | $CF_3$ | $CF_3$ | 0 | F |
| M6-8 | N | $CF_3$ | $CF_3$ | 1 | F |
| M6-9 | N | $CF_3$ | $CF_3$ | 2 | F |
| M6-10 | CH | $CF_3$ | $CF_3$ | 0 | F |
| M6-11 | CH | $CF_3$ | $CF_3$ | 1 | F |
| M6-12 | CH | $CF_3$ | $CF_3$ | 2 | F |
| M6-13 | N | Cl | $CF_3$ | 0 | F |
| M6-14 | N | Cl | $CF_3$ | 1 | F |
| M6-15 | N | Cl | $CF_3$ | 2 | F |
| M6-16 | CH | Cl | $CF_3$ | 0 | F |
| M6-17 | CH | Cl | $CF_3$ | 1 | F |
| M6-18 | CH | Cl | $CF_3$ | 2 | F |
| M6-19 | N | Br | $CF_3$ | 0 | F |
| M6-20 | N | Br | $CF_3$ | 1 | F |
| M6-21 | N | Br | $CF_3$ | 2 | F |
| M6-22 | CH | Br | $CF_3$ | 0 | F |
| M6-23 | CH | Br | $CF_3$ | 1 | F |
| M6-24 | CH | Br | $CF_3$ | 2 | F |
| M6-25 | N | H | $CF_2CF_3$ | 0 | F |

TABLE 13

| Intermediate compound | $A^1$ | $R^1$ | $R^2$ | m | $V^1$ |
|---|---|---|---|---|---|
| M6-26 | N | H | $CF_2CF_3$ | 1 | F |
| M6-27 | N | H | $CF_2CF_3$ | 2 | F |
| M6-28 | CH | H | $CF_2CF_3$ | 0 | F |
| M6-29 | CH | H | $CF_2CF_3$ | 1 | F |
| M6-30 | CH | H | $CF_2CF_3$ | 2 | F |
| M6-31 | N | H | $CF_3$ | 0 | Cl |
| M6-32 | N | H | $CF_3$ | 1 | Cl |
| M6-33 | N | H | $CF_3$ | 2 | Cl |
| M6-34 | CH | H | $CF_3$ | 0 | Cl |
| M6-35 | CH | H | $CF_3$ | 1 | Cl |
| M6-36 | CH | H | $CF_3$ | 2 | Cl |

TABLE 13-continued

| Intermediate compound | $A^1$ | $R^1$ | $R^2$ | m | $V^1$ |
|---|---|---|---|---|---|
| M6-37 | N | $CF_3$ | $CF_3$ | 0 | Cl |
| M6-38 | N | $CF_3$ | $CF_3$ | 1 | Cl |
| M6-39 | N | $CF_3$ | $CF_3$ | 2 | Cl |
| M6-40 | CH | $CF_3$ | $CF_3$ | 0 | Cl |
| M6-41 | CH | $CF_3$ | $CF_3$ | 1 | Cl |
| M6-42 | CH | $CF_3$ | $CF_3$ | 2 | Cl |
| M6-43 | N | Cl | $CF_3$ | 0 | Cl |
| M6-44 | N | Cl | $CF_3$ | 1 | Cl |
| M6-45 | N | Cl | $CF_3$ | 2 | Cl |
| M6-46 | CH | Cl | $CF_3$ | 0 | Cl |
| M6-47 | CH | Cl | $CF_3$ | 1 | Cl |
| M6-48 | CH | Cl | $CF_3$ | 2 | Cl |
| M6-49 | N | Br | $CF_3$ | 0 | Cl |
| M6-50 | N | Br | $CF_3$ | 1 | Cl |

TABLE 14

| Intermediate compound | $A^1$ | $R^1$ | $R^2$ | m | $V^1$ |
|---|---|---|---|---|---|
| M6-51 | N | Br | $CF_3$ | 2 | Cl |
| M6-52 | CH | Br | $CF_3$ | 0 | Cl |
| M6-53 | CH | Br | $CF_3$ | 1 | Cl |
| M6-54 | CH | Br | $CF_3$ | 2 | Cl |
| M6-55 | N | H | $CF_2CF_3$ | 0 | Cl |
| M6-56 | N | H | $CF_2CF_3$ | 1 | Cl |
| M6-57 | N | H | $CF_2CF_3$ | 2 | Cl |
| M6-58 | CH | H | $CF_2CF_3$ | 0 | Cl |
| M6-59 | CH | H | $CF_2CF_3$ | 1 | Cl |
| M6-60 | CH | H | $CF_2CF_3$ | 2 | Cl |
| M6-61 | CH | F | $CF_3$ | 0 | F |
| M6-62 | CH | F | $CF_3$ | 2 | F |

The Compound Represented by Formula (M10):

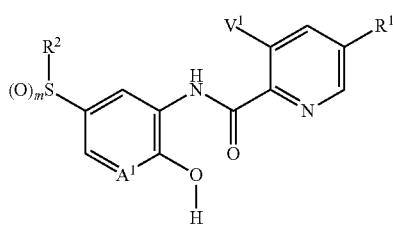

(M10)

wherein $A^1$, $R^1$, $R^2$, m and $V^1$ are any of the combinations as listed in Table 15 to Table 17.

TABLE 15

| Intermediate compound | $A^1$ | $R^1$ | $R^2$ | m | $V^1$ |
|---|---|---|---|---|---|
| M10-1 | N | H | $CF_3$ | 0 | F |
| M10-2 | N | H | $CF_3$ | 1 | F |
| M10-3 | N | H | $CF_3$ | 2 | F |
| M10-4 | CH | H | $CF_3$ | 0 | F |
| M10-5 | CH | H | $CF_3$ | 1 | F |
| M10-6 | CH | H | $CF_3$ | 2 | F |
| M10-7 | N | $CF_3$ | $CF_3$ | 0 | F |
| M10-8 | N | $CF_3$ | $CF_3$ | 1 | F |
| M10-9 | N | $CF_3$ | $CF_3$ | 2 | F |
| M10-10 | CH | $CF_3$ | $CF_3$ | 0 | F |
| M10-11 | CH | $CF_3$ | $CF_3$ | 1 | F |
| M10-12 | CH | $CF_3$ | $CF_3$ | 2 | F |
| M10-13 | N | Cl | $CF_3$ | 0 | F |
| M10-14 | N | Cl | $CF_3$ | 1 | F |
| M10-15 | N | Cl | $CF_3$ | 2 | F |

TABLE 15-continued

| Intermediate compound | $A^1$ | $R^1$ | $R^2$ | m | $V^1$ |
|---|---|---|---|---|---|
| M10-16 | CH | Cl | $CF_3$ | 0 | F |
| M10-17 | CH | Cl | $CF_3$ | 1 | F |
| M10-18 | CH | Cl | $CF_3$ | 2 | F |
| M10-19 | N | Br | $CF_3$ | 0 | F |
| M10-20 | N | Br | $CF_3$ | 1 | F |
| M10-21 | N | Br | $CF_3$ | 2 | F |
| M10-22 | CH | Br | $CF_3$ | 0 | F |
| M10-23 | CH | Br | $CF_3$ | 1 | F |
| M10-24 | CH | Br | $CF_3$ | 2 | F |
| M10-25 | N | H | $CF_2CF_3$ | 0 | F |

TABLE 16

| Intermediate compound | $A^1$ | $R^1$ | $R^2$ | m | $V^1$ |
|---|---|---|---|---|---|
| M10-26 | N | H | $CF_2CF_3$ | 1 | F |
| M10-27 | N | H | $CF_2CF_3$ | 2 | F |
| M10-28 | CH | H | $CF_2CF_3$ | 0 | F |
| M10-29 | CH | H | $CF_2CF_3$ | 1 | F |
| M10-30 | CH | H | $CF_2CF_3$ | 2 | F |
| M10-31 | N | H | $CF_3$ | 0 | Cl |
| M10-32 | N | H | $CF_3$ | 1 | Cl |
| M10-33 | N | H | $CF_3$ | 2 | Cl |
| M10-34 | CH | H | $CF_3$ | 0 | Cl |
| M10-35 | CH | H | $CF_3$ | 1 | Cl |
| M10-36 | CH | H | $CF_3$ | 2 | Cl |
| M10-37 | N | $CF_3$ | $CF_3$ | 0 | Cl |
| M10-38 | N | $CF_3$ | $CF_3$ | 1 | Cl |
| M10-39 | N | $CF_3$ | $CF_3$ | 2 | Cl |
| M10-40 | CH | $CF_3$ | $CF_3$ | 0 | Cl |
| M10-41 | CH | $CF_3$ | $CF_3$ | 1 | Cl |
| M10-42 | CH | $CF_3$ | $CF_3$ | 2 | Cl |
| M10-43 | N | Cl | $CF_3$ | 0 | Cl |
| M10-44 | N | Cl | $CF_3$ | 1 | Cl |
| M10-45 | N | Cl | $CF_3$ | 2 | Cl |
| M10-46 | CH | Cl | $CF_3$ | 0 | Cl |
| M10-47 | CH | Cl | $CF_3$ | 1 | Cl |
| M10-48 | CH | Cl | $CF_3$ | 2 | Cl |
| M10-49 | N | Br | $CF_3$ | 0 | Cl |
| M10-50 | N | Br | $CF_3$ | 1 | Cl |

TABLE 17

| Intermediate compound | $A^1$ | $R^1$ | $R^2$ | m | $V^1$ |
|---|---|---|---|---|---|
| M10-51 | N | Br | $CF_3$ | 2 | Cl |
| M10-52 | CH | Br | $CF_3$ | 0 | Cl |
| M10-53 | CH | Br | $CF_3$ | 1 | Cl |
| M10-54 | CH | Br | $CF_3$ | 2 | Cl |
| M10-55 | N | H | $CF_2CF_3$ | 0 | Cl |
| M10-56 | N | H | $CF_2CF_3$ | 1 | Cl |
| M10-57 | N | H | $CF_2CF_3$ | 2 | Cl |
| M10-58 | CH | H | $CF_2CF_3$ | 0 | Cl |
| M10-59 | CH | H | $CF_2CF_3$ | 1 | Cl |
| M10-60 | CH | H | $CF_2CF_3$ | 2 | Cl |
| M10-61 | CH | F | $CF_3$ | 0 | F |
| M10-62 | CH | F | $CF_3$ | 2 | F |

The Compound Represented by Formula (M16):

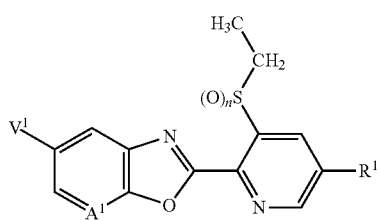

wherein $A^1$, $R^1$, n and $V^1$ are any of the combinations as listed in Table 18 to Table 19.

TABLE 18

| Intermediate compound | $A^1$ | $R^1$ | n | $V^1$ |
|---|---|---|---|---|
| M16-1 | N | H | 0 | Br |
| M16-2 | N | H | 1 | Br |
| M16-3 | N | H | 2 | Br |
| M16-4 | CH | H | 0 | Br |
| M16-5 | CH | H | 1 | Br |
| M16-6 | CH | H | 2 | Br |
| M16-7 | N | $CF_3$ | 0 | Br |
| M16-8 | N | $CF_3$ | 1 | Br |
| M16-9 | N | $CF_3$ | 2 | Br |
| M16-10 | CH | $CF_3$ | 0 | Br |
| M16-11 | CH | $CF_3$ | 1 | Br |
| M16-12 | CH | $CF_3$ | 2 | Br |
| M16-13 | N | Cl | 0 | Br |
| M16-14 | N | Cl | 1 | Br |
| M16-15 | N | Cl | 2 | Br |
| M16-16 | CH | Cl | 0 | Br |
| M16-17 | CH | Cl | 1 | Br |
| M16-18 | CH | Cl | 2 | Br |
| M16-19 | N | Br | 0 | Br |
| M16-20 | N | Br | 1 | Br |
| M16-21 | N | Br | 2 | Br |
| M16-22 | CH | Br | 0 | Br |
| M16-23 | CH | Br | 1 | Br |
| M16-24 | CH | Br | 2 | Br |
| M16-25 | N | H | 0 | I |

TABLE 19

| Intermediate compound | $A^1$ | $R^1$ | n | $V^1$ |
|---|---|---|---|---|
| M16-26 | N | H | 1 | I |
| M16-27 | N | H | 2 | I |
| M16-28 | CH | H | 0 | I |
| M16-29 | CH | H | 1 | I |
| M16-30 | CH | H | 2 | I |
| M16-31 | N | $CF_3$ | 0 | I |
| M16-32 | N | $CF_3$ | 1 | I |
| M16-33 | N | $CF_3$ | 2 | I |
| M16-34 | CH | $CF_3$ | 0 | I |
| M16-35 | CH | $CF_3$ | 1 | I |
| M16-36 | CH | $CF_3$ | 2 | I |
| M16-37 | N | Cl | 0 | I |
| M16-38 | N | Cl | 1 | I |
| M16-39 | N | Cl | 2 | I |
| M16-40 | CH | Cl | 0 | I |
| M16-41 | CH | Cl | 1 | I |
| M16-42 | CH | Cl | 2 | I |
| M16-43 | N | Br | 0 | I |
| M16-44 | N | Br | 1 | I |
| M16-45 | N | Br | 2 | I |
| M16-46 | CH | Br | 0 | I |
| M16-47 | CH | Br | 1 | I |
| M16-48 | CH | Br | 2 | I |

Hereinafter, $^1$H-NMR data of the intermediate compounds listed in Table 9 to Table 19] are shown.

M4-8
$^1$H-NMR (DMSO-$d_6$) δ: 11.05 (1H, s), 10.15 (1H, s), 8.95 (1H, d), 8.47 (1H, s), 8.43 (1H, d), 7.87 (1H, dd), 7.38 (1H, d), 7.06 (1H, d), 3.71 (2H, q), 1.19 (3H, t).

M4-46
$^1$H-NMR (CDCl$_3$) δ: 10.42 (1H, s), 8.37 (1H, dd), 7.75 (1H, dd), 7.53 (1H, d), 7.46 (1H, dd), 7.40 (1H, dd), 7.08 (1H, d), 2.97 (2H, q), 1.45 (3H, t).

M4-64
$^1$H-NMR (DMSO-$d_6$) δ: 12.54 (1H, s), 10.69 (1H, s), 9.07 (1H, s), 8.48 (1H, d), 7.98 (1H, d), 7.77 (1H, d), 7.65 (1H, dd), 7.31 (1H, d), 2.99 (2H, q), 1.31 (3H, t).

M6-34
$^1$H-NMR (CDCl$_3$) δ: 8.77 (1H, dd), 8.26 (1H, s), 7.98 (1H, dd), 7.77-7.72 (2H, m), 7.47 (1H, dd).

M6-35
$^1$H-NMR (DMSO-D$_6$) δ: 8.82 (1H, dd), 8.52 (1H, s), 8.30-8.24 (2H, m), 8.07 (1H, d), 7.75 (1H, dd).

M6-36
$^1$H-NMR (CDCl$_3$) δ: 8.79 (1H, dd), 8.65 (1H, d), 8.16 (1H, dd), 8.01 (1H, dd), 7.97 (1H, d), 7.53 (1H, dd).

M6-46
$^1$H-NMR (CDCl$_3$) δ: 8.71 (1H, dd), 8.25 (1H, s), 8.00 (1H, dd), 7.79-7.72 (2H, m).

M6-61
$^1$H-NMR (CDCl$_3$) δ: 8.61 (1H, d), 8.23 (1H, s), 7.79-7.72 (2H, m), 7.54-7.47 (1H, m).

M10-34
$^1$H-NMR (CDCl$_3$) δ: 10.29 (1H, s), 9.45 (1H, brs), 8.58 (1H, dd), 7.94 (1H, dd), 7.54 (1H, d), 7.51 (1H, dd), 7.44 (1H, dd), 7.10 (1H, d).

M10-35
$^1$H-NMR (DMSO-D$_6$) δ: 11.59 (1H, s), 10.47 (1H, s), 8.83 (1H, d), 8.69 (1H, dd), 8.15 (1H, dd), 7.69 (1H, dd), 7.55 (1H, dd), 7.22 (1H, d).

M10-36
$^1$H-NMR (DMSO-$d_6$) δ: 12.48 (1H, br.s), 10.56 (1H, s), 9.01 (1H, d), 8.70 (1H, dd), 8.16 (1H, dd), 7.79 (1H, dd), 7.70 (1H, dd), 7.31 (1H, d).

M10-46
$^1$H-NMR (DMSO-D$_6$) δ: 11.64 (1H, brs), 10.36 (1H, s), 8.80-8.77 (2H, m), 8.46 (1H, d), 7.54 (1H, d), 7.21 (1H, d).

M10-61
$^1$H-NMR (CDCl$_3$) δ: 9.91 (1H, brs), 9.42 (1H, s), 8.42 (1H, d), 7.54 (1H, d), 7.48-7.43 (2H, m), 7.10 (1H, d).

M16-25
$^1$H-NMR (CDCl$_3$) δ: 8.63 (1H, d), 8.61 (1H, dd), 8.51 (1H, d), 7.78 (1H, dd), 7.43 (1H, dd), 3.05 (2H, q), 1.45 (3H, t).

M16-28
$^1$H-NMR (CDCl$_3$) δ: 8.57 (1H, dd), 8.27 (1H, d), 7.77 (1H, dd), 7.71 (1H, dd), 7.46 (1H, d), 7.40 (1H, dd), 3.05 (2H, q), 1.46 (3H, t).

M16-29
$^1$H-NMR (CDCl$_3$) δ: 8.91 (1H, d), 8.64 (1H, d), 8.26-8.20 (1H, m), 7.80-7.70 (2H, m), 7.50 (1H, d), 3.53-3.42 (1H, m), 3.06-2.96 (1H, m), 1.41 (3H, t).

M16-30
$^1$H-NMR (CDCl$_3$) δ: 9.02 (1H, dd), 8.59 (1H, dd), 8.20 (1H, d), 7.76 (1H, dd), 7.72 (1H, dd), 7.47 (1H, d), 4.02 (2H, q), 1.42 (3H, t).

M16-31
$^1$H-NMR (CDCl$_3$) δ: 8.80 (1H, s), 8.67 (1H, d), 8.56 (1H, d), 7.93 (1H, s), 3.10 (2H, q), 1.49 (3H, t).

Next, Formulation Examples will be described. Herein, the term "part(s)" means "part(s) by weight".

Formulation Example 1

Any one of the present compounds 1-1 to 1-98 (10 parts) is dissolved in a mixture of xylene (35 parts) and N,N-dimethylformamide (35 parts), and to the mixture is added polyoxyethylene styryl phenyl ether (14 parts) and calcium dodecylbenzenesulfonate (6 parts), and stirred to give an emulsifiable concentrate of each compound.

Formulation Example 2

Sodium lauryl sulfate (4 parts), calcium lignin sulfonate (2 parts), a silica fine powder (20 parts) and diatomite (54 parts) are mixed, then to the mixture is added any one of the present compounds 1-1 to 1-98 (20 parts), and mixed to give a wettable powder of each compound.

Formulation Example 3

To any one of the present compounds 1-1 to 1-98 (2 parts) is added a silica fine powder (1 part), calcium lignin sulfonate (2 parts), bentonite (30 parts), and kaolin clay (65 parts), and mixed. Then, to the mixture is added an appropriate amount of water, further stirred, granulated with a granulator, and draft-dried to give granules of each compound.

Formulation Example 4

Any one of the present compounds 1-1 to 1-98 (1 part) is dissolved in an appropriate amount of acetone. To the mixture is added a silica fine powder (5 parts), PAP (0.3 parts), and pyrophyllite (93.7 parts), and well stirred. Then, acetone is removed by evaporation to give dusts of each compound.

Formulation Example 5

A mixture (weight ratio=1:1) of polyoxyethylene alkyl ether sulfate ammonium salt and white carbon (35 parts), any one of the present compounds 1-1 to 1-98 (10 parts), and water (55 parts) are mixed, pulverized by a wet grinding method to give a suspension concentrate of each compound.

Formulation Example 6

Any one of the present compounds 1-1 to 1-98 (0.1 parts) is dissolved in xylene (5 parts) and trichloroethane (5 parts), and mixed with deodorized kerosine (89.9 parts) to give an oil solutions of each compound.

Formulation Example 7

Any one of the present compounds 1-1 to 1-98 (10 mg) is dissolved in acetone (0.5 ml). The mixture is added to animal powdered solid feed (powdered solid feed for breeding, CE-2, from CLEA Japan, Inc.) (5 g) and mixed uniformly. Then, acetone is removed by evaporation to give a poison bait of each compound.

Formulation Example 8

Any one of the present compounds 1-1 to 1-98 (0.1 parts) and Neothiosol (Chuo Kasei Co. Ltd.) (49.9 parts) are charged into an aerosol container. After an aerosol valve is attached to the container, dimethyl ether (25 parts) and LPG (25 parts) are charged into the container. The container is vibrated, and attaching an actuator to give an oily aerosol of each compound.

Formulation Example 9

Any one of the present compounds 1-1 to 1-98 (0.6 parts), BHT (2,6-di-tert-butyl-4-methylphenol) (0.01 parts), xylene (5 parts), deodorized kerosine (3.39 parts), and an emulsifier (RHEODOL MO-60, manufactured by Kao Corporation) (1 part) are mixed and dissolved. The mixture and distilled water (50 parts) are charged into an aerosol container, and attaching a valve. Then, propellant (LPG) (40 parts) is pressure-charged into the container through the valve to give an aqueous aerosol of each compound.

Formulation Example 10

Any one of the present compounds 1-1 to 1-98 (0.1 g) is dissolved in propylene glycol (2 ml), and the solution is impregnated into a porous ceramic plate (4.0×4.0 cm, 1.2 cm thick) to give a heat-type smoking agent.

Formulation Example 11

Any one of the present compounds 1-1 to 1-98 (5 parts) and ethylene-methyl methacrylate copolymer (proportion of methyl methacrylate in the copolymer: 10 wt %, Acryft WD301, manufactured by Sumitomo Chemical Co., Ltd) (95 parts) are melt-mixed by a sealed, pressurized kneader (manufactured by Moriyama Co., Ltd.). The resulting mixture is extruded from a molding machine via a molding die to give a rod-shaped molded article (15 cm long, 3 mm diameter).

Formulation Example 12

Any one of the present compounds 1-1 to 1-98 (5 parts) and soft vinyl chloride resin (95 parts) are melt-mixed by a sealed, pressurized kneader (manufactured by Moriyama Co., Ltd.). The resulting mixture is extruded from a molding machine via a molding die to give a rod-shaped molded article (15 cm long, 3 mm diameter).

Formulation Example 13

Any one of the present compounds 1-1 to 1-98 (100 mg), lactose (68.75 mg), corn starch (237.5 mg), microcrystalline cellulose (43.75 mg), polyvinyl pyrrolidone (18.75 mg), sodium carboxymethyl starch (28.75 mg), and magnesium stearate (2.5 mg) are mixed, and the resulting mixture is compressed to a suitable size to give tablets.

Formulation Example 14

Any one of the present compounds 1-1 to 1-98 (25 mg), lactose (60 mg), corn starch (25 mg), carmellose calcium (6 mg), and 5% hydroxypropylmethyl cellulose (appropriate amount) are mixed, and the resulting mixture is packed into hard shell gelatin capsules or hydroxypropyl methylcellulose capsules to give capsules.

Formulation Example 15

To a mixture of any one of the present compounds 1-1 to 1-98 (1000 mg), fumaric acid (500 mg), sodium chloride (2000 mg), methylparaben (150 mg), propylparaben (50 mg), granulated sugar (25000 mg), 70% solution of sorbitol (13000 mg), VeegumK (Vanderbilt Co) (100 mg), a perfume (35 mg), and a colorant (500 mg) is added distilled water such that the final volume becomes 100 ml, and well mixed to give a suspension for oral administration.

Formulation Example 16

Any one of the present compounds 1-1 to 1-98 (5% by weight) is dissolved in Polysorbate 85 (5% by weight), benzyl alcohol (3% by weight), and propylene glycol (30% by weight), and a phosphate buffer is added thereto such that the pH becomes 6.0-6.5, and water is added thereto to be a final volume to give a liquid for oral administration.

Formulation Example 17

Aluminum distearate (5% by weight) is dispersed into a fractionated coconut oil (57% by weight) and Polysorbate 85 (3% by weight) by heating. After cooling to room temperature, saccharine (25% by weight) is dispersed into the oily vehicle. Then, any one of the present compounds 1-1 to 1-98 (10% by weight) is added to the mixture to give a paste for oral administration.

Formulation Example 18

Any one of the present compounds 1-1 to 1-98 (5% by weight) and a limestone powder (95% by weight) are mixed, and then the mixture is subjected to a wet granulation method to give granules for oral administration.

Formulation Example 19

Any one of the present compounds 1-1 to 1-98 (5 parts) is dissolved in diethylene glycol monoethyl ether (80 parts), and then propylene carbonate (15 parts) is mixed therewith to give a spot-on liquid.

Formulation Example 20

Any one of the present compounds 1-1 to 1-98 (10 parts) is dissolved in diethylene glycol monoethyl ether (70 parts), and then 2-octyldodecanol (20 parts) is mixed therewith to give a pour-on liquid.

Formulation Example 21

To any one of the present compounds 1-1 to 1-98 (0.5 parts) are added Nikkol TEALS-42 (Nikko Chemicals Co., Ltd., 42% aqueous solution of triethanolamine lauryl sulfate) (60 parts) and propylene glycol (20 parts). After stirring and mixing enough to form a homogeneous solution, water (19.5 parts) is added thereto and the mixture is stirred and mixed adequately to give a homogeneous shampoo formulation.

Formulation Example 22

Any one of the present compounds 1-1 to 1-98 (0.15% by weight), an animal feed (95% by weight), and a mixture (4.85% by weight) of dicalcium phosphate, diatomite, Aerosil, and carbonate (or chalk) are stirred and mixed adequately to give a premix for animal feed.

Formulation Example 23

Any one of the present compounds 1-1 to 1-98 (7.2 g) and Vosco S-55 (manufactured by Maruishi Pharmaceutical Co., Ltd.) (92.8 g) are dissolved and mixed at 100° C. Then, the mixture is poured into a suppository mold, and cooled and solidified to give a suppository.

Formulation Example 24

Any one of the present compounds 1-1 to 1-98 (10 parts), polyoxyalkylene arylphenyl ether phosphate salts, propylene glycol (5 parts), a silicone antifoamer (0.2 parts) and water (58.5 parts) are mixed, and pulverized by a wet grinding method to give a suspension. To the resultant suspension, a mixture of magnesium aluminum silicate (0.4 parts), xanthane gum (0.2 parts), a preservative (0.2 parts) and water (23.5 parts) is added and mixed to give a suspension concentrate of each compound.

Formulation Example 25

To an aqueous solution of polyvinyl alcohol obtained by dissolving polyvinyl alcohol (3 parts) in water (43.5 parts), any one of the present compounds 1-1 to 1-98 (10 parts), and an aromatic hydrocarbon (Solvesso 200ND, manufactured by ExxonMobil Chemical) (20 parts) are added and the mixture is stirred by a stirrer to give a suspension. To the resultant suspension, a mixture of magnesium aluminum silicate (0.3 parts), xanthane gum (0.15 parts), a preservative (0.2 parts) and water (17.65 parts) and propylene glycol (5 parts) and a silicone antifoamer (0.2 parts) are added and mixed to give a suspension concentrate of each compound.

Formulation Example 26

Any one of the present compounds 1-1 to 1-98 (3.6 parts) is mixed with acetone (14.3 parts) to give a solution. To the solution are added zinc oxide (0.2 parts), α-starch (1.0 parts) and azodicarbonamide (42.8 parts). After adding water (38.1 parts) thereto, the mixture is kneaded and formed into a granular shape by using an extruder, and then dried. The resultant granules containing the present compound are put into a space in the upper part of a container having a partition wall made of aluminum in the central part thereof, and calcium oxide (50 g) is put into a space in the lower part of the container, to give a smoking agent.

Formulation Example 27

Zinc oxide (0.5 parts), α-starch (2 parts), and azodicarbonamide (97.5 parts) are mixed and water is added thereto. The mixture is kneaded and formed into a granular shape by using an extruder, and then dried to give granules. The granules (2 g) is uniformly impregnated with a solution of any one of the present compounds 1-1 to 1-98 (0.58 g) in acetone and then dried to give granules containing any of the present compounds 1-1 to 1-98. The resultant granules containing the present compound are put into a space in the upper part of a container having a partition wall made of aluminum in the central part thereof, and calcium oxide (50 g) is put into a space in the lower part of the container, to give a smoking agent.

The controlling effect on pests by the present compound will be demonstrated below with reference to Test Examples.

Test Example 1

Each test solution was prepared by diluting a formulation containing any of the present compounds 1-4, 1-5, 1-6, 1-8, 1-9, 1-10, 1-18, 1-19, 1-20, 1-29, 1-46, 1-48, 1-49, 1-50, 1-63, 1-65 and 1-76 as obtained in Formulation Example 5, with water so as to give 500 ppm of the concentration of the active ingredient.

On the other hand, on a cucumber seedling (the first true leaf stage) planted in a plastic cup was inoculated with about 30 *Aphis gossypii* (whole stage), and leaving it for a day. Twenty (20) ml of each test solution was sprayed on the seedling.

Six (6) days after spraying, the number of the surviving *Aphis gossypii* parasitized on the leaves of the cucumber was examined, and a control value was calculated according to the following equation:

Controlling value (%)={1−($Cb \times Tai$)/($Cai \times Tb$)}×100 wherein the symbols in the above equation represent as follows:

Cb: the number of insects in a non-treated section before treatment

Cai: the number of insects in a non-treated section on observation

Tb: the number of insects in a treated section before treatment

Tai: the number of insects in a non-treated section on observation wherein the non-treated section represents a section where the test diluted solution prepared by diluting the formulation without the present compound as in Formulation Example 5 with the same amount of water as in the treated-section was used.

As a result, in the treated-section using each test solution containing each of the present compounds 1-4, 1-5, 1-6, 1-8, 1-9, 1-10, 1-18, 1-19, 1-20, 1-29, 1-46, 1-48, 1-49, 1-50, 1-63, 1-65 and 1-76, the control value was 90 or more.

Test Example 2

Each test solution was prepared by diluting a formulation containing any of the present compounds 1-4, 1-5, 1-8, 1-9, 1-10 and 1-76 as obtained in Formulation Example 5, with water so as to give 500 ppm of the concentration of the active ingredient.

On the other hand, a cucumber seedling (the second true leaf stage) planted in a plastic cup was drenched at its foot with 5 ml of each test solution, and kept in a greenhouse of 25° C. for 7 days. On the cucumber leaf surface was inoculated with about 30 *Aphis gossypii* (whole stage), and further kept in the greenhouse for 6 days, then the number of insect of living *Aphis gossypii* parasitized on the leaves of the cucumber was examined, and a control value was calculated according to the following equation:

Controlling value (%)={1−($Cb \times Tai$)/($Cai \times Tb$)}×100 wherein the symbols in the above equation represent as follows:

Cb: the number of insects in a non-treated section before treatment

Cai: the number of insects in a non-treated section on observation

Tb: the number of insects in a treated section before treatment

Tai: the number of insects in a non-treated section on observation wherein the non-treated section represents a section where the test diluted solution prepared by diluting the formulation without the present compound as in Formulation Example 5 with the same amount of water as in the treated-section was used.

As a result, in the treated-section using each test solution containing each of the present compounds 1-4, 1-5, 1-8, 1-9, 1-10 and 1-76, the control value was 90% or more.

Test Example 3

Each test solution was prepared by diluting a formulation containing any of the present compounds 1-4, 1-6, 1-8, 1-9, 1-10, 1-18, 1-19, 1-48, 1-49 and 1-76 as obtained in Formulation Example 5, with water so as to give 500 ppm of the concentration of the active ingredient.

On the other hand, a rice seedling (the second leaf stage) planted in a polyethylene cup was sprayed with 10 ml of each test solution. After air-drying, 20 third-fourth instar larvae of *Nilaparvata lugens* were released, and kept in the greenhouse of 25° C. After 6 days, the number of insect of living *Nilaparvata lugens* parasitized on the rice was examined, and a control value was calculated according to the following equation:

Controlling value (%)={1−($Cb \times Tai$)/($Cai \times Tb$)}×100 wherein the symbols in the above equation represent as follows:

Cb: the number of insects in a non-treated section before treatment

Cai: the number of insects in a non-treated section on observation

Tb: the number of insects in a treated section before treatment

Tai: the number of insects in a non-treated section on observation wherein the non-treated section represents a section where the test diluted solution prepared by diluting the formulation without the present compound as in Formulation Example 5 with the same amount of water as in the treated-section was used.

As a result, in the treated-section using each test solution containing each of the present compounds 1-4, 1-6, 1-8, 1-9, 1-10, 1-18, 1-19, 1-48, 1-49 and 1-76, the control value was 90% or more.

Test Example 4

Each test solution was prepared by diluting a formulation containing any of the present compounds 1-4, 1-6, 1-8, 1-9, 1-10, 1-19, 1-48, 1-49, 1-63 and 1-76 as obtained in Formulation Example 5, with water so as to give 500 ppm of the concentration of the active ingredient.

On the other hand, a rice seedling (2 weeks after sowing, the second leaf stage) planted in a plastic cup was drenched at its foot with 5 ml of each test solution, and kept in a greenhouse of 25° C. for 7 days. Twenty (20) third-fourth instar larvae of *Nilaparvata lugens* were released, and further kept in the greenhouse for 6 days, then the number of insect of living *Nilaparvata lugens* parasitized on the rice was examined, and a control value was calculated according to the following equation:

Controlling value (%)={1−($Cb \times Tai$)/($Cai \times Tb$)}×100 wherein the symbols in the above equation represent as follows:

Cb: the number of insects in a non-treated section before treatment

Cai: the number of insects in a non-treated section on observation

Tb: the number of insects in a treated section before treatment

Tai: the number of insects in a non-treated section on observation wherein the non-treated section represents a section where the test diluted solution prepared by diluting the formulation without the present compound as in Formulation Example 5 with the same amount of water as in the treated-section was used.

As a result, in the treated-section using each test solution containing each of the present compounds 1-4, 1-6, 1-8, 1-9, 1-10, 1-19, 1-48, 1-49, 1-63 and 1-76, the control value was 90% or more.

Test Example 5

Each test solution is prepared by diluting a formulation containing any of the present compounds as obtained in Formulation Example 5, with water so as to give 500 ppm of the concentration of the active ingredient.

On the other hand, Bemisia tabaci adult is released on a tomato seedling (the third true leaf stage) planted in a polyethylene cup, and made to lay eggs for about 72 hours. The tomato seedling is kept in a greenhouse for 8 days. When first instar larvae hatch from the eggs, the above test spray solution is sprayed in the amount of 20 ml/cup. The cup is kept in a greenhouse at 25° C. After the keeping for 7 days, the number of surviving larvae on the tomato leaves is examined, and a control value is calculated according to the following equation:

Controlling value (%)={1−($Cb \times Tai$)/($Cai \times Tb$)}×100 wherein the symbols in the above equation represent as follows:

Cb: the number of insects in a non-treated section before treatment

Cai: the number of insects in a non-treated section on observation

Tb: the number of insects in a treated section before treatment

Tai: the number of insects in a non-treated section on observation wherein the non-treated section represents a section where the test diluted solution prepared by diluting the formulation without the present compound as in Formulation Example 5 with the same amount of water as in the treated-section was used.

Test Example 6

Each test solution was prepared by diluting a formulation containing any of the present compounds 1-4, 1-5, 1-6, 1-8, 1-9, 1-10, 1-16, 1-18, 1-19, 1-20, 1-29, 1-46, 1-48, 1-49, 1-50, 1-63 and 1-76 as obtained in Formulation Example 5, with water so as to give 500 ppm of the concentration of the active ingredient.

On the other hand, Cabbage (the third leaf stage) planted in a polyethylene cup was sprayed with 20 mL/cup of each test solution. After the test solution was dried, the aerial part was cut off, and then placed in a 50 mL volume cup. Five (5) second instar larvae of Plutella xylostella were released into the cup, and the cup was sealed with a lid. After the cup was kept at 25° C. for 5 days, the number of living insects was counted. A death rate was calculated according to the following equation:

Death rate (%)=(Number of dead insects/Number of tested insects)×100

As a result, in the treated-section using each test solution containing each of the present compounds 1-4, 1-5, 1-6, 1-8, 1-9, 1-10, 1-16, 1-18, 1-19, 1-20, 1-29, 1-46, 1-48, 1-49, 1-50, 1-63 and 1-76, the death rate was 80% or more.

Test Example 7

Each test spray solution was prepared by diluting a formulation containing any of the present compounds 1-4, 1-5, 1-6, 1-8, 1-9, 1-10, 1-16, 1-18, 1-19, 1-20, 1-46, 1-48, 1-49, 1-50, 1-63 and 1-76 as obtained in Formulation Example 5, with water so as to give 500 ppm of the concentration of the active ingredient.

On the other hand, an apple seeding was planted in a plastic cup, and grown until the seventh-eighth leaf was spread. The apple plant was sprayed with 20 mL/cup of each test solution. After the test solution was dried, 60 first-instar Adoxophyes orana fasciata were released, and the cup was covered with a plastic cup upside-down which the bottom was cut off and a filter paper was put thereon. After 7 days, the number of living insects was counted. A death rate was calculated according to the following equation:

Death rate (%)=(Number of dead insects/Number of tested insects)×100

As a result, in the treated-section using each test solution containing each of the present compounds 1-4, 1-5, 1-6, 1-8, 1-9, 1-10, 1-16, 1-18, 1-19, 1-20, 1-46, 1-48, 1-49, 1-50, 1-63 and 1-76, the death rate was 900 or more.

Test Example 8

Each test solution was prepared by diluting a formulation containing any of the present compounds 1-4, 1-6, 1-8, 1-9, 1-10, 1-63 and 1-95 as obtained in Formulation Example 5, with water so as to give 500 ppm of the concentration of the active ingredient.

A filter paper having a diameter of 5.5 cm was spread on the bottom of a polyethylene cup having a diameter of 5.5 cm and each test solution (0.7 ml) was added dropwise onto the filter paper. As a bait sucrose (30 mg) was uniformly placed on the filter paper. Into the polyethylene cup, 10 female imagoes of Musca domestica were released and the cup was sealed with a lid. After 24 hours, the number of surviving Musca domestica was examined and the death rate of the pest was calculated according to the following equation:

Death rate (%)=(Number of dead insects/Number of tested insects)×100

As a result, in the treatment with each test solution containing each of the present compounds 1-4, 1-6, 1-8, 1-9, 1-10, 1-63 and 1-95, the death rate was 100%.

Test Example 9

Each test solution was prepared by diluting a formulation containing any of the present compounds 1-9 and 1-19 as obtained in Formulation Example 5, with water so as to give 500 ppm of the concentration of the active ingredient.

A filter paper having a diameter of 5.5 cm was spread on the bottom of a polyethylene cup having a diameter of 5.5 cm and each test solution (0.7 ml) was added dropwise onto the filter paper. Sucrose (30 mg) as a bait was uniformly placed on the filter paper. Into the polyethylene cup, 2 male imagoes of Blattalla germanica were released and the cup was sealed with a lid. After 6 hours, the number of surviving

*Blattalla germanica* was examined and the death rate of the pest was calculated according to the following equation:

Death rate (%)=(Number of dead insects/Number of tested insects)×100

As a result, in the treatment with each test solution containing each of the present compounds 1-9 and 1-19, the death rate was 100%.

Test Example 10

Each test solution was prepared by diluting a formulation containing any of the present compounds 1-5, 1-6, 1-8, 1-9, 1-10, 1-18, 1-19, 1-20, 1-29, 1-46, 1-48, 1-49, 1-50, 1-61, 1-63 and 1-76 as obtained in Formulation Example 5, with water so as to give 500 ppm of the concentration of the active ingredient.

To ion-exchanged water (100 mL), each test solution (0.7 ml) was added (active ingredient concentration: 3.5 ppm). Into the solution, 20 last-instar larvae of *Culex pipiens pallens* were released. One day after, the number of surviving *Culex pipiens pallens* was examined and the death rate of the pest was calculated according to the following equation:

Death rate (%)=(Number of dead insects/Number of tested insects)×100

As a result, in the treatment with each test solution containing each of the present compounds 1-5, 1-6, 1-8, 1-9, 1-10, 1-18, 1-19, 1-20, 1-29, 1-46, 1-48, 1-49, 1-50, 1-61, 1-63 and 1-76, the death rate was 950 or more.

Test Example 11

Each 2 mg of the present compounds is put into a screw tube (Maruemu® No. 5; 27×55 mm). Acetone (0.2 ml) is added thereto and sealed with a cap. After dissolving the compound in acetone, the screw tube is rotated and inverted to uniformity coat the solution onto the whole inner wall of the tube. After removing the cap, the solution is air-dried for about 2 hours. Then, non-blood-sucking nymphal ticks, *Haemaphysalis longicornis* (5 ticks/group) are released into the tube, and the tube is sealed with the cap. After 2 days, the number of dead tick was counted, and a death rate is calculated according to the following equation:

Death rate (%)=(Number of dead tick/Number of tested tick)×100

As a result, in the treatment with each test solution containing each of the present compounds, the death rate is 100%.

Test Example 12

Any of the present compounds 1-6, 1-8, 1-9 and 1-10 (10 mg) was dissolved in a mixed solution (0.1 ml) of xylene, DMF and Sorpol® 3005X (manufactured by Toho Chemical Industry Co., Ltd.) in a ratio of 4:4:1 to obtain a formulation. Each formulation was diluted with water so as to give 50 ppm of the concentration of the active ingredient.

On the other hand, a rice seedling (2.5 leaf stage) planted in a polyethylene cup was sprayed with 10 ml of each test solution. After air-drying the seedling, 10 third instar larvae of *Laodelphax striatella* were released, and kept in the greenhouse of 25° C. After 5 days, the number of living insects was counted. A death rate was calculated according to the following equation:

Death rate (%)={10−(Number of living insects after 5 days)/10}×100

As a result, in the treated-section using each test solution containing each of the present compounds 1-6, 1-8, 1-9 and 1-10, the control value was 100%.

Test Example 13

Any of the present compounds 1-6, 1-8, 1-9 and 1-10 (10 mg) was dissolved in a mixed solution (0.1 ml) of xylene, DMF and Sorpol® 3005X (manufactured by Toho Chemical Industry Co., Ltd.) in a ratio of 4:4:1 to obtain a formulation. Each formulation was diluted with water so as to give 50 ppm of the concentration of the active ingredient.

On the other hand, a rice seedling (2.5 leaf stage) planted in a polyethylene cup was sprayed with 10 ml of each test solution. After air-drying the seedling, 10 third instar larvae of *Sogatella furcifera* were released, and kept in the greenhouse of 25° C. After 5 days, the number of living insects was counted. A death rate was calculated according to the following equation:

Death rate (%)={10−(Number of living insects after 5 days)/10}×100

As a result, in the treated-section using each test solution containing each of the present compounds 1-6, 1-8, 1-9 and 1-10, the control value was 100%.

INDUSTRIAL APPLICABILITY

The present compound has a controlling effect on pests and is thus useful as an active ingredient of a pest control agent.

The invention claimed is:
1. A fused heterocyclic compound represented by formula (1):

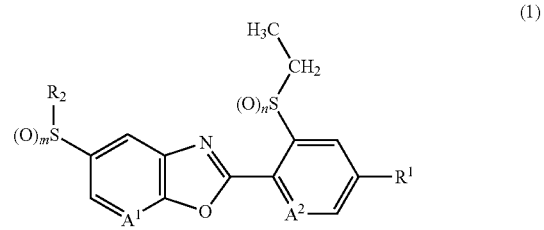

wherein
$A^1$ represents $N(O)_p$ or CH,
$A^2$ represents $N(O)_q$,
$R^1$ represents a trifluoromethyl group, a halogen atom or a hydrogen atom,
$R^2$ represents a C1-C3 perfluoroalkyl group,
p represents 0 or 1,
q represents 0 or 1,
n represents 0, 1 or 2,
m represents 0, 1 or 2,
with the proviso that when $A^1$ is NO and/or $A^2$ is NO, n represents 2 and m represents 2.

2. The fused heterocyclic compound according to claim 1, wherein $A^1$ is CH.

3. The fused heterocyclic compound according to claim 1, wherein $A^1$ is N.

4. The fused heterocyclic compound according to claim 1, wherein $R^1$ is a hydrogen atom.

5. The fused heterocyclic compound according to claim 1, wherein $R^1$ is a trifluoromethyl group.

6. The fused heterocyclic compound according to claim 1, wherein $R^2$ is a trifluoromethyl group.

7. The fused heterocyclic compound according to claim 1, wherein p is 0 and q is 0.

8. A pest control agent comprising a fused heterocyclic compound according to claim 1 and an inert carrier.

9. The pest control agent according to claim 8, wherein the inert carrier is water, and the fused heterocyclic compound is dispersed in the water containing a surfactant.

10. A method for controlling an arthropod pest, which comprises applying an effective amount of the fused heterocyclic compound according to claim 1.

11. The method according to claim 10, which comprises applying an effective amount, of the fused heterocyclic compound to stem and leaf of a plant or a soil where a plant is grown.

12. The pest control agent according to claim 8, wherein the inert carrier is an eating carrier.

13. The pest control agent according to claim 8, wherein the inert carrier is a solvent and a propellant gas.

14. The method according to claim 10, which comprises spraying a pest control agent comprising the fused heterocyclic compound and an inert carrier comprising a solvent and a propellant gas to an arthropod pest and/or a habitat of an arthropod pest.

15. The pest control agent according to claim 8, wherein the inert carrier is a gas-forming agent.

16. The method according to claim 10, which comprises applying the fused heterocyclic compound to the body surface of an animal parasitized by an arthropod pest.

* * * * *